(12) United States Patent
Chan et al.

(10) Patent No.: US 8,518,705 B2
(45) Date of Patent: Aug. 27, 2013

(54) METHODS AND APPARATUSES FOR STRETCHING POLYMERS

(75) Inventors: Eugene Y. Chan, Boston, MA (US);
Lance C. Gleich, Somerville, MA (US);
Parris S. Wellman, Somerville, MA (US)

(73) Assignee: PathoGenetix, Inc., Woburn, MA (US)

( * ) Notice: Subject to any disclaimer, the term of this patent is extended or adjusted under 35 U.S.C. 154(b) by 1645 days.

(21) Appl. No.: 10/775,599

(22) Filed: Feb. 10, 2004

(65) Prior Publication Data

US 2004/0166025 A1 Aug. 26, 2004

Related U.S. Application Data

(63) Continuation of application No. 09/636,793, filed on Aug. 11, 2000, now Pat. No. 6,696,022.

(60) Provisional application No. 60/149,020, filed on Aug. 13, 1999.

(51) Int. Cl.
*B01L 3/00* (2006.01)

(52) U.S. Cl.
USPC .............. 436/94; 422/502; 422/503; 436/86

(58) Field of Classification Search
USPC .............. 422/99, 82.05, 101, 102, 68.1, 502, 422/503; 436/86, 94
See application file for complete search history.

(56) References Cited

U.S. PATENT DOCUMENTS

| | | | |
|---|---|---|---|
| 4,147,621 A | 4/1979 | Giddings | |
| 4,833,332 A | 5/1989 | Robertson, Jr. et al. | |
| 4,979,824 A | 12/1990 | Mathies et al. | |
| 5,079,169 A | 1/1992 | Chu et al. | |
| 5,141,651 A | 8/1992 | Giddings | |
| 5,169,511 A | 12/1992 | Allington et al. | |
| 5,274,240 A | 12/1993 | Mathies et al. | |
| 5,304,487 A | 4/1994 | Wilding et al. | |
| 5,324,401 A | 6/1994 | Yeung et al. | |
| 5,356,776 A | 10/1994 | Kambara et al. | |
| 5,374,527 A | 12/1994 | Grossman | |

(Continued)

FOREIGN PATENT DOCUMENTS

| | | |
|---|---|---|
| EP | 0391674 | 10/1990 |
| EP | 1 380 337 A2 | 1/2004 |

(Continued)

OTHER PUBLICATIONS

PCT International Search Report, (Dec. 27, 2000).

(Continued)

*Primary Examiner* — Jan Ludlow
(74) *Attorney, Agent, or Firm* — Wolf, Greenfield & Sacks, P.C.

(57) ABSTRACT

The present invention provides structures and methods that allow polymers of any length, including nucleic acids containing entire genomes, to be stretched into a long, linear conformation for further analysis. The present invention also provides structures and methods for selecting and stretching polymers based on their lengths. Polymers are loaded into a device and run through the structures. Stretching is achieved by, e.g., applying shear forces as the polymer passes through the structures, placing obstacles in the path of the polymer, or a combination thereof. Since multiple molecules may be stretched in succession, extremely high throughput screening, e.g., screening of more than one molecule per second, is achieved.

33 Claims, 34 Drawing Sheets

(56) References Cited

U.S. PATENT DOCUMENTS

| | | | |
|---|---|---|---|
| 5,427,663 A | 6/1995 | Austin et al. |
| 5,449,917 A | 9/1995 | Clements |
| 5,538,898 A | 7/1996 | Wickramasinghe et al. |
| 5,599,664 A | 2/1997 | Schwartz et al. |
| 5,601,694 A | 2/1997 | Maley et al. |
| 5,612,181 A | 3/1997 | Fourmentin-Guilbert |
| 5,675,155 A | 10/1997 | Pentoney, Jr. et al. |
| 5,699,157 A | 12/1997 | Parce |
| 5,707,797 A | 1/1998 | Windle |
| 5,711,861 A | 1/1998 | Ward et al. |
| 5,711,868 A | 1/1998 | Maley et al. |
| 5,720,928 A | 2/1998 | Schwartz et al. |
| 5,795,782 A | 8/1998 | Church et al. |
| 5,798,215 A * | 8/1998 | Cathey et al. | 435/7.9 |
| 5,837,115 A | 11/1998 | Austin et al. |
| 5,840,862 A | 11/1998 | Bensimon et al. |
| 5,843,767 A | 12/1998 | Beattie |
| 5,846,724 A | 12/1998 | Bensimon et al. |
| 5,846,727 A | 12/1998 | Soper et al. |
| 5,846,832 A | 12/1998 | Oefner et al. |
| 5,851,769 A | 12/1998 | Gray et al. |
| 5,867,266 A | 2/1999 | Craighead |
| 5,879,625 A | 3/1999 | Roslaniec et al. |
| 5,880,473 A | 3/1999 | Ginestet |
| 5,906,723 A | 5/1999 | Mathies et al. |
| 5,971,158 A | 10/1999 | Yager et al. |
| 6,001,229 A | 12/1999 | Ramsey |
| 6,008,892 A | 12/1999 | Kain et al. |
| 6,015,714 A | 1/2000 | Baldarelli et al. |
| 6,054,327 A | 4/2000 | Bensimon et al. |
| 6,071,394 A | 6/2000 | Cheng et al. |
| 6,090,251 A * | 7/2000 | Sundberg et al. | 204/453 |
| 6,100,541 A | 8/2000 | Nagle et al. |
| 6,120,666 A | 9/2000 | Jacobson et al. |
| 6,139,800 A | 10/2000 | Chandler |
| 6,150,089 A | 11/2000 | Schwartz |
| 6,193,647 B1 | 2/2001 | Beebe et al. |
| 6,210,896 B1 | 4/2001 | Chan |
| 6,210,973 B1 | 4/2001 | Petit |
| 6,214,246 B1 | 4/2001 | Craighead |
| 6,263,286 B1 | 7/2001 | Gilmanshin et al. |
| 6,294,136 B1 | 9/2001 | Schwartz |
| 6,319,469 B1 | 11/2001 | Mian et al. |
| 6,344,319 B1 | 2/2002 | Bensimon et al. |
| 6,355,420 B1 | 3/2002 | Chan |
| 6,403,311 B1 | 6/2002 | Chan |
| 6,432,630 B1 | 8/2002 | Blankenstein |
| 6,444,992 B1 | 9/2002 | Kauvar et al. |
| 6,506,609 B1 | 1/2003 | Wada et al. |
| 6,562,307 B1 | 5/2003 | Schuch et al. |
| 6,605,454 B2 | 8/2003 | Barenburg et al. |
| 6,641,708 B1 | 11/2003 | Becker et al. |
| 6,660,480 B2 | 12/2003 | Ramsey et al. |
| 6,696,022 B1 | 2/2004 | Chan et al. |
| 6,762,059 B2 | 7/2004 | Chan et al. |
| 6,766,817 B2 | 7/2004 | da Silva |
| 6,767,731 B2 | 7/2004 | Hannah et al. |
| 6,770,182 B1 | 8/2004 | Griffiths et al. |
| 6,772,070 B2 | 8/2004 | Gilmanshin et al. |
| 6,790,671 B1 | 9/2004 | Austin et al. |
| 6,927,065 B2 | 8/2005 | Chan et al. |
| 7,262,859 B2 | 8/2007 | Larson et al. |
| 7,282,330 B2 | 10/2007 | Zhao et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,595,160 B2 | 9/2009 | White et al. |
| 7,828,948 B1 | 11/2010 | Hatch et al. |
| 7,888,011 B2 | 2/2011 | Nilsen et al. |
| 7,977,048 B2 | 7/2011 | Gilmanshin |
| 2001/0030130 A1 | 10/2001 | Ricco et al. |
| 2001/0055817 A1 | 12/2001 | Malmqvist et al. |
| 2002/0008028 A1 | 1/2002 | Jacobson et al. |
| 2002/0029814 A1 | 3/2002 | Unger et al. |
| 2002/0034748 A1 | 3/2002 | Quake et al. |
| 2002/0039737 A1 | 4/2002 | Chan et al. |
| 2002/0055167 A1 | 5/2002 | Pourahmadi et al. |
| 2002/0058332 A1 | 5/2002 | Quake et al. |
| 2002/0072243 A1 | 6/2002 | Craighead et al. |
| 2002/0079008 A1 | 6/2002 | Chien et al. |
| 2002/0109844 A1 | 8/2002 | Christel et al. |
| 2002/0110495 A1 | 8/2002 | Hunt et al. |
| 2002/0110818 A1 | 8/2002 | Chan |
| 2002/0119455 A1 | 8/2002 | Chan |
| 2002/0187508 A1 | 12/2002 | Wong |
| 2002/0197639 A1 | 12/2002 | Shia et al. |
| 2003/0058440 A1 | 3/2003 | Scott et al. |
| 2003/0059822 A1 | 3/2003 | Chan et al. |
| 2003/0104466 A1 * | 6/2003 | Knapp et al. | 435/6 |
| 2003/0124623 A1 | 7/2003 | Yager et al. |
| 2003/0162181 A1 | 8/2003 | Yang et al. |
| 2003/0215864 A1 | 11/2003 | Gilmanshin et al. |
| 2003/0235854 A1 | 12/2003 | Chan |
| 2004/0009612 A1 | 1/2004 | Zhao et al. |
| 2004/0028580 A1 | 2/2004 | Futami et al. |
| 2004/0053399 A1 | 3/2004 | Gilmanshin |
| 2004/0126279 A1 | 7/2004 | Renzi et al. |
| 2004/0166025 A1 | 8/2004 | Chan et al. |
| 2004/0188254 A1 | 9/2004 | Spaid |
| 2004/0214211 A1 | 10/2004 | Gilmanshin et al. |
| 2004/0235014 A1 | 11/2004 | Nadel et al. |
| 2005/0042665 A1 | 2/2005 | Gilmanshin |
| 2005/0112595 A1 | 5/2005 | Zhao et al. |
| 2005/0112606 A1 | 5/2005 | Fuchs et al. |
| 2005/0112620 A1 | 5/2005 | Chan |
| 2005/0112671 A1 | 5/2005 | Maletta et al. |
| 2005/0123944 A1 | 6/2005 | Neely et al. |
| 2005/0123974 A1 | 6/2005 | Gilmanshin et al. |
| 2005/0142595 A1 | 6/2005 | Maletta et al. |
| 2005/0148064 A1 | 7/2005 | Yamakawa et al. |
| 2005/0153354 A1 | 7/2005 | Gilmanshin et al. |
| 2005/0196790 A1 | 9/2005 | Rooke et al. |
| 2005/0221408 A1 | 10/2005 | Nalefski et al. |
| 2006/0078915 A1 | 4/2006 | Fuchs et al. |
| 2006/0134679 A1 | 6/2006 | Larson |
| 2006/0160209 A1 | 7/2006 | Larson et al. |
| 2006/0160231 A1 | 7/2006 | Nadel et al. |
| 2006/0191792 A1 | 8/2006 | Herr et al. |
| 2006/0204978 A1 | 9/2006 | Nilsen et al. |
| 2006/0211055 A1 | 9/2006 | Hafeman et al. |
| 2006/0228747 A1 | 10/2006 | Fuchs et al. |
| 2006/0292616 A1 | 12/2006 | Neely et al. |
| 2006/0292617 A1 | 12/2006 | Neely et al. |
| 2007/0031961 A1 | 2/2007 | Ho et al. |
| 2007/0042406 A1 | 2/2007 | Yantz et al. |
| 2007/0128083 A1 | 6/2007 | Yantz et al. |
| 2007/0166743 A1 | 7/2007 | Gilmanshin |
| 2008/0003689 A1 | 1/2008 | Lee et al. |
| 2008/0085521 A1 | 4/2008 | Knapp et al. |
| 2008/0085552 A1 | 4/2008 | Larson et al. |
| 2008/0103296 A1 | 5/2008 | Zhao et al. |
| 2008/0254549 A1 | 10/2008 | Fuchs et al. |
| 2010/0035247 A1 | 2/2010 | Burton et al. |
| 2010/0112576 A1 | 5/2010 | Patil |
| 2010/0116025 A1 | 5/2010 | Gouveia et al. |
| 2010/0120101 A1 | 5/2010 | Patil et al. |
| 2010/0294665 A1 | 11/2010 | Allen et al. |
| 2012/0283955 A1 | 11/2012 | Cameron et al. |

FOREIGN PATENT DOCUMENTS

| | | |
|---|---|---|
| JP | 63-196845 A | 8/1988 |
| WO | WO 93/22463 | 11/1993 |
| WO | WO 94/16313 A2 | 7/1994 |
| WO | WO 97/06278 | 2/1997 |
| WO | WO 98/10097 A2 | 3/1998 |
| WO | WO-98/10097 A2 | 3/1998 |
| WO | WO 98/35012 | 8/1998 |
| WO | WO 98/35012 A2 | 8/1998 |
| WO | WO-99/09042 A2 | 2/1999 |
| WO | WO 00/09757 | 2/2000 |
| WO | WO 00/50172 A1 | 8/2000 |
| WO | WO 00/56444 A2 | 9/2000 |
| WO | WO 00/70080 A1 | 11/2000 |
| WO | WO 01/28700 A1 | 4/2001 |

| WO | WO 02/29106 A2 | 4/2002 |
| WO | WO 02/099398 A1 | 12/2002 |
| WO | WO 02/101095 A1 | 12/2002 |
| WO | WO 02/101353 A2 | 12/2002 |
| WO | WO 03/000416 A2 | 1/2003 |
| WO | WO 03/025540 A2 | 3/2003 |
| WO | WO 03/091455 A1 | 11/2003 |
| WO | WO 03/100101 A1 | 12/2003 |
| WO | WO 2004/007692 A2 | 1/2004 |
| WO | WO 2004/048514 A2 | 6/2004 |
| WO | WO 2004/066185 A1 | 8/2004 |
| WO | WO 2005/078137 A1 | 8/2005 |
| WO | WO 2005/085849 A2 | 9/2005 |
| WO | WO 2007/056250 A2 | 5/2007 |
| WO | WO 2008/024483 A1 | 2/2008 |
| WO | WO 2009/009127 A2 | 1/2009 |

OTHER PUBLICATIONS

Austin, et al., "Stretch Genes," Physics Today (1997), vol. 50, pp. 32-38.
Austin, et al., "Electrophoresis and Microlithography," (1993), Analysis vol. 21, pp. 235-238.
Bakajin, et al., "Electrohydrodynamic Stretching of DNA in Confined Environments." (Mar. 23, 1998). Phys. Rev. Lett. vol. 80, No. 12, pp. 2737-2740.
Bensimon, et al., "Stretching DNA with a Receding Meniscus: Experiments and Models," (1995), Phys. Rev. Lett. vol. 74, pp. 4754-4757.
U.S. Appl. No. 60/149,020, filed Aug. 13, 1999, Chan et al.
U.S. Appl. No. 09/374,902, filed Aug. 13, 1999, Gilmanshin et al.
U.S. Appl. No. 09/373,822, filed Aug. 13, 1999, Tegenfeldt et al.
U.S. Appl. No. 60/120,414, filed Feb. 14, 1999, Tegenfeldt et al.
U.S. Appl. No. 60/096,544, filed Aug. 13, 1998, Tegenfeldt et al.
U.S. Appl. No. 09/134,411, filed Aug. 13, 1998, Chan.
Bensimon, et al., "Alignment and Sensitive Detection of DNA by a Moving Interface," (1994), Science vol. 265, pp. 2096-2098.
Bustamante, et al., "Entropic Elasticity of Lambda-phage DNA," (1994), Science vol. 265, pp. 1599-1600.
Chou, et al., "A Microfabricated Device for Sizing and Sorting DNA Molecules." (1999). Proc. Natl. Acad. Sci. USA. vol. 96, pp. 11-13.
Chu, "Laser Manipulation of Atoms and Particles," (1991), Science vol. 253, pp. 861-866.
Cluzel, et al., "DNA: An Extensible Molecule," (1996), Science vol. 271, pp. 792-794.
Deen, "Analysis of Transport Phenomena," (1998), Oxford University Press, NY, pp. 275-278.
Duke, et al., "Microfabricated Sieve for the Continuous Sorting of Macromolecules," (1998), Phys. Rev. Lett. vol. 80, pp. 1552-1555.
Ertas, "Lateral Separation of Macromolecules and Polyelectrolytes in Microlithographic Arrays," (1998). Phys. Rev. Lett. vol. 80, pp. 1548-1551.
FISHER88, Fisher Scientific Catalog (1988) p. 861.
Grandbois, et al., "How Strong is a Covalent Bond?" (1999), Science vol. 283. pp. 1727-1730.
Harrison, et al. "Capillary Electrophoresis and Sample Injection Systems Integrated on a Planar Glass Chip." (1992), Anal. Chem. vol. 64, pp. 1926-1932.
Hatfield, et al., "Dynamic Properties of an Extended Polymer in Solution," (1999), Phys. Rev. Lett. vol. 82, pp. 3548-3551.
Houseal, et al., "Real-time Imaging of Single DNA Molecules with Fluorescence Microscopy." (1998). Biophys. J. vol. 56, pp. 507-516.
Jacobson, et al., "Fused Quartz Substrates for Microchip Electrophoresis," (1995), Anal. Chem. vol. 67, pp. 2059-2063.
Kabata, et al., "Visualization of Single Molecules of RNA Polymerase Sliding Along DNA," (1993), Science vol. 262, pp. 1561-1563.
Kim, et al., "Intermediates in the Folding Reactions of Small Proteins," (1990), Annu. Rev. Biochem. vol. 59, pp. 631-660.
Lyon, et al., "Confinement and Detection of Single Molecules in Submicrometer Channels," (1997), Anal. Chem. vol. 69, pp. 3400-3405.

Marko, et al., "DNA Under High Tension: Overstretching, Undertwisting, and Relaxation Dynamics," (1998), Phy. Rev. E. vol. 27, pp. 2134-2149.
Marko, et al., "Stretching DNA," (1995), Marcromolecules vol. 28, pp. 8759-8770.
Parra, et al., "High Resolution Visual Mapping of Stretched DNA by Fluorescent Hybridization," (1993). Nature Genet vol. 5, pp. 17-21.
Perkins, et al., "Direct Observation of Tube-like Motion of a Single Polymer Chain," (1994), Science vol. 264, pp. 819-822.
Schmalzing, et al., "DNA Sequencing on Microfabricated Electrophoretic Devices," (1998), Anal. Chem. vol. 70, pp. 2303-2310.
Schmalzing, et al., "DNA Typing in Thirty Seconds with a Microfabricated Device," (1997), Proc. Natl. Acad. Sci. USA vol. 94, pp. 10273-10278.
Schwartz, et al., "Ordered Restriction Maps of *Saccharomyces cerevisiae* Chromosomes Constructed by Optical Mapping," (1993), Science vol. 262, pp. 110-114.
Schwartz, et al., "Conformational Dynamics of Individual DNA Molecules During Gel Electrophoresis," (1989), Nature vol. 338, pp. 520-522.
Seiler et al., "Planar Glass Chips for Capillary Electrophoresis: Repetitive Sample Injection, Quantitation and Separation Efficiency," (1993), Anal. Chem. vol. 65, pp. 1481-1488.
Smith et al., "Single-Polymer Dynamics in Steady Shear Flow," (1999), Science vol. 283, pp. 1724-1727.
Smith, et al., "Response of Flexible Polymers to a Sudden Elongational Flow," (1998), Science vol. 281, pp. 1335-1340.
Smith, et al., "Direct Mechanical Measurements of the Elasticity of Single DNA Molecules by Using Magnetic Beads," (1992), Science vol. 258, pp. 1122-1126.
Smith, et al., "Observation of Individual DNA Molecules Undergoing Gel Electrophoresis," (1989), Science vol. 243, pp. 203-206.
Tan, et al., "Nanoscale Imaging and Sensing by Near-Field Optics, in: *Fluroescence Imaging: Spectroscopy and Microscopy*," (1996), Wang and Herman eds., Chem. Anal. Series vol. 137, pp. 407-475.
Volkmuth, et al., "DNA Electrodiffusion in a 2D Array of Posts," (1994), Phys. Rev. Lett. vol. 72, pp. 2117-2120.
Volkmuth, et al., "DNA Electrophoresis in Microlithographic Arrays," (1992), Nature vol. 358, pp. 600-602.
Washizu, et al., "Applications of Electrostatic Stretch-and-Positioning of DNA," (1995). IEEE Trans. Industry Applications vol. 31, pp. 447-456.
Washizu, et al., "Electrostatic Manipulation of DNA in Microfabricated Structures," (1990), IEEE Trans. Industry Applications vol. 26, pp. 1165-1172.
Woolley, et al., "Ultra-high Speed DNA Fragment Separations Using Microfabricated Capillary Array Electrophoresis Chips," (1994), Proc. Natl. Acad. Sci. USA vol. 91, pp. 11348-11352.
Zimmerman, et al., "DNA Stretching on Functionalized Gold Surface," (1994), Nucl. Acids Res. vol. 22. pp. 492-497.
Nie et al., Probing individual molecules with confocal fluorescence microscopy. Science. Nov. 11, 1994;266(5187):1018-21.
Shera et al., Detection of single fluorescent molecules. Chem Phys Letts. 1990; 174(6): 553-7.
Castro et al., Single-Molecule Electrophoresis: Applications to Biomolecular Detection. SPIE. 1995; 2396:79-85.
Ekstrøm et al., Two-point fluorescence detection and automated fraction collection applied to constant denaturant capillary electrophoresis. Biotechniques. Sep. 2000;29(3):582-4, 586-9.
Shortreed et al., High-throughput single-molecule DNA screening based on electrophoresis. Anal Chem. Jul. 1, 2000;72(13):2879-85.
Ambrose et al., Application of single molecule detection to DNA sequencing and sizing, Ber. Bunsenges. Phys. Chem. 1993;97:1535-1542.
Bello et al, Electroosmosis of polymer solutions in fused silica capillaries. Electrophoresis. May 1994;15(5):623-6.
Bezrukov et al., Counting polymers moving through a single ion channel. Nature. Jul. 28, 1994;370(6487):279-81.
Boone et al., Plastic advances microfluidic devices. Anal Chem. Feb. 1, 2002;74(3):78A-86A.
Burns et al., An integrated nanoliter DNA analysis device. Science. Oct. 16, 1998;282(5388):484-7. (Abstract Only).

Bustamante et al., Direct observation and manipulation of single DNA molecules using fluorescence microscopy. Annu Rev Biophys Biophys Chem. 1991;20:415-46.

Chan et al., DNA mapping technology based on microfluidic stretching and single-molecule detection of motif tags. Biophys J. 2003;84:302A. Poster 1470. Board #B725.

Chan et al., DNA mapping using microfluidic stretching and single-molecule detection of fluorescent site-specific tags. Genome Res. Jun. 2004;14(6):1137-46.

Cheek et al., Chemiluminescence detection for hybridization assays on the flow-thru chip, a three-dimensional microchannel biochip. Anal Chem. Dec. 15, 2001;73(24):5777-83.

Chen et al., Single-Molecule Detection in Capillary Electrophoresis: Molecular Shot Noise as a Fundamental Limit to Chemical Analysis. Anal. Chem. Feb. 15, 1996;68(4):690-6.

Church et al., Multiplex DNA sequencing. Science. Apr. 8, 1988;240(4849):185-8.

D'Antoni et al., Single Molecule Detection of Proteins Using Microfluidic Fluorescence Detection. ORC Poster. Apr. 2006.

Davis et al., Rapid DNA Sequencing Based on Single-Molecule Detection. Los Alamos Science. 1992; 20:280-6.

Foquet et al., DNA fragment sizing by single molecule detection in submicrometer-sized closed fluidic channels. Anal Chem. Mar. 15, 2002;74(6):1415-22. (Abstract Only).

Goodwin et al., Spatial dependence of the optical collection efficiency in flow cytometry. Cytometry. Oct. 1, 1995;21(2):133-44.

Gurrieri et al., Imaging of kinked configurations of DNA molecules undergoing orthogonal field alternating gel electrophoresis by fluorescence microscopy. Biochemistry. Apr. 3, 1990;29(13):3396-401. (Abstract Only).

Gurrieri et al., Purification and staining of intact yeast DNA chromosomes and real-time observation of their migration during gel electrophoresis. Biochem J. Aug. 15, 1997;326 ( Pt 1):131-8.

Haab et al., Single molecule fluorescence burst detection of DNA fragments separated by capillary electrophoresis. Anal Chem. Sep. 15, 1995;67(18):3253-60.

Han et al., Separation of long DNA molecules in a microfabricated entropic trap array. Science. May 12, 2000;288(5468):1026-9.

Harding et al., Single-molecule detection as an approach to rapid DNA sequencing. Trends Biotechnol. Jan.-Feb. 1992;10(1-2):55-7.

Herrick et al., Single molecule analysis of DNA replication. Biochimie. Aug.-Sep. 1999;81(8-9):859-71.

Holzwarth, The acceleration of linear DNA during pulsed-field gel electrophoresis. Biopolymers. Jun. 1989;28(6):1043-58.

Holzwarth et al., Transient orientation of linear DNA molecules during pulsed field gel electrophoresis. Nucleic Acids Res. Dec. 10, 1987;15(23):10031-44.

Kasianowicz et al., Characterization of individual polynucleotide molecules using a membrane channel. Proc Natl Acad Sci U S A. Nov. 26, 1996;93(24):13770-3.

Kasianowicz et al., Polymer transport in the alpha-hemolysin ion channel. Page 111. Abstract 26.

Larson et al., Single DNA molecule stretching in sudden mixed shear and elongational microflows. Lab Chip. 2006;6(9):1187-1199.

Lee et al., Diffusion of a polymer chain through a thin membrane. J Phys II France, Feb. 1996; 6:195-204.

Lee et al., Laser-induced fluorescence detection of a single molecule in a capillary. Anal Chem. Dec. 1, 1994;66(23):4142-9.

Lee et al., Micro flow cytometers with buried SU-8/SOG optical waveguides. Sensors and Actuators. 2003;103:165-70.

Nguyen et al., Detection of Single Molecules of Phycoerythrin in Hydrodynamically Focused Flows by Laser-Induced Fluorescence. Anal. Chem.,Sep. 1, 1987; 59:2158-61. (Abstract Only).

Oana et al., Visualization of a specific sequence on a single large DNA molecule using fluorescence microscopy based on a new DNA-stretching method. Biochem Biophys Res Commun. Nov. 1999;265(1):140-3.

Phillips et al., Application of single molecule technology to rapidly map long DNA and study the confirmation of stretched DNA. Nuc Acids Res. 2005;33(18):5829-5837.

Rampino et al., Apparatus for gel electrophoresis with continuous monitoring of individual DNA molecules by video epifluorescence microscopy. Anal Biochem. May 1, 1991;194(2):278-83.

Roulet et al., Fabrication of multilayer systems combining microfluidic and microoptical elements for fluorescence detection. J Micro Systms. Dec. 2001;10(4):482-91.

Roulet et al., Performance of an integrated microoptical system for fluorescence detection in microfluidic systems. Anal Chem. Jul. 15, 2002;74(14):3400-7.

Soper et al., Nanoliter-scale sample preparation methods directly coupled to polymethylmethacrylate-based microchips and gel-filled capillaries for the analysis of oligonucleotides. J. of Chroma. A. 1999; 853:107-20.

Wabuyele et al., Single molecule detection of double-stranded DNA in poly(methylmethacrylate) and polycarbonate microfluidic devices. Electrophoresis. Oct. 2001;22(18):3939-48. (Abstract Only).

Wang et al., Rapid sizing of short tandem repeat alleles using capillary array electrophoresis and energy-transfer fluorescent primers. Anal. Chem. 1995;67:1197-203.

Wang, Y. et al., High-resolution capillary array electrophoretic sizing of multiplexed short tandem repeat loci using energy-transfer fluorescent primers. Electrophoresis. 1996;17:1485-1490.

Watson et al., The early fluidic and optical physics of cytometry. Cytometry. Feb. 15, 1999;38(1):2-14.

Whitesides et al., Fabrication of Complex, 3D Microstructures. Harvard MRSEC—Research Nuggets. Materials Research Science and Engineering Center. 2 pages.

Whitesides et al., Flexible Methods for Microfluidics: Devices for handling nanoliter qualities of fluids are creating new fabrication challenges and finding new applications in biology, chemistry, and materials science. Physics Today Online. Jun. 2001, 8 pages.

Whitesides et al., Generating Microgradients. Harvard MRSEC—Research Nuggets. Materials Research Science and Engineering Center. Feb. 2, 2001. 1 page.

Whitesides et al., Three-Dimensional Networks of Fluid Channels in PDMS. Harvard MRSEC—Research Nuggets. Materials Research Science and Engineering Center. Jun. 1, 2000. 1 page.

Wilding, et al., Manipulation and flow of biological fluids in straight channels micromachined in silicon. Clin. Chem. 1994;40(1): 43-47. (Abstract Only).

Wong et al., Deformation of DNA molecules by hydrodynamic focusing. J Fluid Mech. 2003;497:55-65.

Wong et al., Direct Manipulation of DNA Molecules Using Hydrodynamic Force. 2002 IEE International Conference on Robotics and Automation. Washington, D.C. May 12, 2002.

[No Author Listed] Figure 5. Physics Today Online. Available at http://www.physicstoday.org/pt/vol-54/iss-6/captions/p42cap5. html. Last accessed Jul. 15, 2002. 2 pages.

[No Author Listed] Fraen FLP Series Lenses for Luxeon LEDs: Luxeon I, III, and V, Star and Emitter. Jan. 4, 2005. Available at http://www.fraensrl.com/images/FLP_Lens_Series_Datasheet. pdf. 8 pages.

Agronskaia et al. Two-color fluorescence in flow cytometry DNA sizing: Identification of single-molecule fluorescent probes. Anal. Chem. 1999;71:4684-4689. Abstract Only.

Ashworth et al., Transducer mechanisms for optical biosensors. Part 2: Transducer design. Comput Methods Programs Biomed. Sep. 1989;30(1):21-31.

Cova et al., Evolution and prospects for single-photon avalanche diodes and quenching circuits. J Mod Opt. Jun.-Jul. 2004;51(9-10):1267-88.

Dittrich et al., Sorting of cells and single particles in microstructures. Biophys J. 2002;82:43a. 209—Pos. Board # B70.

Giddings et al., Chapter 1. The Field-Flow Fractionation Family: Underlying Principles. In: Field-Flow Fractionation Handbook. Wiley-Interscience. 2000: 3-30.

Jo et al., A single-molecule barcoding system using nanoslits for DNA analysis. Proc Natl Acad Sci U S A. Feb. 20, 2007;104(8):2673-8. Epub Feb. 12, 2007.

Kartha et al., Laser-excited fluorescene of $Nd^{3+}$ in some fluoride crystals. Spectrochimica Acta Part A: Molecular Spectroscopy. 1987;43(7):911-15. Abstract Only.

Krogmeier et al., A Microfluidic Device for Concentrating High Molecular Weight DNA. Mar. 2, 2009; 315a. 1608 Pos. Board B452. Abstract.

Kwok et al., An Integrated Multifunction Lab-on-a-Chip Platform for Hugh Throughput Optical Mapping for DNA. Nanotechnology. 2009;48a. 244—Pos. Board B123. Abstract.

Lee et al., Analysis of self-assembled cationic lipid-DNA gene carrier complexes using flow field-flow fractionation and light scattering. Anal Chem. Feb. 15, 2001;73(4):837-43.

Lee et al., Mircomachined pre-focused $M \times N$ flow switches for continuous multi-sample injection, J Micromech Microeng. 2001;11:654-661.

Li et al., Chapter 28. Protein Complexes and Lipoproteins. In: Field Flow Fractionation Handbook. Wiley-Interscience. 2000: 433-470.

Meltzer et al., A lab-on-chip for biothreat detection using single-molecule DNA mapping. Lab Chip. Mar. 7, 2011;11(5):863-73. Epub Jan. 20, 2011.

Michalet et al., Dynamic molecular combing: stretching the whole human genome for high-resolution studies. Science, 1997;277(5331):1518-1523.

Papkov et al., A single-molecule system for detection and quantification of proteins with robust capture units and potential for high multiplexing. Biophysical Society $53^{rd}$ Annual Meeting. Feb. 28-Mar. 4, 2009. Boston. Poster.

Perkins et al., Single Polymer Dynamics in an Elongational Flow. Science 1997;276:2016-2021.

Perkins et al., Stretching of a Single Tethered Polymer in a Uniform Flow. Science. 1995;268: 83-87.

Protozanova et al., Binding Specificity of Multi-Labeled PNA Probes Studied by Single Molecule Mapping. Biophysical Society 53rd Annual Meeting. Feb. 28- Mar. 4, 2009. Boston. 25a. 124—Pos. Board B3. Abstact.

Protozanova et al., Fast high-resolution mapping of long fragments of genomic DNA based on single-molecule detection. Anal Biochem. Jul. 1, 2010;402(1):83-90. Epub Mar. 20, 2010.

Protozanova et al., Fast high-resolution mapping of long fragments of genomic DNA based on single-molecule detection. Anal Biochem. Jul. 1, 2010;402(1):83-90. Epub Mar. 20, 2010. Supplemental Data.

Radcliff et al., Chapter 1. Basics of flow cytometry. In: Methods Mol Biol. 1998;91:1-24.

Rouzina et al., Force-induced melting of the DNA double helix. Biophys J. Feb. 2001;80:894-900.

Schäfer et al., Single molecule DNA restriction in the light microscope. Single Mol. 2000;1(1):33-40.

Smith et al., Molecular Engineering of the *Autographa californica* Nuclear Polyhedrosis Virus Genome: Deletion Mutations Within the Polyhedrin Gene. J Virol. May 1983;46(2):584-93.

Smith et al., Physical Analysis of *Autographa californica* Nuclear Polyhedrosis Virus Transcripts for Polyhedrin and 10,000-Molecular-Weight Protein. J Virol. Jan. 1983;45(1):215-25.

Son et al., A platform for ultrasensitive and selective multiplexed marker protein assay toward early-stage cancer diagnosis. Nanomedicine (Lond). Feb. 2007;2(1):79-82.

Soper et al., Nanoliter-scale sample preparation methods directly coupled to polymethylmethacrylate-based microchips and gel-filled capillaries for the analysis of oligonucleotides. J Chromatography A. 1999;853:107-20.

Sturm et al., Direct observation of DNA chain orientation and relaxation by electric birefringence: implications for the mechanism of separation during pulsed-field gel electrophoresis. Phys Rev Lett. 1989;62(13):1484-87.

Thaxton et al., 19. DNA—Gold-Nanoparticle Conjugates. Nanotechnology. 2004:288-307.

Wahlund et al., Application of an asymmetrical flow field-flow fractionation channel to the separation and characterization of proteins, plasmids, plasmid fragments, polysaccharides and unicellular algae. J Chromatogr. Jan. 6, 1989;461:73-87.

White et al., *Staphylococcus aureus* strain typing by single-molecule DNA mapping in fluidic microchips with fluorescent tags. Clin Chem. Dec. 2009;55(12):2121-9. Epub Oct. 8, 2009.

White et al., *Staphylococcus aureus* strain typing by single-molecule DNA mapping in fluidic microchips with fluorescent tags. Clin Chem. Dec. 2009;55(12):2121-9. Epub Oct. 8, 2009. Supplemental Data.

Whitesides et al., Generating Microgradients. Harvard MRSEC—Research Nuggets. Materials Research Science and Engineering Center. Feb. 2, 2001. Available at http://www.mrsec.harvard.edu/research/nugget_4.html. Last accessed Jul. 15, 2002. 1 page.

Whitesides, Fabrication of Complex, 3D Microstructures. Harvard MRSEC—Research Nuggets. Materials Research Science and Engineering Center. Available at http://www.mrsec.harvard.edu/research/nugget_3.html. Last accessed Jul. 15, 2022. 1 page.

Whitesides, Three-Dimensional Networks of Fluid Channels in PDMS. Harvard MRSEC—Research Nuggets. Materials Research Science and Engineering Center. Jun. 1, 2000. Available at http://www.mrsec.harvard.edu/research/nugget_11.html. Last accessed Jul. 15, 2002. 1 page.

Wuite et al., Single-molecule studies of the effect of template tension on T7 DNA polymerase activity. Nature. Mar. 2, 2000;404(6773):103-6.

Griffis et al., High-throughput genome scanning in constant tension fluidic funnels. Lab Chip. Jan. 21, 2013;13(2):240-51. doi: 10.1039/c21c40943g. Epub Dec. 3, 2012. Supplemental Data Included. 8 pgs.

Meltzer, Single-molecule DNA mapping for pathogen detection. The Botulinum J. 2012;2(2):159-163.

U.S. Appl. No. 11/484,330, filed Jul. 11, 2006, Yantz et al.
U.S. Appl. No. 11/486,446, filed Jul. 13, 2006, Yantz et al.
U.S. Appl. No. 11/634,412, filed Dec. 6, 2006, Gilmanshin.
U.S. Appl. No. 11/698,794, filed Jan. 26, 2007, Chan et al.
U.S. Appl. No. 10/974,002, filed Oct. 25, 2004, Larson.
U.S. Appl. No. 11/180,980, filed Jul. 13, 2005, Lee et al.
U.S. Appl. No. 11/210,111, filed Aug. 23, 2005, Randall et al.
U.S. Appl. No. 11/250,179, filed Oct. 13, 2005, Larson et al.
U.S. Appl. No. 11/253,051, filed Oct. 18, 2005, Nilsen et al.
U.S. Appl. No. 11/286,714, filed Nov. 23, 2005, Nadel et al.
U.S. Appl. No. 11/311,696, filed Dec. 19, 2005, Larson et al.
U.S. Appl. No. 11/364,856, filed Feb. 27, 2006, White et al.

* cited by examiner

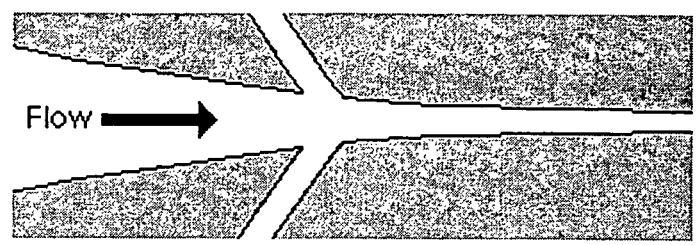
FIG. 8
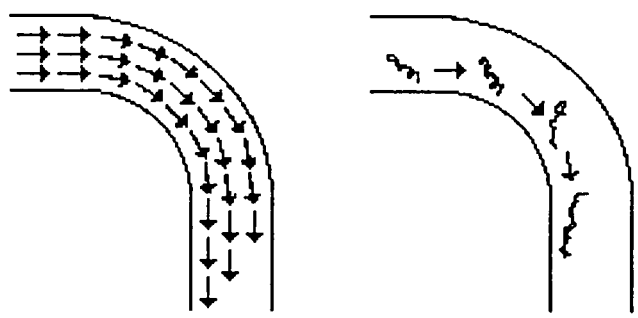
FIG. 9(a)      FIG. 9(b)

METHODS AND APPARATUSES FOR STRETCHING POLYMERS

RELATED APPLICATIONS

This application is a continuation of co-pending U.S. patent application Ser. No. 09/636,793, filed Aug. 11, 2000, which claims the benefit of U.S. Provisional Application No. 60/149,020, filed Aug. 13, 1999, which are incorporated herein by reference in their entirety.

1. FIELD OF THE INVENTION

The present invention relates to the general field of polymer characterization. More particularly, the invention relates to the use of structures to stretch a polymer or to select a polymer on the basis of length in a chip.

2. BACKGROUND OF THE INVENTION

Macromolecules are involved in diverse and essential functions in living systems. The ability to decipher the functions, dynamics, and interactions of macromolecules is dependent upon an understanding of their chemical and three-dimensional structures. These three aspects—chemical and three-dimensional structures and dynamics—are interrelated. For example, the chemical composition of a protein, and more particularly the linear arrangement of amino acids, explicitly determines the three-dimensional structure into which the polypeptide chain folds after biosynthesis (Kim & Baldwin (1990) Ann. Rev. Biochem. 59: 631-660), which in turn determines the interactions that the protein will have with other macromolecules, and the relative mobilities of domains that allow the protein to function properly.

Biological macromolecules are either polymers or complexes of polymers. Different types of macromolecules are composed of different types of monomers, i.e., twenty amino acids in the case of proteins and four major nucleobases in the case of nucleic acids. A wealth of information can be obtained from a determination of the linear, or primary, sequence of the monomers in a polymer chain. For example, by determining the primary sequence of a nucleic acid, it is possible to determine the primary sequences of proteins encoded by the nucleic acid, to generate expression maps for the determination of mRNA expression patterns, to determine protein expression patterns, and to understand how mutations in genes correspond to a disease state. Furthermore, the characteristic pattern of distribution of specific nucleobase sequences along a particular DNA polymer can be used to unequivocally identify the DNA, as in forensic analysis. To this end, fast, accurate and inexpensive methods of characterizing polymers, and particularly nucleic acids, are being developed as a result of the endeavor of the Human Genome Project to sequence the human genome.

A challenge to the characterization of the linear sequence of monomers in a polymer chain has come from the natural tendency of polymers in most media to adopt unpredictable, coiled conformations. The average amount of such coiling is dependent on the interaction of the polymer with the surrounding solution, the rigidity of the polymer, and the energy of interaction of the polymer with itself. In most cases, the coiling is quite significant. For example, a λ-phage DNA, theoretically 16 µm long when stretched out so that the DNA is in the B conformation, has a random coil diameter of approximately 1 µm (Smith et al. (1989) Science 243:203-206).

DNA and many other biopolymers can be modeled as uniform elastic rods in a worm-like chain in order to determine their random coil properties (Austin et al. (1997) Physics Today 50(2):32-38). One relevant parameter is the persistence length, P, the length over which directionality is maintained, which is given by:

$$P = \kappa/k_B T \quad (1)$$

where κ is the elastic bending modulus (Houseal et al. (1989) Biophys. J. 56:507-516), $k_B$ is the Boltzmann constant, and T is temperature (Austin et al. (1997) Physics Today 50(2):32-38). A longer persistence length means that the polymer is more rigid and more extended. Under physiological conditions, P=50 nm for DNA. While larger than the molecular diameter of 2.5 nm, the persistence length is many orders of magnitude smaller than the actual length of a typical DNA molecule such as a human chromosome, which is about 50 mm long. From the persistence length, the overall coil size, R, can be calculated (Austin et al. (1997) Physics Today 50(2):32-38) as follows:

$$\langle R^2 \rangle = 2PL \quad (2)$$

where L is the contour length of the DNA molecule. In the case of chromosomal DNA, R=70 µm. Clearly, it is much easier to analyze information on an extended piece of DNA that is 5 cm long than on a piece of DNA that has a coil size of 70 µm.

The force necessary to stretch polymers such as DNA is not very large. The worm-like chain model allows the polymer to be considered to be like a spring, and the force ($F_s$) needed to extend it close to its full natural length can be calculated (Austin et al. (1997) Physics Today 50(2):32-38) as follows:

$$F_s \approx k_B T/P \quad (3)$$

where all of the parameters are defined as above. Below $F_s$, the relationship between the force applied and the amount of stretching is roughly linear; above $F_s$, applying more force results in little change in the stretching (Smith et al. (1992) Science 258:1122-1126; Bustamante (1994) Science 265:1599-1600). Hence, full stretching is essentially attained by applying $F_s$. In the case of DNA, the force required to stretch it from its coiled conformation to its full length, which stretched conformation retains the B conformation is about 0.1 pN. Such a small force could, in principle, be obtained from virtually any source, including shear forces, electrical forces, and gravitational forces.

The danger in stretching DNA comes not in breaking the covalent bonds, which requires at least 1 nN of force (Grandbois et al. (1999) Science 283:1727-1730), but in overstretching. It has been observed that, when 70 pN of force is applied, DNA adopts a super-relaxed form, called "S-DNA", having nearly twice the length of normal B-form DNA having the same number of base pairs (Austin et al. (1997) Physics Today 50(2):32-38). Others have reported this transition at a force of 50 pN (Marko & Siggia (1995) Macromolecules 28:8759-8770). The length of S-DNA is less consistent than that of B-DNA stretched to its natural length and is more dependent on the exact force applied (Cluzel et al. (1996) Science 271:792-794), varying linearly with applied force from 1.7 to 2.1 times the length of B-DNA. Since it may not be possible to know the exact force applied, it is desirable to avoid stretching DNA into its S-form. Therefore, a force having a range of about two orders of magnitude, from about 0.1 pN to 25 pN, is capable of consistent and predictable stretching of DNA to its fully extended B-form.

In addition, the force must be applied fast enough to keep the polymer from recoiling. The natural relaxation time of a polymer, r, depends on the solvent, as follows (Marko (1998) Physical Review E 27:2134-2149):

$$\tau \approx L^2 P \mu / k_B T \tag{4}$$

where μ is the viscosity of the solvent and the other parameters are as defined above. In the case of DNA at physiological conditions, the relaxation time is about 6 seconds, which can be increased to 20 seconds in a solution with a viscosity of 220 cp (Smith et al. (1999) Science 283:1724-1727) or by running the DNA in a confined space to lengthen P and change the viscous drag (Bakajin et al. (1998) Phys. Rev. Let. 80:2737-2740). Relaxation time is also a function of the extent of stretching (Hatfield & Quake (1999) Phys. Rev. Let. 82:3548-3551), so the values calculated above are a lower bound on the actual relaxation time.

Regardless of the exact value of the relaxation time, the polymer must be stretched out on a shorter time scale. In the case of flow through a channel, in which the stretching comes from fluid strain on the polymer, the appropriate time scale for stretching is the reciprocal of the strain rate. The strain rate is defined as $d\epsilon/dt = dv_x/dx$, where x is the flow direction and $v_x$ is the x-component of the velocity. The multiple of the strain rate and the relaxation time is known as the Deborah number, $De=\tau d\epsilon/dt$, and can be used to determine whether the stretching will be maintained (Smith & Chu (1998) Science 281: 1335-1340). If De is much greater than one, then the strain force predominates and the polymer will remain stretched. If De is much smaller than one, then the natural relaxation process dominates and the polymer will not remain stretched. When other stretching forces are involved, dimensionless values can be derived from other appropriate time scales, such as the Weissenberg number in extensional flow (Smith et al. (1999) Science 283:1724-1727).

Previous techniques used to stretch DNA involved immobilization of at least one end of the molecule on a surface, followed by manipulation of the other end, stretching with physical forces followed by immobilization, or running through a gel with constricted dimensions. Early attempts to stretch DNA for size measurement were conducted by Houseal et al. (1989, Biophys. J. 56:507-516). Contacting a DNA solution with a gold surface resulted in satisfactory binding, but use of the Kleinschmidt procedure, which is used extensively in electron microscopy to spread DNA molecules on a protein monolayer, resulted in a number of molecules remaining coiled instead of being stretched. Another attempt was made to stretch DNA by "gently" smearing it using a pipettor, a technique that is difficult to automate (PCT Publication No. WO 93/22463).

More sophisticated schemes have been devised for the immobilization of one end of DNA and other polymers on surfaces. In general, they involve the modification of a surface to expose reactive groups such as hydroxyl, amine, thiol, aldehyde, ketone, or carboxyl groups, or to attach such coupling structures as avidin, streptavidin, and biotin. Examples of these techniques are found in PCT Publication No. 97/06278; U.S. Pat. No. 5,846,724; and Zimmermann & Cox (1994) Nucl. Acids Res. 22:492-497. Often, these techniques involve the use of a silane (Bensimon et al. (1994) Science 265:2096-2098).

Once the polymer is immobilized on one end, stretching is possible since the forces may be aligned perpendicular to the attachment surface. One common method is to use a receding meniscus to align the polymer, a process sometimes referred to as "molecular combing." In this technique, a second fluid is introduced that is substantially immiscible with the first, forming a meniscus at the interface. The original fluid is then gradually removed by mechanical, thermal, electrical, or chemical means or simply by evaporation and is replaced by the new fluid. As the interface moves, the polymer is aligned perpendicular to the interface by surface tension and therefore, becomes stretched. The force of stretching by this method is expressed as a function of the diameter D of the polymer (D=2.2 nm for double-stranded DNA) and the surface tension γ (Bensimon et al. (1994) Science 265:2096-2098): $F=\gamma \pi D$.

With an air/water interface, γ is 0.07 N/m, giving a force of about 40 pN for DNA, which is clearly in the desired range. If the second fluid is properly chosen to discourage polymer movement, the polymer remains fixed in place indefinitely. Furthermore, adjacent polymers attached to the same surface all become aligned in the same direction. The two fluids involved, while often solvents of the polymer, can be only partial solvents and one can even be air. The degree of stretching is dependent on the modification of the surface (Bensimon, D. et al. (1995) Phys. Rev. Lett. 74(23):4754-4747), but is consistent for any given surface treatment. Variations of this technique have been employed (U.S. Pat. No. 5,851,769; PCT Publication No. WO 97/06278; Bensimon et al. (1994) Science 265:2096-2098; U.S. Pat. No. 5,840,862; Cox & Zimmermann (1994) Nucl. Acids Res. 22:492-497). Nevertheless, this technique cannot be easily adapted to a high-throughput operation, since the immobilization is a rate-limiting step and further modification of the polymer is more difficult after the immobilization.

An alternative way to manipulate DNA immobilized at one end involves the use of an optical trap. In this technique, a laser beam ("optical tweezers") imparts momentum to a DNA molecule through emitted photons. By shifting the position of the photons, i.e., moving the beam, an extremely precise change can be induced in the direction of travel of the DNA (U.S. Pat. No. 5,079,169; Chu (1991) Science 253:861-866). Hence, a DNA molecule can be stretched using optical tweezers. The technique offers the advantage of being able to vary the force used for stretching and has been used to verify reptation theory (Perkins et al. (1994) Science 264:819-822). However, the laser can only hold one molecule in place at a time and has to be realigned for each subsequent molecule, making it unattractive for high-throughput analyses.

A third method of stretching DNA involves electrophoresis of either a DNA immobilized at one end to move the unattached end of the molecule away from the fixed end and subsequently attaching the fixed end to a surface with avidin, or a DNA unattached at both ends and then attaching both ends to a surface with avidin (Kabata et al. (1993) Science 262:1561-1563; Zimmerman & Cox (1994) Nucl. Acids Res. 22:492-497). No attempt was made to characterize the quality of the stretching using this technique. Furthermore, this technique shares the disadvantages of the previously-mentioned techniques (with respect to post-immobilization processing).

DNA has also been stretched by electrophoresis without fixing one end of the molecule. As part of a near-field detection scheme for sequencing biomolecules, DNA has been elongated by electrophoresis both in a gel and in solution, using electrical forces to move the DNA in position for reading (U.S. Pat. No. 5,538,898). However, no data were given to determine the quality of the stretching of large polymers, and the technique is limited to analyzing approximately 3 megabases at a time.

An extension of this idea involves the use of dielectrophoresis, or a field of alternating current, to stretch DNA. Washizu and Kurosawa ((1990) IEEE Transactions on Industry Applications 26:1165-1172) have demonstrated that DNA will stretch to its full length in its B-DNA form in a field having strength $10^6$ V/m and a frequency of 400 kHz or more.

At certain lower frequencies (around 10 kHz), the DNA will also stretch fully, but in a direction perpendicular to the field rather than parallel to it. This technology has been applied to sizing DNA by creating a gap with a tapered width between electrodes such that the DNA will align where the gap width equals the length of the DNA. It has also been found that this technique will not stretch single-stranded DNA due to differences in solvent interactions from double stranded DNA (Washizu et al. (1995) IEEE Transactions on Industry Applications 31:447-456). One disadvantage to this technique is that, due to the presence of induced dipoles along the length of the DNA, samples agglomerate readily, and in a heterogeneous sample, it is difficult to accurately identify the components. In addition, these experiments must be performed in deionized water in order to avoid the unwanted effects of Joule heating and electro-osmotic flow, presenting a sample preparation difficulty since most DNA exists in salt solutions or other solvents.

Gravitational forces have also been used to stretch DNA (U.S. Pat. No. 5,707,797; Windle (1993) Nature Genetics 5:17-21). In this technique, drops of DNA from the sodium dodecyl sulfate lysing of cells were allowed to run down a slide held at an angle. The effect of gravity was enough to stretch out the DNA, even to its over-stretched S-DNA form. The DNA was then immobilized on the slide, making processing, e.g., fluorescent labeling, prior to stretching relatively difficult.

Church et al. have developed another method for polymer characterization that involves measuring physical changes at an interface between two pools of media as a polymer traverses that interface (U.S. Pat. No. 5,795,782). This method is relatively inflexible. For example, the ion channel embodiment for nucleic acid characterization (Church et al. (1999) Science 284:1754-1756) works only for single stranded DNA. An interface usable for a wide variety of polymers has yet to be developed.

A method for measuring the length of DNA was developed by Kambara et al. (U.S. Pat. No. 5,356,776). This method involves electrophoresis of DNA through a gel; when the DNA reaches a portion of the gel no more than a few microns in diameter, it is forced into a straight line, where detection of fluorescent labels on each end of the DNA is accomplished. In another embodiment, the DNA is immobilized on one end in an aperture, stretched by electrophoresis, and a label on the other end of the molecule is detected. The use of a gel in this method necessitates a higher voltage than in solution to move DNA, and the end labeling precludes most other characterization of the DNA. In addition, long DNA molecules tend to become entangled in a gel. A modification of electrophoresis procedures, known as pulsed-field electrophoresis (Schwartz & Koval (1989) Nature 338:520-522), allows the full stretching of longer pieces of DNA by moving the electric field. However, this technique takes a substantially longer time to run because of the field variation and shares the other disadvantages of electrophoresis.

A hybrid of gel based and solution methods for stretching DNA was developed by Schwartz et al. ((1993) Science 262: 110-113). DNA was placed in a free molten agarose solution, stretched by gravity, and then fixed in place by the gelling process. An enzyme was also added during gelling to cut the DNA at specific sites. This method is effective in creating restriction maps, however, predictable stretching in an agarose medium is difficult and the adaptation of the technique to high-throughput methods of analyzing uncut DNA is problematic.

Other techniques for characterizing particles do not rely on stretching. For example, a method developed by Schwartz (U.S. Pat. No. 5,599,664; EP 0391674) allows sizing and massing by subjecting a particle to a force and measuring conformational and positional changes. In the case of polymers, the force is usually applied to a coiled conformation. Another method for sizing and sorting DNA molecules (Chou et al. (1999) Proc. Natl. Acad. Sci. USA 96:11-13) involves a device that operates on a micron scale. The device uses the integral fluorescence signal from coiled DNA passing a detector to conduct the analysis. Schmalzing et al. ((1998) Analytical Chemistry 70:2303-2310; (1997) Proc. Natl. Acad. Sci. USA 94:10273-10278) developed microfabricated devices for DNA analysis, including sequencing which employ small-scale versions of traditional techniques, such as electrophoresis, and do not rely on DNA stretching.

In order to accurately determine the linear sequence of information in biopolymers, it is necessary to stretch the biopolymer so that individual units are distinguishable. Although many techniques have been developed that stretch biopolymers, and particularly DNA, they all have drawbacks, such as uniformity and reproducibility of stretching, ease of handling the biopolymer, and applicability to all types and sizes of biopolymers. Furthermore, none of them are applicable to rapid analysis of information, such as is necessary to sequence large pieces of DNA on a reasonable time scale. Clearly, there is a need for methods and apparatuses for reliably stretching polymers such that the linear sequence of information therein can be determined more rapidly and accurately in order to elucidate complex genetic function and diagnose diseases and genetic dysfunctions.

Citation of a reference herein shall not be construed as indicating that such reference is prior art to the present invention.

3. SUMMARY OF THE INVENTION

In a first embodiment, the present invention relates to an integrated apparatus for stretching at least one polymer in a fluid sample comprising an elongation structure, wherein said elongation structure comprises a tapered channel, said tapered channel decreasing linearly in width from a first end to a second end, and wherein said at least one polymer, when present, moves along said tapered channel in a direction from said first end to said second end; whereby when said at least one polymer in said fluid sample moves along said tapered channel, a shear force is applied to said at least one polymer.

This embodiment of the present invention is useful for stretching polymers, particularly DNA, for further analysis.

In a second embodiment, the present invention relates to an integrated apparatus comprising: (a) at least one polymer in a fluid sample; and (b) an elongation structure for stretching said at least one polymer, wherein said elongation structure comprises a tapered channel, said tapered channel decreasing linearly in width from a first end to a second end, and wherein said at least one polymer, when present, moves along said tapered channel in a direction from said first end to said second end, whereby when said at least one polymer in said fluid sample moves along said tapered channel, a shear force is applied to said at least one polymer.

In a third embodiment, the present invention relates to an integrated apparatus for stretching at least one polymer in a fluid sample comprising an elongation structure, wherein said elongation structure comprises a tapered channel, said tapered channel decreasing in width at a greater than linear rate from a first end to a second end, and wherein said at least one polymer, when present, moves along said tapered channel in a direction from said first end to said second end; whereby when said at least one polymer in said fluid sample moves along said tapered channel, a shear force is applied to said at least one polymer.

This embodiment of the present invention is also useful for stretching polymers, particularly DNA, for further analysis.

In a fourth embodiment, the present invention relates to an integrated apparatus comprising: (a) at least one polymer in a fluid sample; and (b) an elongation structure for stretching said at least one polymer, wherein said elongation structure comprises a tapered channel, said tapered channel decreasing in width at a greater than linear rate from a first end to a second end, and wherein said at least one polymer, when present, moves along said tapered channel in a direction from said first end to said second end; whereby when said at least one polymer in said fluid sample moves along said tapered channel, a shear force is applied to said at least one polymer.

In a fifth embodiment, the present invention relates to an integrated apparatus for stretching at least one polymer in a fluid sample comprising an elongation structure, wherein said elongation structure comprises a tapered channel, said tapered channel decreasing in width from a first end to a second end, and wherein said at least one polymer, when present, moves along said tapered channel in a direction from said first end to said second end; whereby when said at least one polymer in said fluid sample moves along said tapered channel, a shear force is applied to said at least one polymer, wherein said shear force produces a shear rate that is constant.

This embodiment of the present invention is useful for stretching polymers, particularly DNA, for further analysis.

In a sixth embodiment, the present invention relates to an integrated apparatus comprising: (a) at least one polymer in a fluid sample; and (b) an elongation structure for stretching said at least one polymer, wherein said elongation structure comprises a tapered channel, said tapered channel decreasing in width from a first end to a second end, and wherein said at least one polymer, when present, moves along said tapered channel in a direction from said first end to said second end; whereby when said at least one polymer in said fluid sample moves along said tapered channel, a shear force is applied to said at least one polymer, wherein said shear force produces a shear rate that is constant.

In a seventh embodiment, the present invention relates to an integrated apparatus for stretching at least one polymer in a fluid sample comprising an elongation structure, wherein said elongation structure comprises a central channel for holding fluid and a plurality of side channels for holding fluid connected to said central channel; and wherein said at least one polymer, when present, moves along said central channel in an elongation direction.

This embodiment of the present invention is useful for stretching polymers, particularly DNA, for further analysis.

In an eighth embodiment, the present invention relates to an integrated apparatus for stretching at least one polymer in a fluid sample comprising: (a) an elongation structure; (b) a delivery channel leading into and out of said elongation structure for delivering said at least one polymer sample in said fluid to said elongation structure; and (c) means for causing said at least one polymer in said fluid sample, when present, to move within said elongation structure, wherein said elongation structure comprises a central channel for holding fluid and a plurality of side channels for holding fluid connected to said central channel; and wherein, when said at least one polymer is present, said means for causing causes said at least one polymer to move along said central channel in an elongation direction.

This embodiment of the present invention is useful for stretching polymers, particularly DNA, for further analysis.

In a ninth embodiment, the present invention relates to an integrated apparatus for stretching DNA in a fluid sample comprising: (a) an elongation structure; (b) means for delivering said DNA in said fluid sample to said elongation structure; and (c) means for causing said DNA in said fluid sample, when present, to move within said elongation structure, wherein said elongation structure comprises a central channel for holding fluid and a plurality of side channels for holding fluid connected to said central channel; and wherein, when said DNA is present, said means for causing causes said DNA to move along said central channel in an elongation direction.

In a tenth embodiment, the present invention relates to an integrated apparatus comprising: (a) at least one polymer in a fluid sample; (b) an elongation structure for stretching said at least one polymer, wherein said elongation structure comprises a central channel for holding fluid and a plurality of side channels for holding fluid connected to said central channel.

In an eleventh embodiment, the present invention relates to an integrated apparatus for stretching at least one polymer in a fluid sample comprising an elongation structure, wherein said elongation structure comprises a channel with at least one bend, and wherein said at least one polymer, when present, moves along said channel.

This embodiment of the present invention is useful for stretching polymers, particularly DNA, for further analysis.

In a twelfth embodiment, the present invention relates to an integrated apparatus for stretching DNA in a fluid sample comprising: (a) an elongation structure; and (b) means for delivering said DNA in said fluid sample to said elongation structure, wherein said elongation structure comprises a channel with at least one bend, and wherein said DNA, when present, moves along said channel.

In a thirteenth embodiment, the present invention relates to an integrated apparatus comprising: (a) at least one polymer in a fluid sample; and (b) an elongation structure for stretching said at least one polymer, wherein said elongation structure comprises a channel with at least one bend.

In a fourteenth embodiment, the present invention relates to an integrated apparatus for stretching at least one polymer in a fluid sample comprising an elongation structure, wherein said elongation structure comprises a tapered channel along which said at least one polymer, when present, moves in a flow direction, and wherein said channel comprises a plurality of obstacles to motion of said at least one polymer.

This embodiment of the present invention is useful for stretching polymers, particularly DNA, for further analysis.

In a fifteenth embodiment, the present invention relates to an integrated apparatus for stretching at least one polymer in a fluid sample comprising an elongation structure, wherein said elongation structure comprises a central channel along which said at least one polymer, when present, moves in a flow direction and a plurality of side channels connected to said central channel, and wherein said central channel further comprises a plurality of obstacles to motion of said at least one polymer.

In a sixteenth embodiment, the present invention relates to an integrated apparatus for stretching at least one polymer in a fluid sample comprising an elongation structure, wherein said elongation structure comprises a channel with at least one bend along which said at least one polymer, when present, moves in a flow direction, and wherein said channel comprises a plurality of obstacles to motion of said at least one polymer.

In a seventeenth embodiment, the present invention relates to an integrated apparatus for stretching at least one polymer in a fluid sample comprising an elongation structure, wherein said elongation structure comprises a channel along which said at least one polymer, when present, moves in a flow direction, and wherein said channel comprises a plurality of posts, at least one of said posts having a non-quadrilateral polygonal cross sectional shape.

The fifteenth, sixteenth and seventeenth embodiments of the present invention are useful for stretching polymers, particularly DNA, for further analysis.

In an eighteenth embodiment, the present invention relates to an integrated apparatus for stretching at least one polymer in a fluid sample comprising an elongation structure, wherein said elongation structure comprises a channel along which said at least one polymer, when present, moves in a flow direction, and wherein said channel comprises a plurality of obstacles to motion of said at least one polymer, said plurality of obstacles being positioned as a series of rows, each said row positioned perpendicular to said flow direction, and each successive row offset from a previous row, whereby at least a portion not equal to a multiple of ½ of one of said obstacles overlaps an extension of a gap formed by two adjacent obstacles in said previous row along said flow direction.

This embodiment of the present invention is useful for stretching polymers, particularly DNA, for further analysis.

In a nineteenth embodiment, the present invention relates to an integrated apparatus comprising: (a) at least one polymer in a fluid sample, every said polymer having a diameter greater than or equal to a minimum diameter; and (b) an elongation structure for stretching said at least one polymer, wherein said elongation structure comprises a channel along which said at least one polymer, when present, moves in a flow direction, and wherein said channel comprises a plurality of obstacles to motion of said at least one polymer, said plurality of obstacles positioned as a series of rows, each said row positioned perpendicular to said flow direction, and each adjacent pair of obstacles in each of said series of rows is separated by a distance greater than 50 times said minimum diameter.

This embodiment of the present invention is useful for stretching polymers, particularly DNA, for further analysis.

In a twentieth embodiment, the present invention relates to an integrated apparatus for stretching at least one polymer in a fluid sample comprising an elongation structure, wherein said elongation structure comprises a channel along which said at least one polymer, when present, moves in a flow direction, and wherein said channel comprises a plurality of obstacles to motion of said at least one polymer, said plurality of obstacles decreasing in size along said flow direction.

This embodiment of the present invention is also useful for stretching polymers, particularly DNA, for further analysis.

In a twenty-first embodiment, the present invention relates to an integrated apparatus for stretching DNA comprising an elongation structure, wherein said elongation structure comprises a tapered central channel, said tapered central channel comprising a first end and a second end, and wherein said DNA, when present, moves along said tapered central channel in a direction from said first end to said second end, wherein said elongation further comprises a plurality of side channels connected to said tapered central channel, wherein said tapered central channel comprises at least one bend; and wherein said tapered central channel comprises a plurality of obstacles to motion of said DNA.

In a twenty-second embodiment, the present invention relates to an integrated apparatus for stretching DNA comprising an elongation structure, said elongation structure comprising: (a) a first tapered channel, said first tapered channel comprising a first end, a second end, and a plurality of posts between said first end and said second end in a staggered arrangement comprising a number of rows between 12 and 15, said first tapered channel decreasing in width at an angle of 26.6°, said angle being defined at said first end with respect to a constant-width channel, said first end having a width between 0.5 and 5 µm, said posts having a cross sectional area equal to 1.5 µm² and separated by a gap equal to 0.5 µm; and (b) a second tapered channel, said second tapered channel connected to said first tapered channel at said second end and decreasing in width such that a shear force producing a constant shear rate is applied to said DNA, when present, to a width between 0.5 and 5 µm, said second tapered channel having a length between 1 and 3 mm.

In a twenty-third embodiment, the present invention relates to a method for stretching at least one polymer comprising the steps of: (a) delivering said at least one polymer to an elongation structure, said elongation structure comprising a tapered channel with a first end and a second end; and (b) moving said at least one polymer along said tapered channel from said first end to said second end, whereby said tapered channel causes a shear force that produces a constant shear rate to be applied to said at least one polymer as said at least one polymer moves along said tapered channel.

The method encompassed by this embodiment of the present invention is useful for stretching polymers, particularly DNA, for further analysis.

In a twenty-fourth embodiment, the present invention relates to a method for stretching at least one polymer comprising the steps of: (a) delivering said at least one polymer to an elongation structure, said elongation structure comprising a linearly tapered channel with a first end and a second end; and (b) moving said at least one polymer along said tapered channel from said first end to said second end.

In a twenty-fifth embodiment, the present invention relates to a method for stretching at least one polymer comprising the steps of: (a) delivering said at least one polymer to an elongation structure, said elongation structure comprising a tapered channel with a first end and a second end, said tapered channel decreasing at a greater than linear rate from said first end to said second end; and (b) moving said at least one polymer along said tapered channel from said first end to said second end.

In a twenty-sixth embodiment, the present invention relates to a method for stretching at least one polymer comprising the steps of: (a) delivering said at least one polymer to an elongation structure, said elongation structure comprising a central channel holding fluid and a plurality of side channels holding fluid connected to said central channel, said central channel comprising a first end and a second end; and (b) moving said at least one polymer along said central channel from said first end to said second end.

The methods of the twenty-fourth, twenty-fifth, and twenty-sixth embodiments of the present invention are useful for stretching polymers, particularly DNA, for further analysis.

In a twenty-seventh embodiment, the present invention relates to a method for stretching at least one polymer comprising the steps of: (a) delivering said at least one polymer to an elongation structure, said elongation structure comprising a channel with at least one bend, said channel comprising a first end and a second end; and (b) moving said at least one polymer along said channel from said first end to said second end.

The method encompassed by this embodiment of the present invention is useful for stretching polymers, particularly DNA, for further analysis.

In a twenty-eighth embodiment, the present invention relates to a method for stretching at least one polymer comprising the steps of: (a) delivering said at least one polymer to an elongation structure, said elongation structure comprising a channel and a plurality of obstacles to motion of said at least one polymer within said channel, said central channel comprising a first end and a second end; and (b) moving said at least one polymer along said channel from said first end to said second end, wherein said plurality of obstacles to motion decrease in size along a direction from said first end to said second end.

The method encompassed by this embodiment of the present invention is useful for stretching polymers, particularly DNA, for further analysis.

In a twenty-ninth embodiment, the present invention relates to a method for stretching at least one polymer comprising the steps of: (a) delivering said at least one polymer to an elongation structure, said elongation structure comprising a channel and a plurality of obstacles to motion of said at least one polymer within said channel, said central channel comprising a first end and a second end; and (b) moving said at least one polymer along said channel from said first end to said second end, wherein at least one of said obstacles has a non-quadrilateral polygonal cross-sectional shape.

The method encompassed by this embodiment of the present invention is useful for stretching polymers, particularly DNA, for further analysis.

In a thirtieth embodiment, the present invention relates to a method for stretching at least one polymer comprising the steps of: (a) delivering said at least one polymer to an elongation structure, said elongation structure comprising: (i) a tapered central channel with at least one bend, said tapered central channel comprising a first end and a second end; (ii) a plurality of side channels connected to said tapered central channel; and (iii) a plurality of obstacles to motion of said at least one polymer within said tapered central channel; and (b) moving said at least one polymer along said central channel from said first end to said second end.

The method encompassed by this embodiment of the present invention is useful for stretching polymers, particularly DNA, for further analysis.

In a thirty-first embodiment, the present invention relates to an integrated apparatus for stretching at least one polymer in a fluid sample comprising an elongation structure, wherein said elongation structure comprises a channel along which said at least one polymer, when present, moves in a flow direction, and wherein said channel comprises at least one step that decreases the depth, z, of the channel from a first end to a second end.

In a thirty-second embodiment, the present invention relates to an integrated apparatus comprising an elongation structure comprising a channel, said channel comprising at least one step that decreases the depth, z, of said channel from a first end to a second end, said channel comprising at least one polymer in a fluid sample, said channel being configured such that a shear force is applied to said at least one polymer as it moves in a direction from said first end to said second end.

In a thirty-third embodiment, the present invention relates to an integrated apparatus for stretching at least one polymer in a fluid sample comprising an elongation structure, said elongation structure comprising: (a) a first channel, said first channel comprising a first end and a second end; and (b) a second channel, said second channel comprising a third end and a fourth end, said third end being connected to said first channel at said second end, along which said at least one polymer, when present, moves in a flow direction, and wherein said first channel decreases in width from said first end to said second end at a rate different from the rate at which said second channel decreases in width from said third end to said fourth end.

In a thirty-fourth embodiment, the present invention relates to an integrated apparatus for stretching at least one polymer in a fluid sample comprising an elongation structure, said elongation structure comprising: (a) a first channel having a width equal to 10 µm and a depth equal to 1 µm, said first channel comprising a first end, a second end, and a plurality of posts between said first end and said second end in a staggered arrangement comprising between at least 12 to 15 rows, said plurality of posts terminating at said second end and each post in said plurality of posts having a cross-sectional area of between 1 µm$^2$ and 25 µm$^2$; and (b) a second channel, said second channel comprising a third end and a fourth end, said third end being connected to said first channel at said second end, said second channel decreasing in width at a rate of $1/x^2$ from said third end to said fourth end, said total width decreasing from 10 µm to 1 µm, wherein x is the distance along the length of said second channel, the length of said second channel being equal to 5 µm, said second channel comprising one step at said third end that reduces the depth of said second channel to 0.25 µm$^2$, wherein said at least one polymer, when present, moves along said first channel and said second channel in a flow direction.

In a thirty-fifty embodiment, the present invention relates to an integrated apparatus for selectively stretching at least one polymer in a fluid sample on the basis of length, comprising an elongation structure, wherein said elongation structure comprises: (a) a first channel, said first channel comprising a first end, a second end, and a plurality of posts in a staggered arrangement between said first end and said second end, each post in said plurality of posts being situated at a distance no less than L from said second end; and (b) a second channel, said second channel comprising a third end and a fourth end, said third end being connected to said first channel at said second end, said second channel decreasing in width from said third end to said fourth end, along which said at least one polymer, when present, moves in a flow direction.

In a thirty-sixth embodiment, the present invention relates to an integrated apparatus for stretching a plurality of polymers having varying lengths in a fluid sample, comprising an elongation structure, wherein said elongation structure comprises: (a) a first channel, said first channel comprising a first end and a second end; (b) a second channel, said second channel comprising a third end and a fourth end, said third end being connected to said first channel at said second end, said second channel decreasing in width from said third end to said fourth end; and (c) a plurality of posts in a staggered arrangement in said first channel and said second channel, along which said plurality of polymers, when present, move in a flow direction.

In a thirty-seventh embodiment, the present invention relates to a method for stretching at least one polymer, comprising moving said at least one polymer along an elongation structure, said elongation structure comprising a first channel, said first channel comprising a first end and a second end, and a second channel, said second channel comprising a third end and a fourth end, said third end connected to said first channel at said second end, wherein said first channel decreases in width from said first end to said second end at a rate different from the rate at which said second channel decreases in width from said third end to said fourth end.

In a thirty-eighth embodiment, the present invention relates to a method for stretching at least one polymer having a length greater than or equal to L in a fluid sample comprising moving said at least one polymer along an elongation structure, said elongation structure comprising a first channel, said first channel comprising a first end, a second end, and a plurality of posts in a staggered arrangement between said first end and said second end, each post in said plurality of posts being situated at a distance L from said second end, and a second channel, said second channel comprising a third end and a fourth end, said third end being connected to said first channel at said second end, said second channel decreasing in width from said third end to said fourth end, wherein a polymer having a length greater than or equal to L is stretched and a polymer having a length less than L is not stretched.

In a thirty-ninth embodiment, the present invention relates to a method for stretching a plurality of polymers having varying lengths in a fluid sample comprising moving said plurality of polymers along an elongation structure, said elongation structure comprising: (a) a first channel, said first channel comprising a first end and a second end; (b) a second channel, said second channel comprising a third end and a fourth end, said third end being connected to said first channel at said second end, said second channel decreasing in width from said third end to said fourth end; and (c) a plurality of posts in a staggered arrangement in said first channel and said second channel.

In a fortieth embodiment, the present invention relates to a method for stretching at least one polymer, comprising moving said at least one polymer along an elongation structure, said elongation structure comprising: (a) a first channel having a width equal to 10 µm and a depth equal to 1 µm, said first channel comprising a first end, a second end, and a plurality of posts between said first end and said second end in a staggered arrangement comprising between at least 12 to 15 rows, said plurality of posts terminating at said second end and each post in said plurality of posts having a cross-sectional area of between 1 µm² and 25 µm²; and (b) a second channel, said second channel comprising a third end and a fourth end, said third end being connected to said first channel at said second end, said second channel decreasing in width at a rate of $1/x^2$ from said third end to said fourth end, said total width decreasing from 10 µm to 1 µm, wherein x is the distance along the length of said second channel, the length of said second channel being equal to 5 µm, said second channel comprising one step at said third end that reduces the depth of said second channel to 0.25 µm².

4. BRIEF DESCRIPTION OF THE DRAWINGS

FIG. 1 shows examples of various structures that fall within the scope of the invention.

FIG. 2(a-m) shows (a) several embodiments of stretching structures involving funnels, posts, branches, and serial structures; (b) an enlarged example of two-funnel structures with posts in serial; (c) several embodiments of complex post arrangements and branched structures; (d) an embodiment of a structure containing serial and parallel structures; (e) an asymmetric branched structure; (f) an structure having a combination of small obstacles which define small gaps; (g) a structure having a combination of polygons, bars, and posts; (h) an asymmetric bent structure; (i) an enlarged view of a branched structure having posts; (j) a large funnel structure with support posts; (k) a funnel structure with posts; (l) funnel structures with a linear increase in flow rate with and without posts; and (m) a summary of some of the funnel structures encompassed by the present invention.

FIG. 8 shows an embodiment of the shear-stretching regime in which shear comes from both a narrowing channel and the presence of side channels.

FIG. 9(a) shows the "racetrack effect" of fluid on the outside of a bend taking longer to pass around the corner than fluid on the inside; (b) shows how the "racetrack effect" can lead to the uncoiling of a polymer in a bend.

Figure 10:
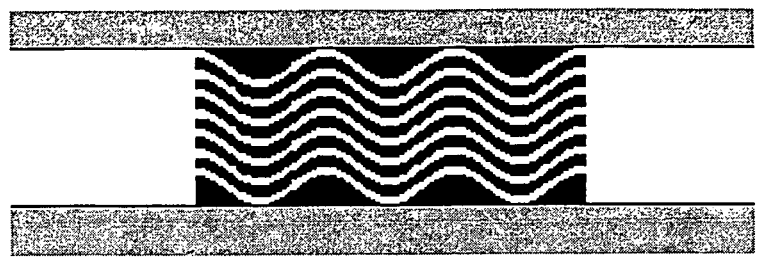

FIG. 10 displays an embodiment of the tortuosity regime, in which the channels follow a sine wave shape.

Figure 11:
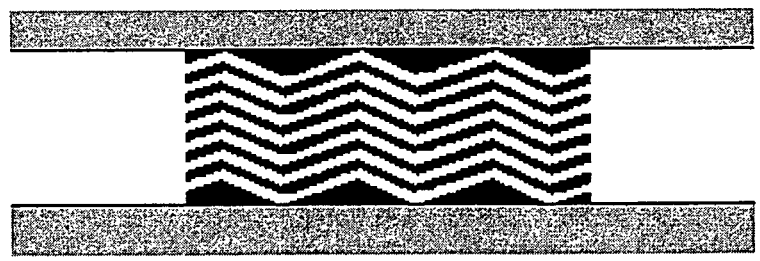

FIG. 11 displays an embodiment of the tortuosity regime in which the channels follow a zig-zag shape.

Figure 12:
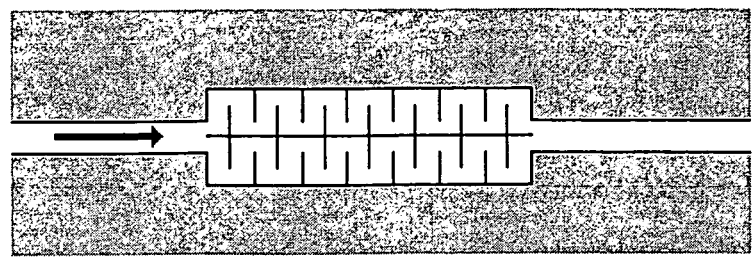

FIG. 12 displays an embodiment of the tortuosity regime in which the channels follow right angles in a "snake" shape.

Figure 13:
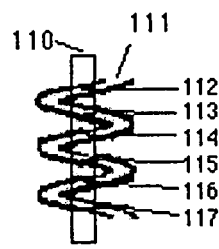

FIG. 13 shows how a tortuous channel can be used for multiple detection of the same polymer as it travels down a channel.

Figure 14:
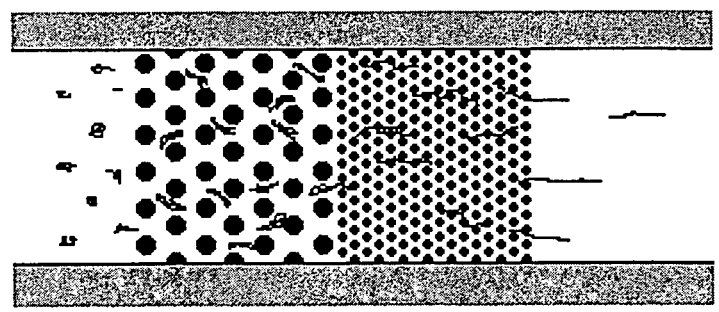

FIG. 14 shows how a polymer can stretch in an embodiment of the obstacle field regime with gradated sizing of obstacles.

Figure 15:
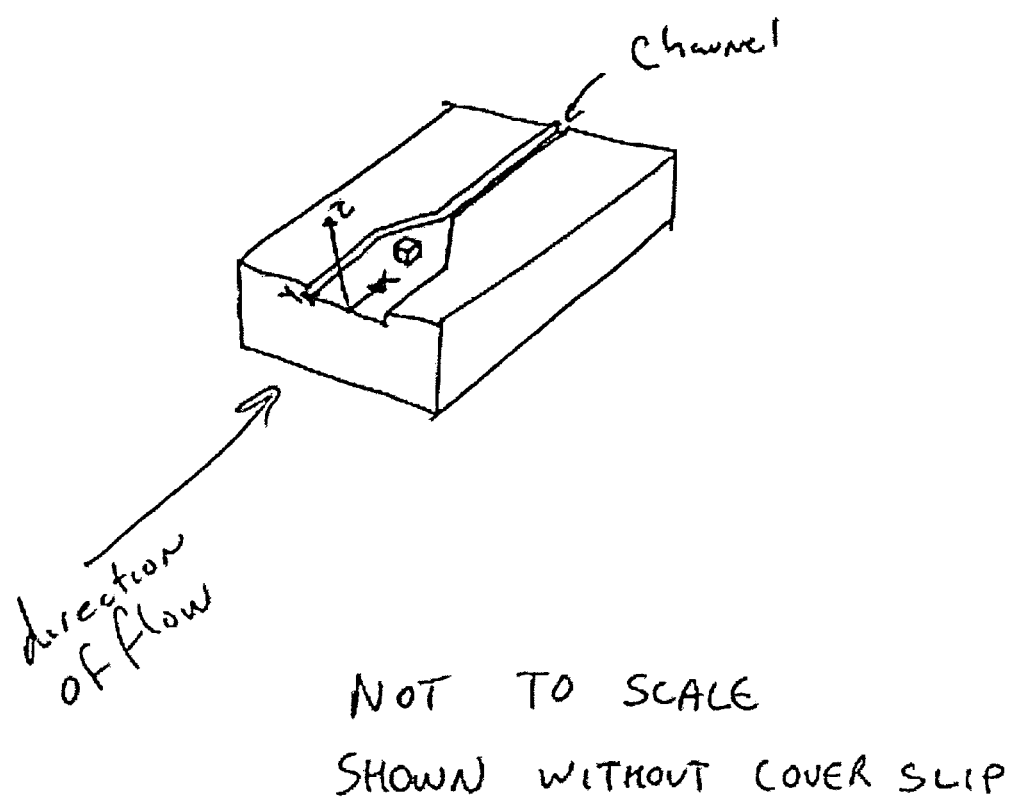

FIG. 15 shows the coordinate frame for an elongation structure.

Figure 16A:
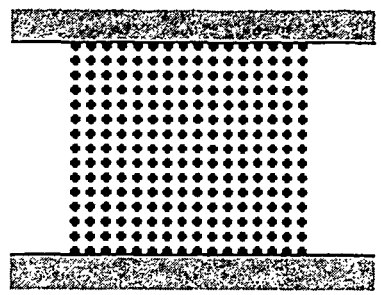

FIG. 16(a) shows an embodiment of the obstacle field regime with square-grid alignment of circular obstacles; (b) shows an embodiment of the obstacle field regime with an offset-grid alignment of circular obstacles.

Figure 17:
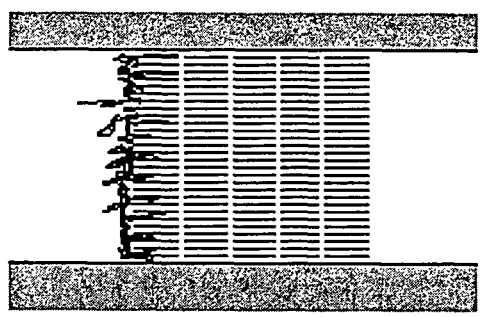

FIG. 17 shows an embodiment of the obstacle field regime with close spacing of rectangular obstacles of an exaggerated aspect ratio.

Figure 18:
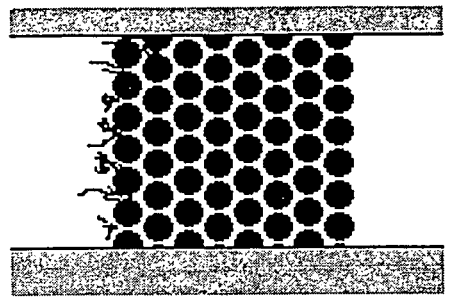

FIG. 18 shows an embodiment of the obstacle field regime with close spacing of circular obstacles.

Figure 19:
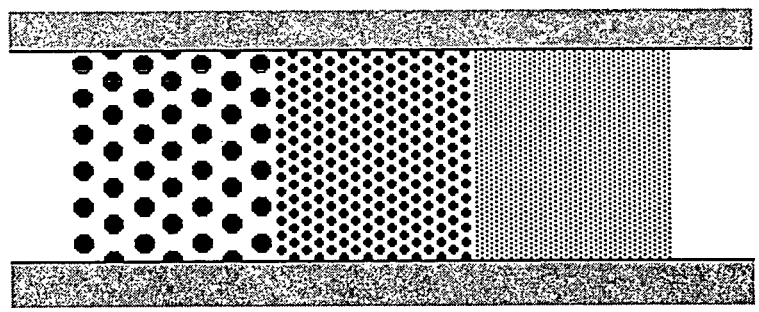

FIG. 19 shows an embodiment of the obstacle field regime with three gradated sizes of circular obstacles.

Figure 20:
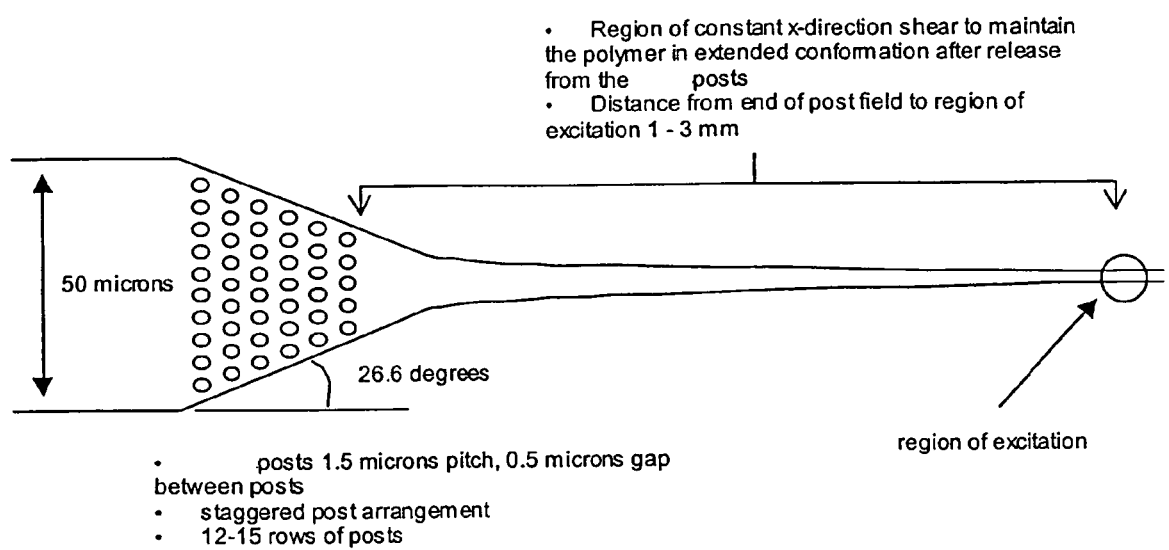

FIG. 20 shows a configuration for consistent unraveling, delivery, and stretching of DNA of varying sizes.

Figure 21:
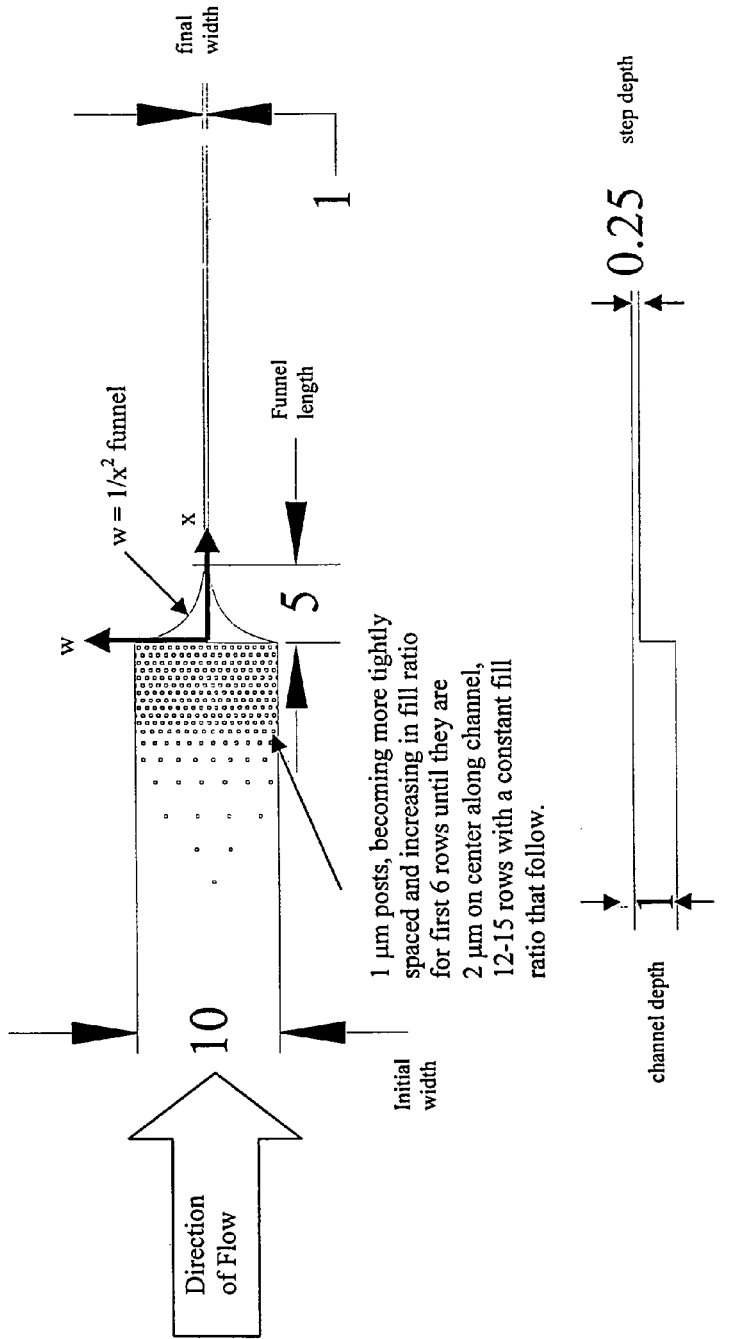

FIG. 21 shows a configuration of a preferred embodiment of a structure for stretching DNA that combines a post field, a funnel that tapers as $1/x^2$, wherein x is the distance along the length of the funnel, and a step that reduces the channel depth.

Figure 22:
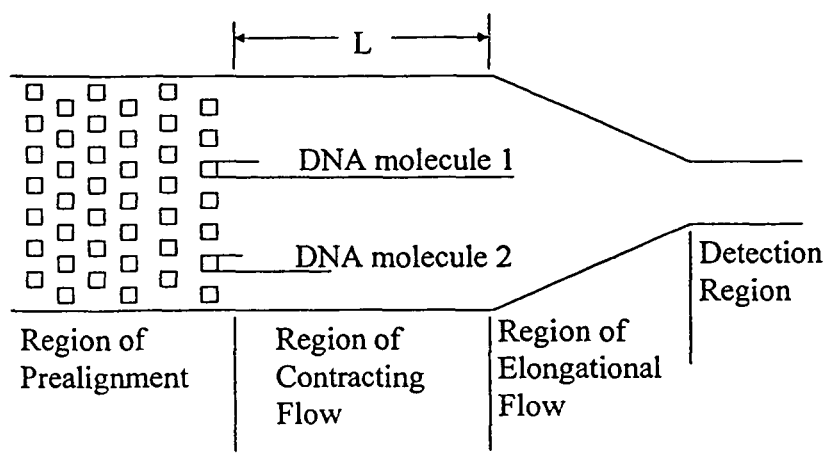

FIG. 22 shows a schematic of a molecular size sorting device, wherein signals of molecules of length L or greater can be easily distinguished from signals of molecules of length less than L.

Figure 23:
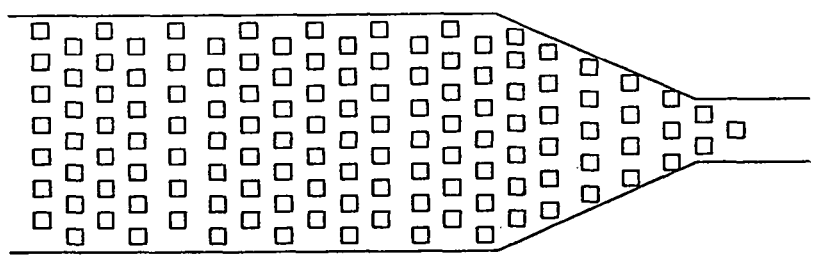

FIG. 23 shows a schematic of a device that stretches molecules of all lengths, such that signals from all of them are uniformly detected.

Figure 24:
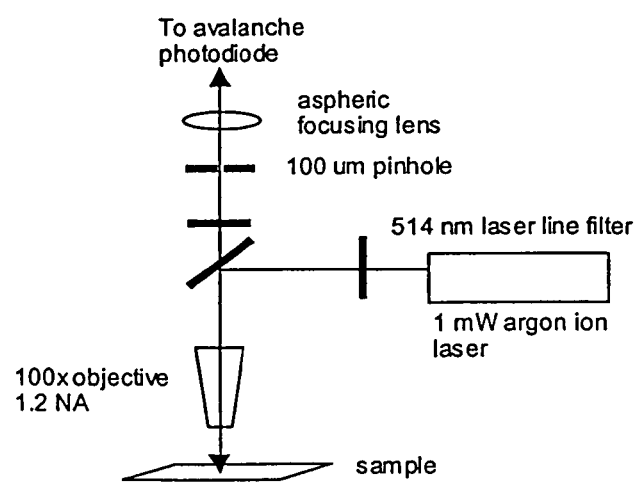

FIG. 24 shows a sensitive optical apparatus that utilizes confocal fluorescence illumination and detection.

Figure 25:
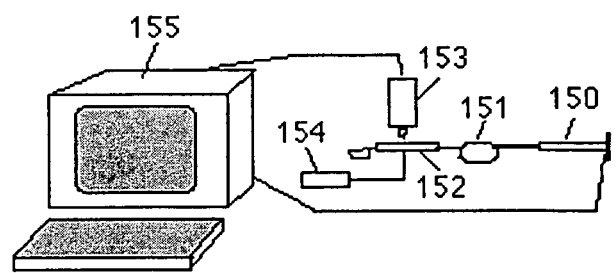

FIG. 25 demonstrates one embodiment of the overall polymer analysis system.

Figure 26:
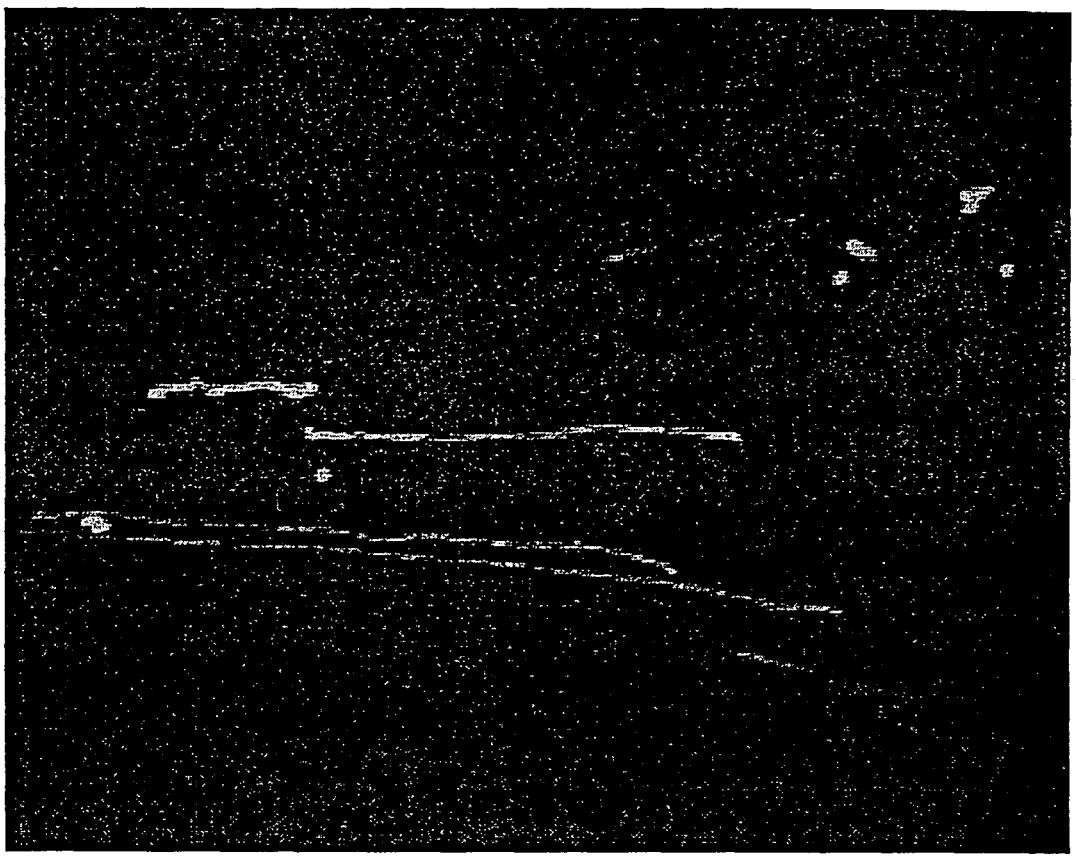
Figure 27A:
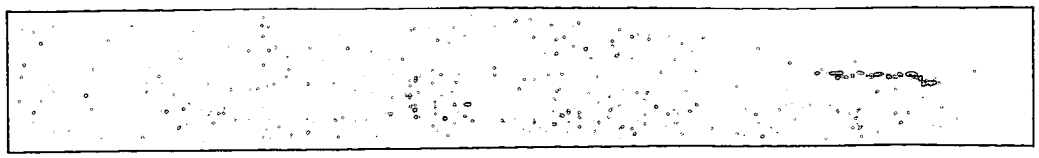
Figure 27B:
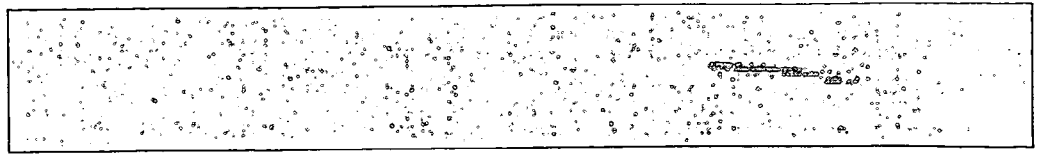
Figure 27C:
Figure 27D:
Figure 27E:
Figure 27F:
Figure 27G:
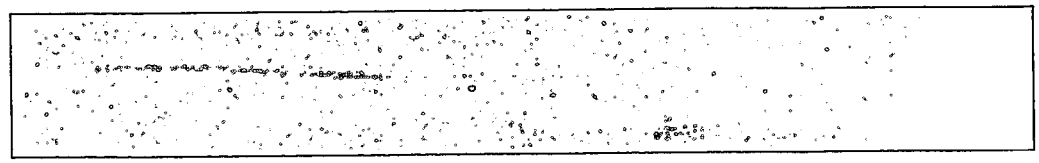

FIG. 26 shows DNA in various stretching states in the entrance to a constant-shear channel.

FIG. 27 (a-g) show a 50 kb DNA being stretched out in a tapered channel.

Figure 28:
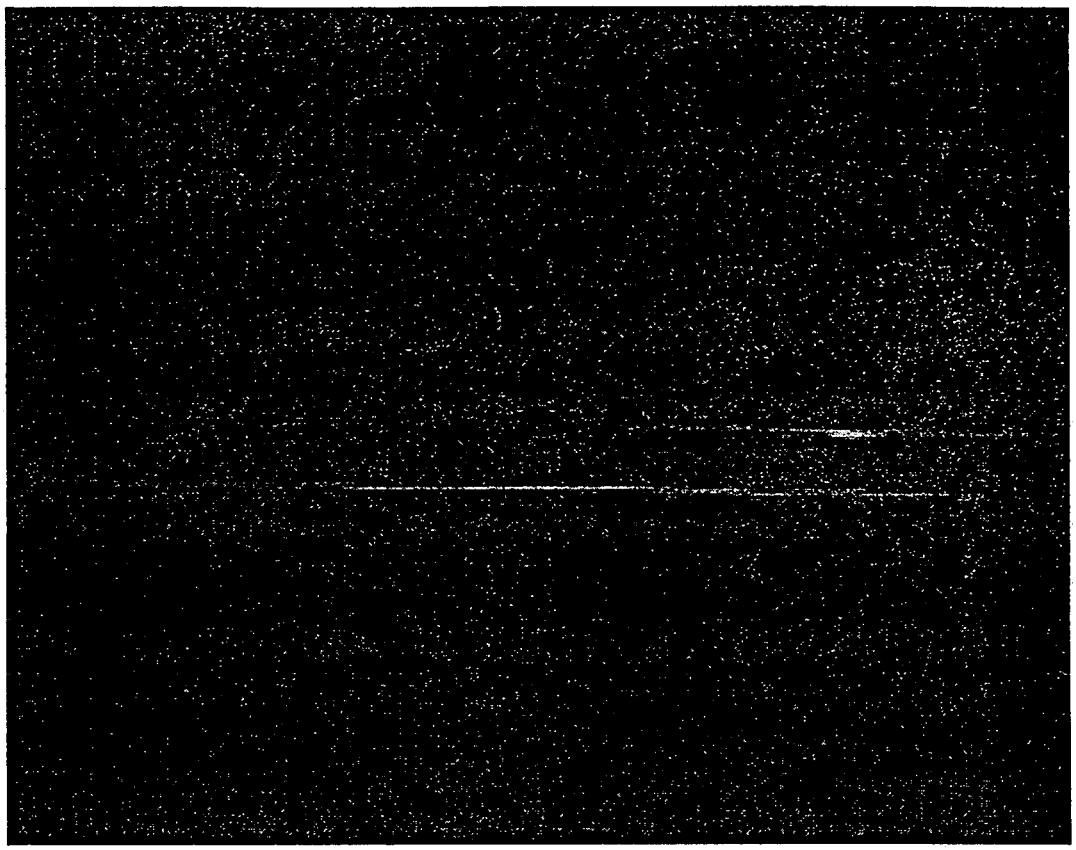

FIG. 28 shows a DNA measured at 537 kb stretched out in a channel.

Figure 29:
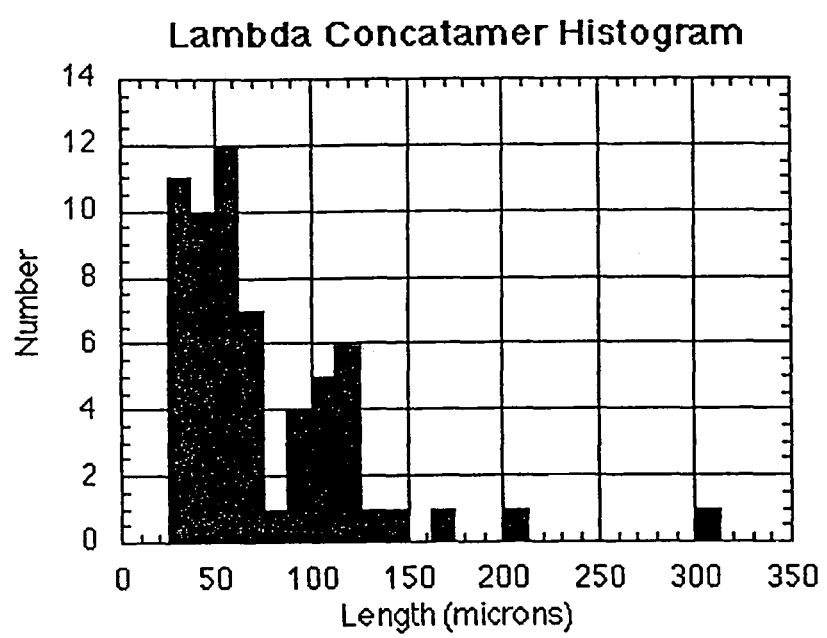

FIG. 29 shows a histogram displaying experimentally determined DNA lengths.

Figure 30:
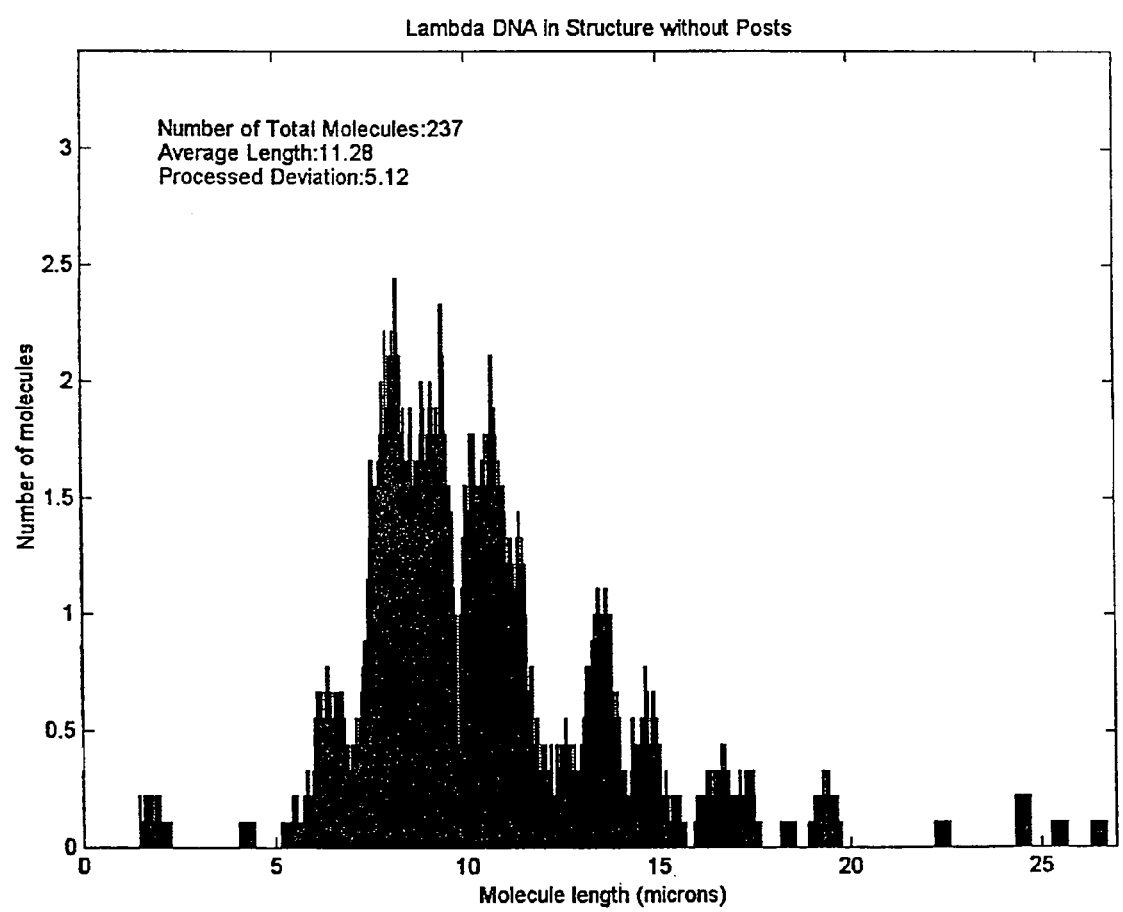
Figure 30:
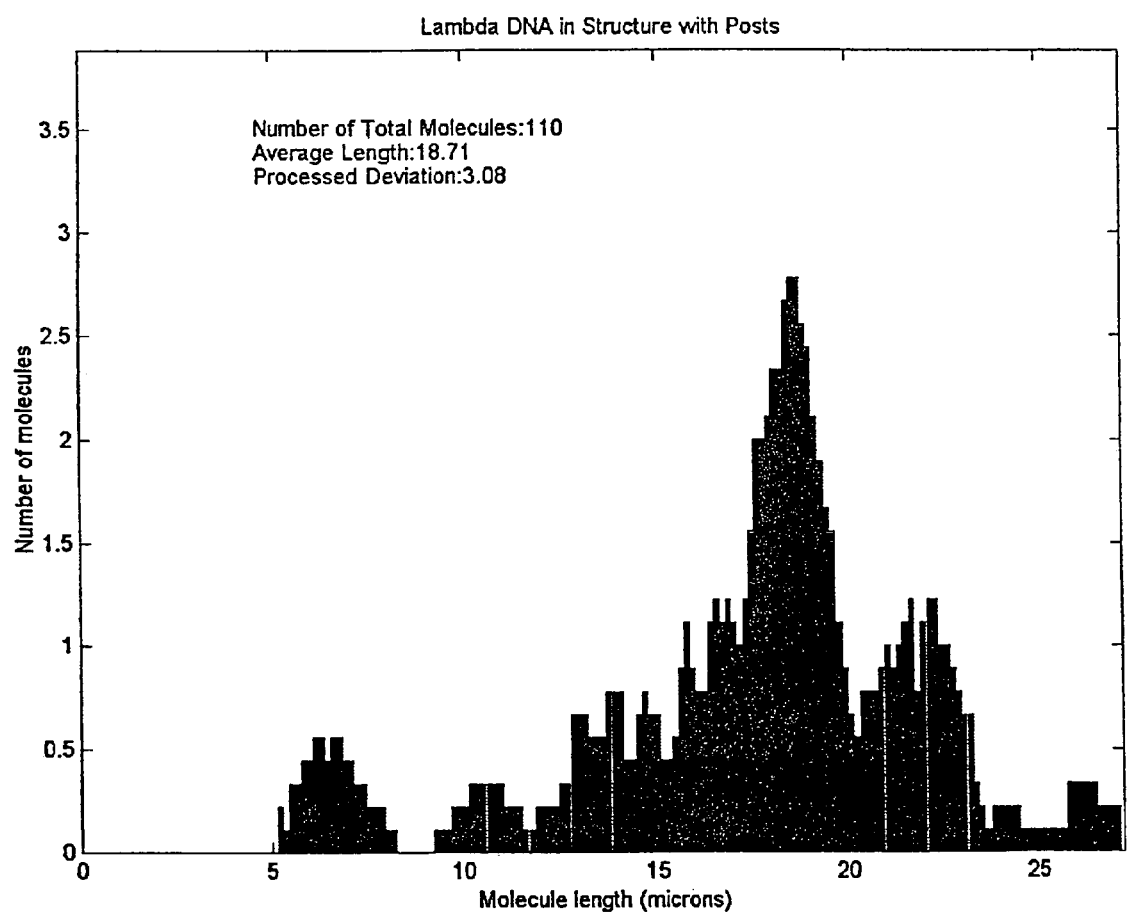

FIG. 30 shows histograms of experimentally determined lengths of phage lambda DNA from the structure of FIG. 20 (a) without posts, and (b) with posts.

5. DETAILED DESCRIPTION OF THE INVENTION

5.1 Introduction

The present invention provides structures that allow polymers of any length, including nucleic acids containing entire genomes, to be stretched into a long, linear conformation for further analysis. Polymers are loaded into a device and run through the structures, propelled by, inter alia, physical, electrical or chemical forces. Stretching is achieved by, e.g., applying shear forces as the polymer passes through the structures, placing obstacles in the path of the polymer, or a combination thereof. Because the forces are applied continuously, it is possible to stretch out polymers to a length that is equal to or greater than the active area of the apparatus, i.e., where information about the polymer is collected as the polymer is analyzed. For example, if a video camera or laser illuminated volume is focused on the region of the chip where spreading occurs, we can monitor unlimited lengths of DNA molecules, i.e., much larger than the video image or the laser illumination volume. Since multiple molecules may be stretched in succession, extremely high throughput screening, e.g., screening of more than one molecule per second, is achieved.

Extended polymers or ensembles of polymers are characterized. Extended, labeled polymers are moved past at least one station, at which labeled units of the polymers interact with the station to produce an object-dependent impulse. As used in this application, "moves past" refers to embodiments in which the station is stationary and the extended polymer is in motion, the station is in motion and the extended polymer is stationary, and the station and extended polymer are both in motion.

Although the invention may be used for characterizing any polymer, it is preferable that the polymers have a predominantly, though not necessarily exclusively, linear or single-chain arrangement. Examples of such polymers include biological polymers such as deoxyribonucleic acids, ribonucleic acids, polypeptides, and oligosaccharides. The polymers may be heterogeneous in backbone composition, thereby containing any possible combination of individual monomer units linked together, e.g., peptide-nucleic acids (PNA), which have amino acids linked to nucleic acids. In a preferred embodiment, the polymers are homogeneous in backbone composition and are, e.g., nucleic acids, polypeptides or oligosaccharides. The term "backbone" is given its usual meaning in the field of polymer chemistry. A nucleic acid as used herein is a biopolymer comprised of nucleotides, such as deoxyribose nucleic acid (DNA) or ribose nucleic acid (RNA). A protein or polypeptide as used herein is a biopolymer comprised of amino acids. In the most preferred embodiment, the extended object is a double-stranded DNA molecule.

As used herein with respect to individual units of a polymer, "linked" or "linkage" means two units are joined to each other by any physicochemical means. Any linkage known to those of ordinary skill in the art, covalent or non-covalent, is embraced. Natural linkages, e.g., amide, ester, and thioester linkages, which are those ordinarily found in nature to connect the individual units of a particular polymer, are most common. However, the individual units of a polymer stretched by the structures of the invention may be joined by synthetic or modified linkages.

A polymer is made up of a plurality of individual units, which are building blocks or monomers that are linked either directly or indirectly to other building blocks or monomers to form the polymer. The polymer preferably comprises at least two chemically distinct linked monomers. The at least two chemically distinct linked monomers may produce or be labeled to produce different signals. Different types of polymers are composed of different monomers. For example, DNA is a biopolymer comprising a deoxyribose phosphate backbone to which are attached purines and pyrimidines such as adenine, cytosine, guanine, thymine, 5-methylcytosine, 2-aminopurine, hypoxanthine, and other naturally and non-naturally occurring nucleobases, substituted and unsubstituted aromatic moieties. RNA is a biopolymer comprising a ribose phosphate backbone to which are attached purines and pyrimidines such as those described for DNA but wherein uracil is substituted for thymidine. Deoxyribonucleotides may be joined to one another via an ester linkage through the 5' or 3' hydroxyl groups to form the DNA polymer. Ribonucleotides may be joined to one another via an ester linkage through the 5', 3' or 2' hydroxyl groups. Alternatively, DNA or RNA units having a 5', 3' or 2' amino group may be joined via an amide linkage to other units of the polymer.

The polymers may be naturally-occurring or non-naturally occurring polymers. Polymers can be isolated, e.g., from natural sources using biochemical purification techniques. Alternatively, polymers may be synthesized, e.g., enzymatically by in vitro amplification using the polymerase chain reaction (PCR), by chemical synthesis, or by recombinant techniques.

The structures of the invention are used in conjunction with methods for analyzing the extended polymers by detecting signals referred to as object-dependent impulses. An "object-dependent impulse," as used herein, is a detectable physical quantity which transmits or conveys information about the structural characteristics of at least one unit-specific marker of an extended polymer. A unit-specific marker, as used herein, can either be a measurable intrinsic property of a particular type of individual unit of the extended polymer, e.g., the distinct absorption maxima of the naturally occurring nucleobases of DNA (the polymer is intrinsically labeled), or a compound having a measurable property that is specifically associated with one or more individual units of a polymer (the polymer is extrinsically labeled). A unit-specific marker of an extrinsically labeled polymer may be a particular fluorescent dye with which all nucleobases of a particular type, e.g., all thymine nucleobases, in a DNA strand are labeled. Alternatively, a unit-specific marker of an extrinsically labeled polymer may be a fluorescently labeled oligonucleotide of defined length and sequence that hybridizes to and therefore "marks" the complementary sequence present in a target DNA. Unit-specific markers may further include, but are not limited to, sequence specific major or minor groove binders and intercalators, sequence-specific DNA or peptide binding proteins, sequence specific PNAs, etc. The detectable physical quantity may be in any form that is capable of being measured. For instance, the detectable physical quantity may be electromagnetic radiation, chemical conductance, radioactivity, etc. The object-dependent impulse may arise from energy transfer, directed excitation, quenching, changes in conductance (resistance), or any other physical changes. In one embodiment, the object-dependent impulse arises from fluorescence resonance energy transfer ("FRET") between the unit-specific marker and the station, or the environment surrounding the station. In preferred embodiments, the object-dependent impulse results from direct excitation in a confined or localized region, or epiillumination of a confocal volume or slit-based excitation is used. Possible analyses of polymers include, but are not limited to: determination of polymer length, determination of polymer sequence, determination of polymer velocity, determination of the degree of identity of two polymers, determination of characteristic patterns of unit-specific markers of a polymer to produce a "fingerprint", and characterization of a heterogeneous population of polymers using a statistical distribution of unit-specific markers within a sample population.

There are numerous methods and products available for analyzing polymers as described in PCT Publication No. WO 98/35012, which is incorporated herein by reference in its entirety.

Various methods for analyzing polymers differ in their potential sensitivity and resolution, i.e., the minimum distance between two unit-specific markers wherein the unit-specific markers are distinguishable. A low resolution technique is capable of distinguishing unit-specific markers having a larger distance between them; a high resolution technique is capable of distinguishing unit-specific markers having a smaller distance between them. The resolution of a particular technique is determined by the characteristic distance through which the station may sense the particular unit-specific marker of the extended polymer. A shorter characteristic distance makes for better resolution. The lowest resolution techniques include monitoring of light transmission and directed excitation, which have a resolution of 50-100 nm or more (Tan & Kopelman (1996) Chem. Anal. Ser. 137: 407-475.). In contrast, the resolution of FRET is on the order of the Förster radius, the distance between donors and acceptors at which the most efficient energy transfer occurs, which is typically on the order of 2-7 nm. The distance between adjacent base pairs in a fully-extended DNA molecule having the B-conformation is 3.4 Å, or 0.34 nm. In its natural state in solution, DNA does not exist in its fully-extended B-conformation, but as a coil with a diameter on the order of 10 µm. Therefore, it is much more difficult to resolve a plurality of unit-specific markers on a coiled DNA molecule and the molecule should be extended before analysis.

5.2 Shear Force as a Means of Stretching Polymers

When a polymer molecule reaches a physical obstruction, it will either pass by without interaction or "hook" around the obstruction such that portions of the chain remain on each side of the obstacle. This does not mean the polymer is bonded to the obstruction or otherwise physically attached. The lopsidedness of the draping around the obstacle determines the rapidity with which the molecule proceeds down the favored side. (See Austin & Volkmuth, Analysis 1993 (21) 235-238.) In addition, localized velocity gradients are created at the obstacles, since the cross-sectional area available for fluid flow is reduced. As a result, the fluid flowing in between the obstacles moves faster than the fluid before and after. This creates a shear force acting on approaching molecules that serves as a stretching force on the polymer. When this effect is multiplied by having an entire field of properly-sized obstacles, the polymer stretches out to make it past all the obstacles in the field. In a preferred embodiment, the polymer is stretched out in a linear fashion.

Once the polymer has passed the array of obstacles and enters a channel in its fully extended form, where in a preferred embodiment it is analyzed, it will naturally tend to return to a lower-energy, more coiled conformation. To prevent this from happening, channels are designed to provide a constant shear force on the polymer in a narrowing channel, causing it to remain in a stretched conformation.

A constant shear rate, or change in average velocity with distance in the channel, is defined as S:

$$\partial u/\partial x = S \qquad (5)$$

where x is the distance down a substantially rectangular channel, and u is the average fluid velocity in the x direction, which is computed from the overall fluid flow (Q) and the cross-sectional area, A, of the channel as follows:

$$u = Q/A \qquad (6).$$

In one embodiment where the channel cross-section is rectangular, the channel may be defined by a constant height, H and width, W such that the cross-sectional area A=HW, and the average fluid velocity is given by:

$$u = Q/HW \qquad (7)$$

Applying the boundary condition that the fluid flow must be continuous (i.e., incompressible), Q is constant. Hence, u is inversely proportional to W. This relationship can be substituted into the original expression for S to determine a relationship between the shear rate and the width:

$$S = \partial u/\partial x = Q/H \partial/\partial x(1/W) = (-Q/HW^2)(dW/dx) \qquad (8)$$

$$dW/dx = (-SH/Q)(W^2) \qquad (9)$$

Integrating this expression, it is found that:

$$W = (SHx/Q + C)^{-1} \qquad (10)$$

where C is a constant of integration determined by the original width of the channel (boundary condition). This equation for the width of the channel is used to define a channel beyond a post structure. Similar calculations may readily be completed by those of skill in the art for non-rectangular channel shapes. When no net momentum transfer occurs in the height axis, i.e., when the velocity profile in the z-axis has been established, the shear rate from the width profile results in a stretching force. Illustrating in the case of a Newtonian fluid, the stress tensor, $\tau_{yz}$ required to compute the force is easily expressed in terms of the shear rate:

$$F = \int\int \tau_{yz} dz dx = \int\int -\mu(du/dx) dz dx = \int\int \mu S dz dx \qquad (11)$$

where µ is the solution viscosity. In these equations, x is the direction of motion, y is the width, and z is the height. The surface over which the shear rate needs to be integrated is that of the channel wall, which results in:

$$F = \mu HLS \qquad (12)$$

where L is the length of the channel wall, approximately the length of the channel in which the constant shear is maintained.

Therefore, an aqueous channel with 1 µm depth, 1 mm length, and shear rate of 0.25/s gives a force of approximately 0.25 pN, adequate to stretch DNA, which the inventors have verified experimentally. Notably, this result confirms that the constant-shear channel not only maintains the extension of previously-stretched DNA, but also contributes to further stretching of DNA, or stretches DNA on its own.

In a preferred embodiment, the two general methods for achieving stretching have been combined. Gradated arrays of obstacles that are posts have been placed in structures which also impart shear forces on passing molecules, ensuring not only the initial stretching of the polymer by the obstacles, but also the maintenance of stretching after the polymer has traversed the obstacles.

5.3 Structures for Stretching Polymers

The structures for stretching DNA of the present invention ("elongation structures") comprise two components: a delivery region and a region of polymer elongation. The delivery region is a wider channel that leads into and out of the region of polymer elongation. The region of elongation comprises at least one of four main components: (1) funnels; (2) structures having branched channels; (3) channels with bends or curves; and (4) obstacles defining small gaps, wherein the obstacles can be, inter alia, posts or steps. The invention encompasses combinations of the four main components and variations of the main components themselves. A combination of two or more of the main component features can give rise to additional designs that work well to extend and stretch polymers, particularly DNA, in a controllable fashion. In addition, several of the same design may be repeated in parallel or in series.

Figure 1:
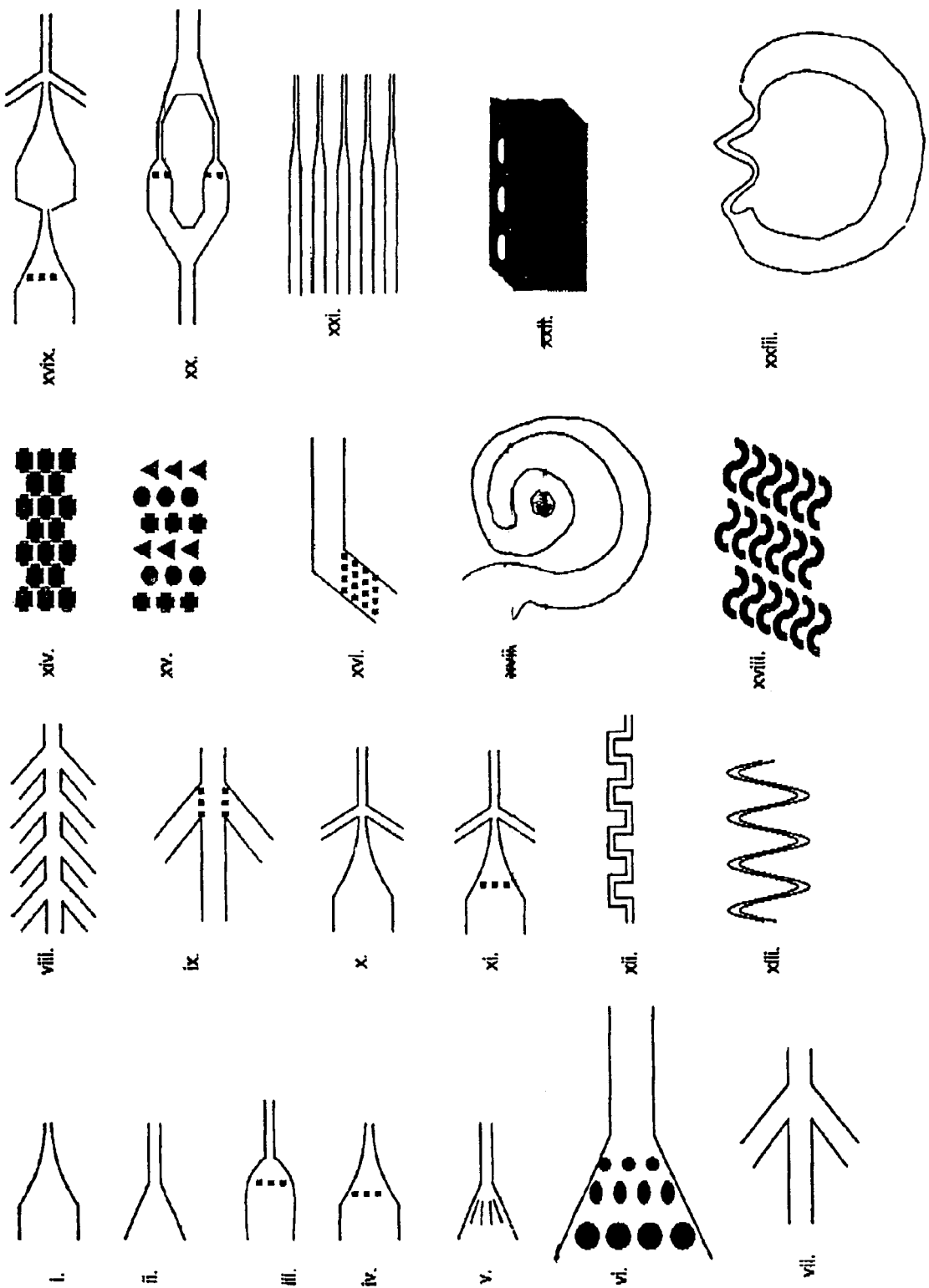

Examples of structures (FIG. 1) that fall within the scope of the invention include, but are not limited to:
i) funnels with a non-linear increase in fluid velocity;
ii) funnels with a linear increase in fluid velocity;
iii) funnels with obstacles defining small gaps as the region of DNA elongation;
iv) funnels with a non-linear increase in fluid velocity and obstacles defining small gaps;
v) funnels with a linear increase in fluid velocity and obstacles defining small gaps;
vi) funnels with mixed obstacle sizes and gaps, including a gradient of obstacles sizes and gaps;
vii) branched structures having regions of increased fluid velocity from converging channels;
viii) branched structures having multiple regions of increased fluid velocity from multiple converging channels;
ix) branched structures having obstacles defining small gaps;
x) branched structures which have at least one funnel as one of the branches;
xi) branched structures with mixed obstacle sizes and gaps, including a gradient of obstacle sizes and gaps;
xii) structures which have obstacles which define small gaps and also bends or curves;
xiii) structures which have obstacles defining small gaps which have a periodicity (sine patterns, boxcar repeats, zig-zags);
xiv) structures which have obstacles defining small gaps which are non-quadrilateral polygons;
xv) structures having a mixture of obstacles which define small gaps, e.g., a set of bars defining small gaps juxtaposed to a field of sine patterns, or a field of triangles, circles, or stars;
xvi) structures having obstacles defining small gaps integrated with funnels, branched structures, or bends or curves;
xvii) structures having bends or curves in a funnel shape;
xviii) structures having bends or curves with obstacles defining small gaps;
xix) structures having regions of DNA elongation in series;
xx) structures having regions of DNA elongation in parallel;
xxi) structures having multiple delivery channels with respective regions of elongation;
xxii) structures having three-dimensional geometries involving embodiments of the other categories; and
xxiii) structures which are closed loops containing regions of DNA stretching.

Figure 2:
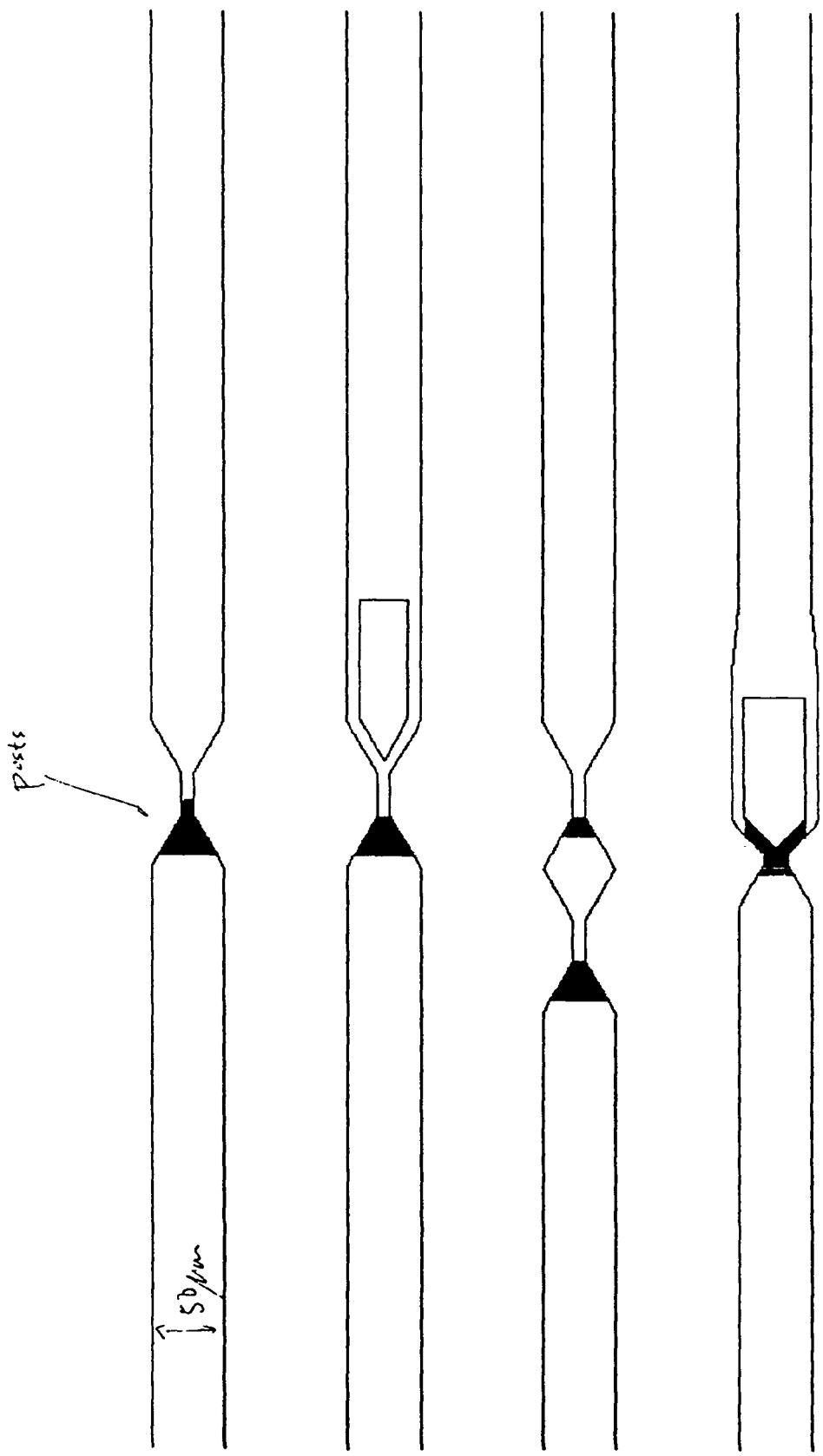
Figure 2:
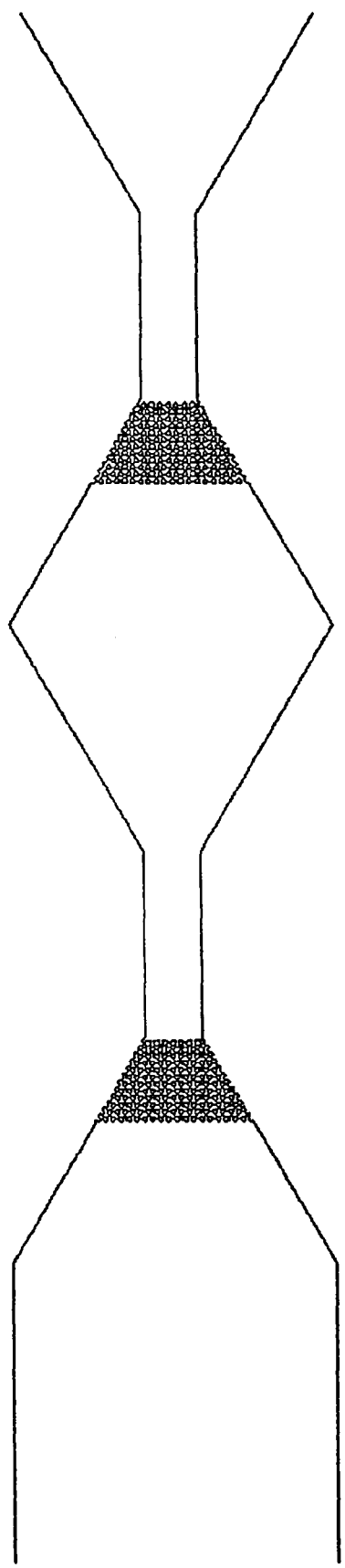
Figure 2:
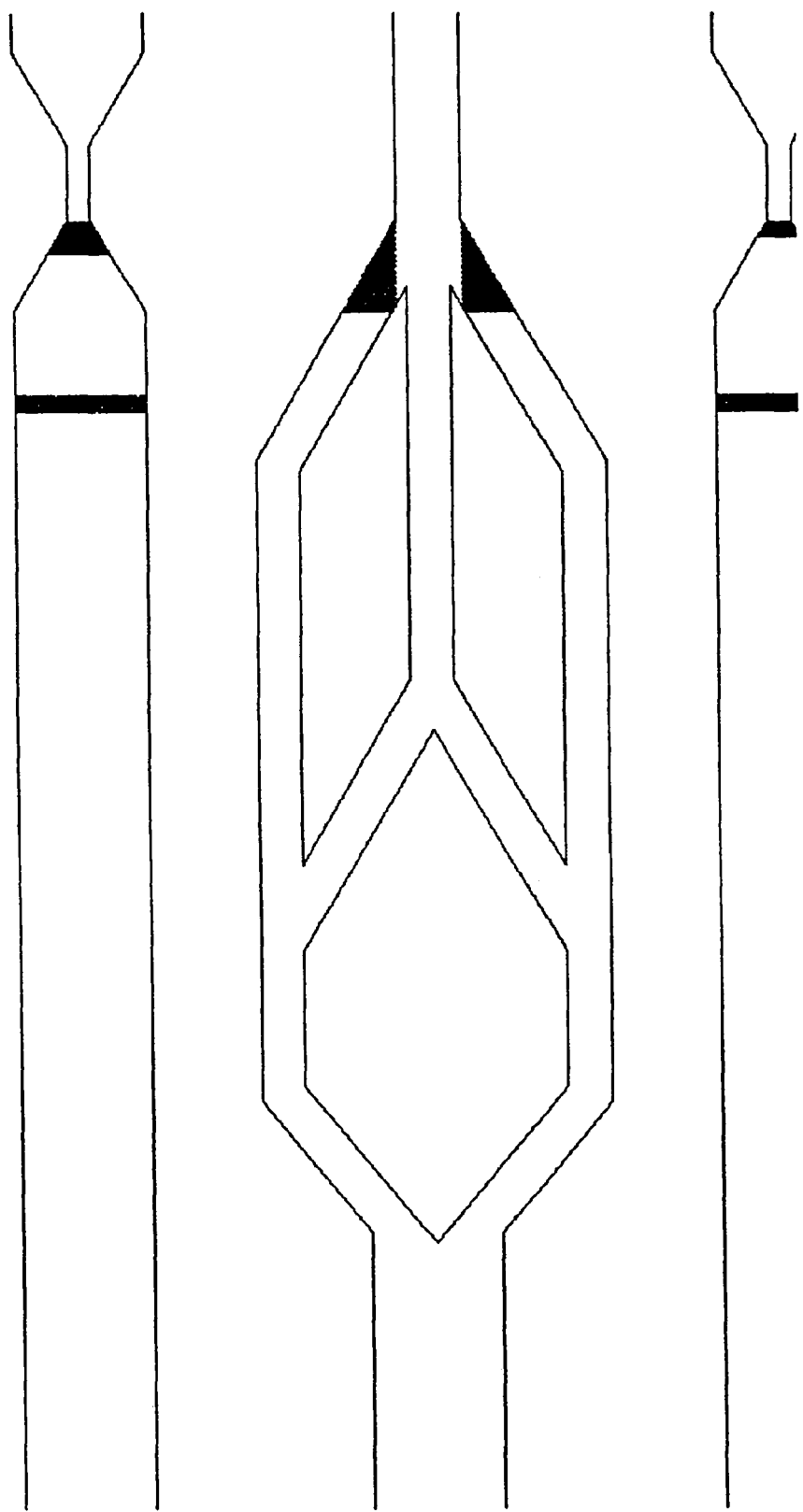
Figure 2:
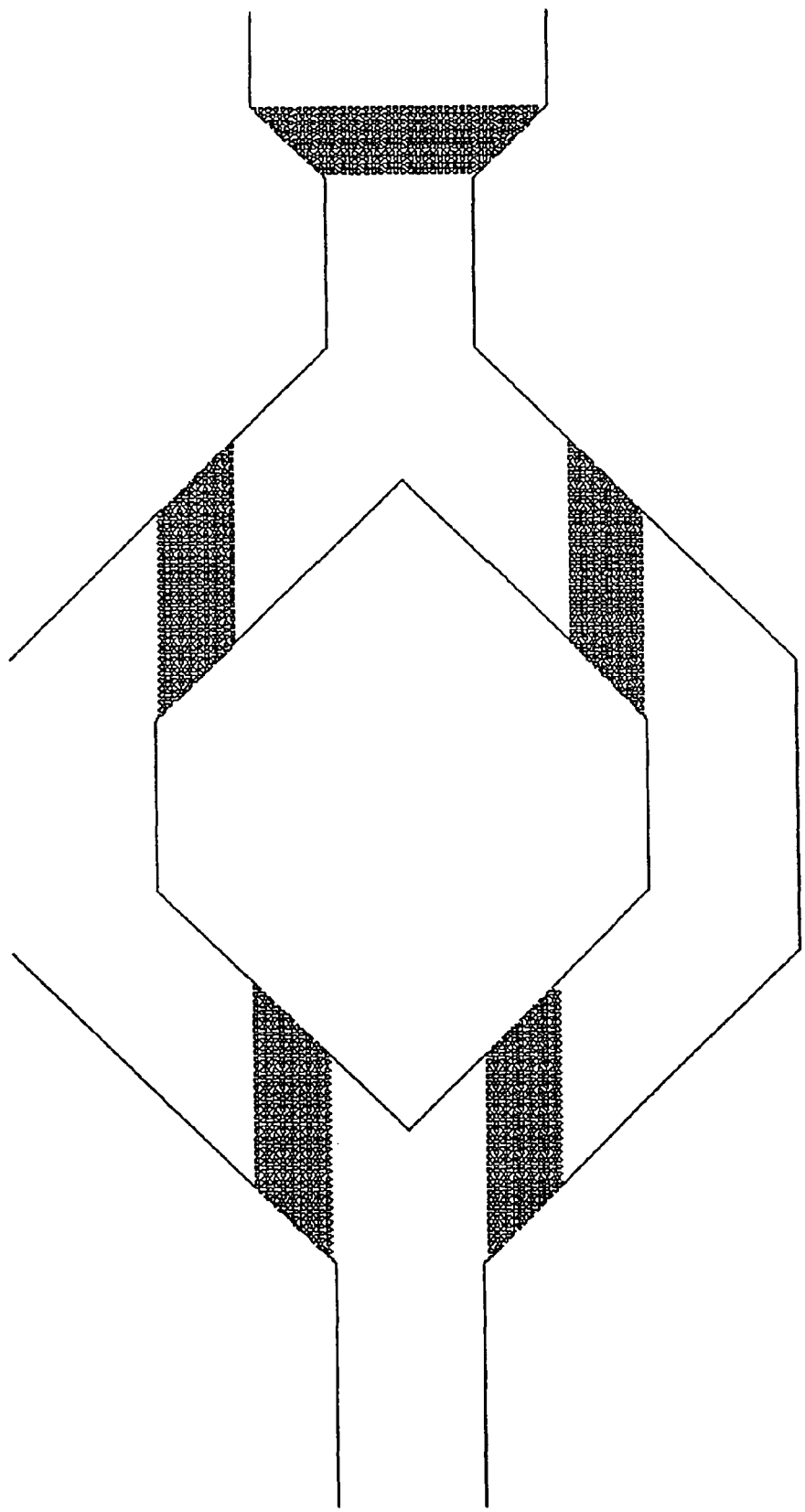
Figure 2:
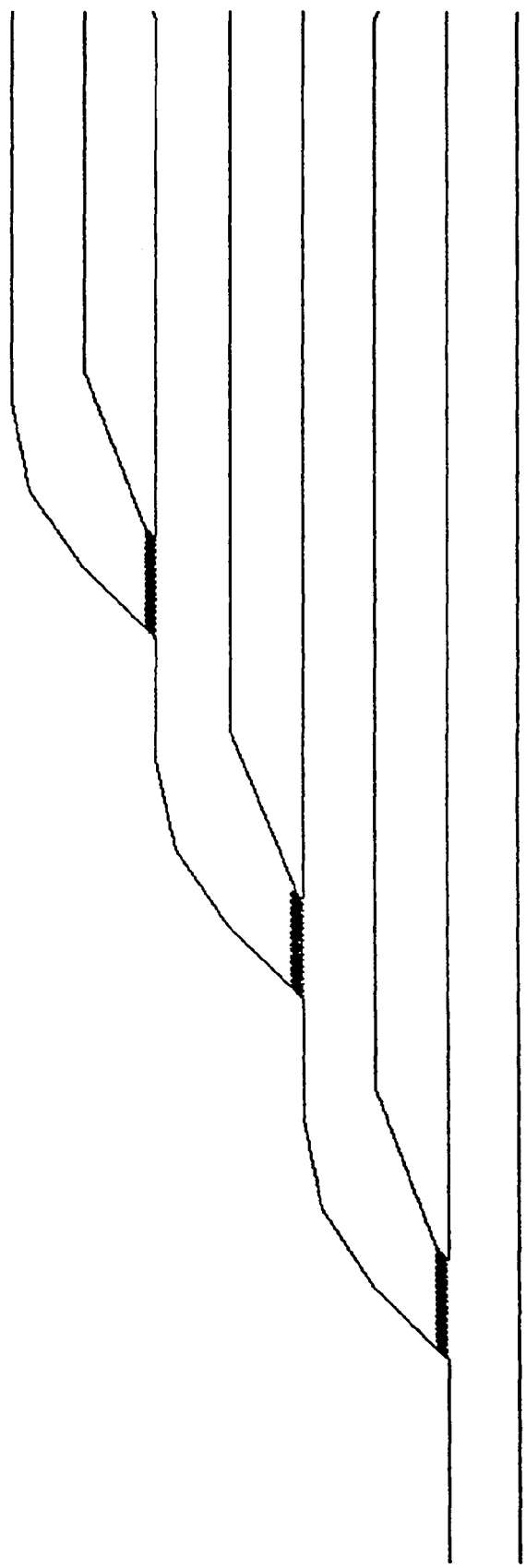
Figure 2:
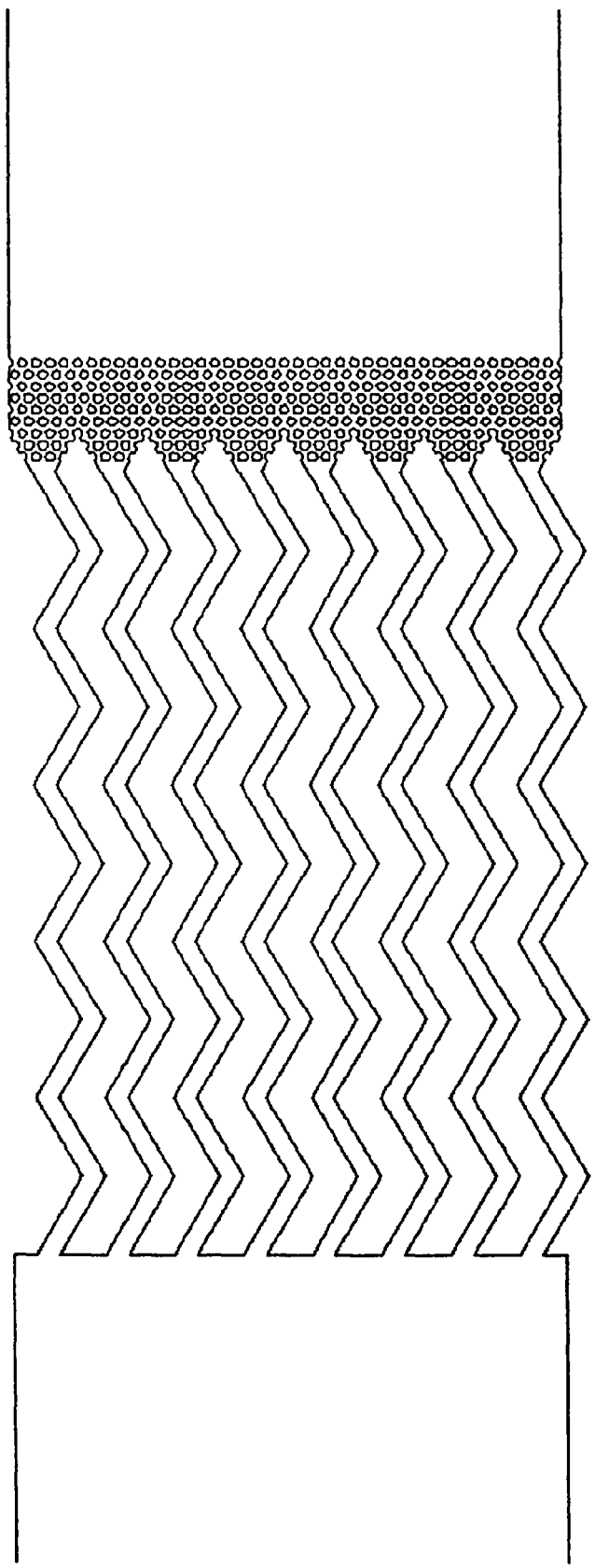
Figure 2:
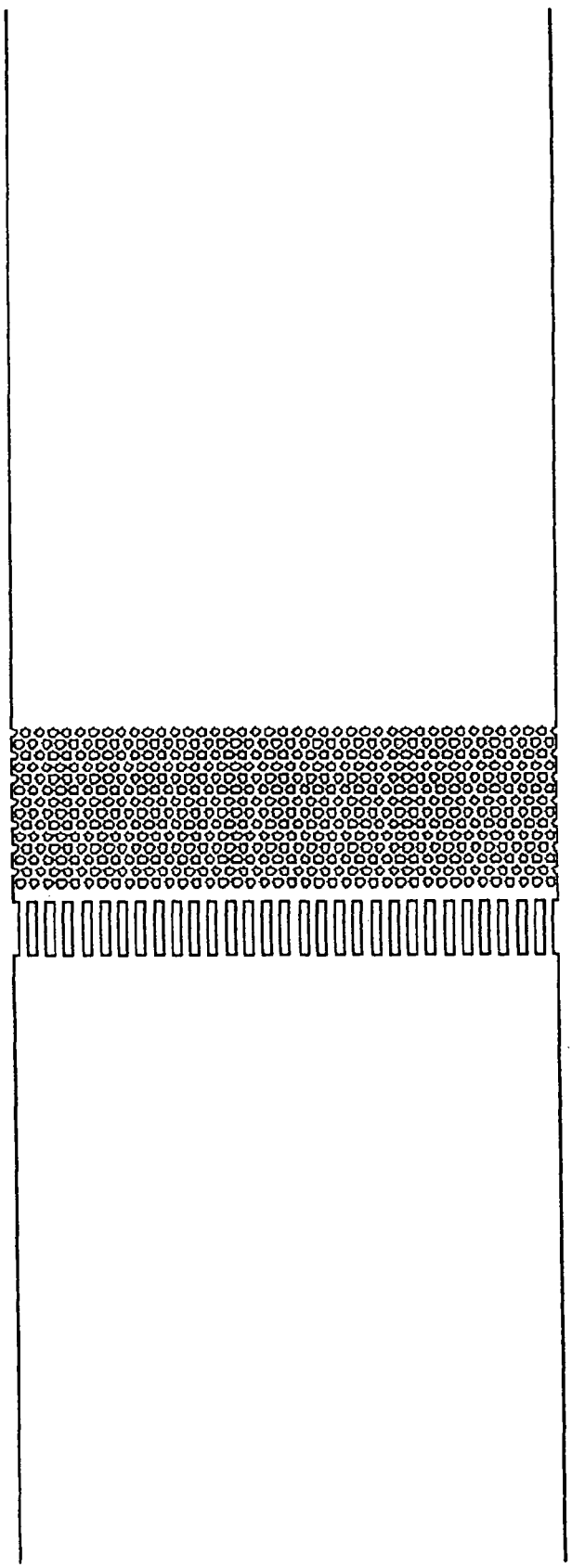
Figure 2:
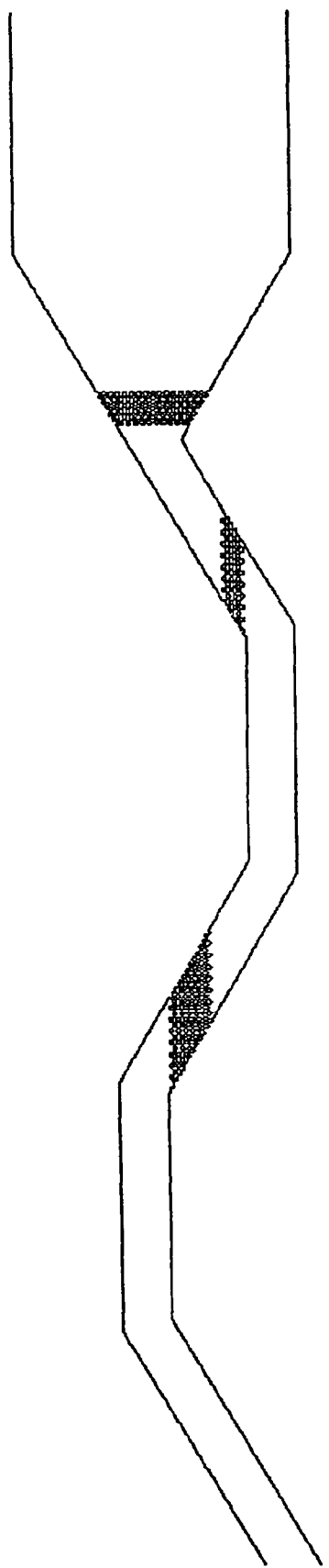
Figure 2:
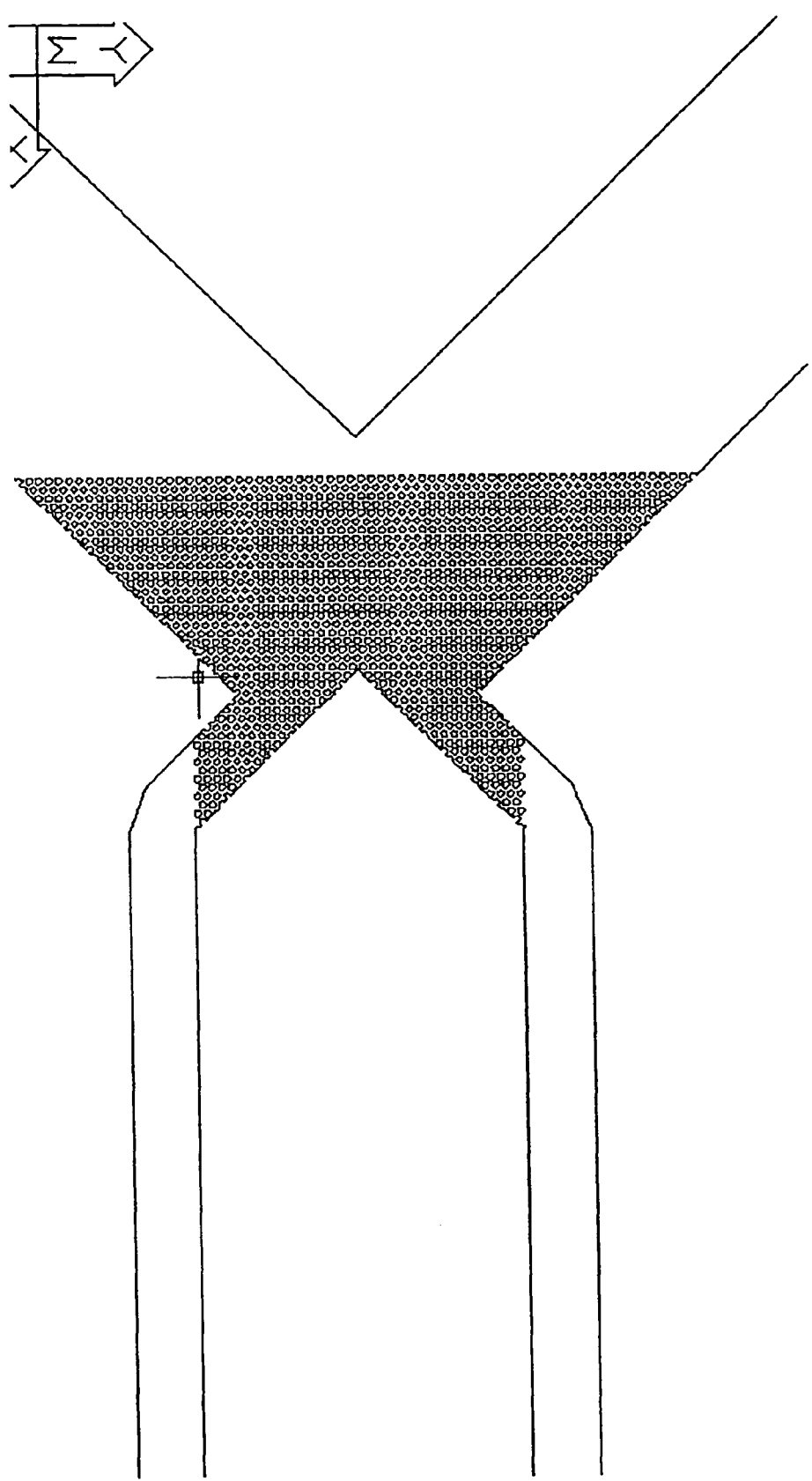
Figure 2:
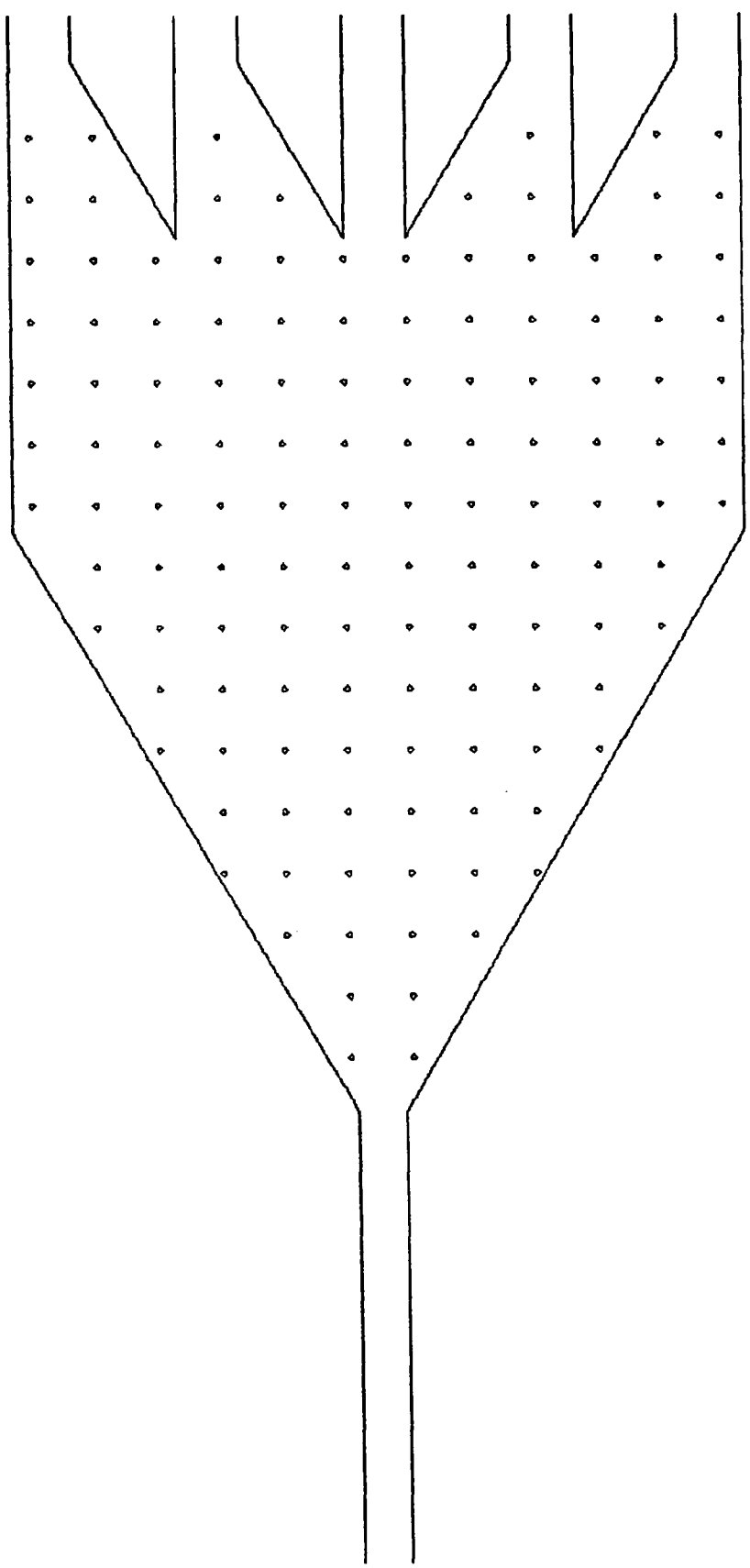
Figure 2:
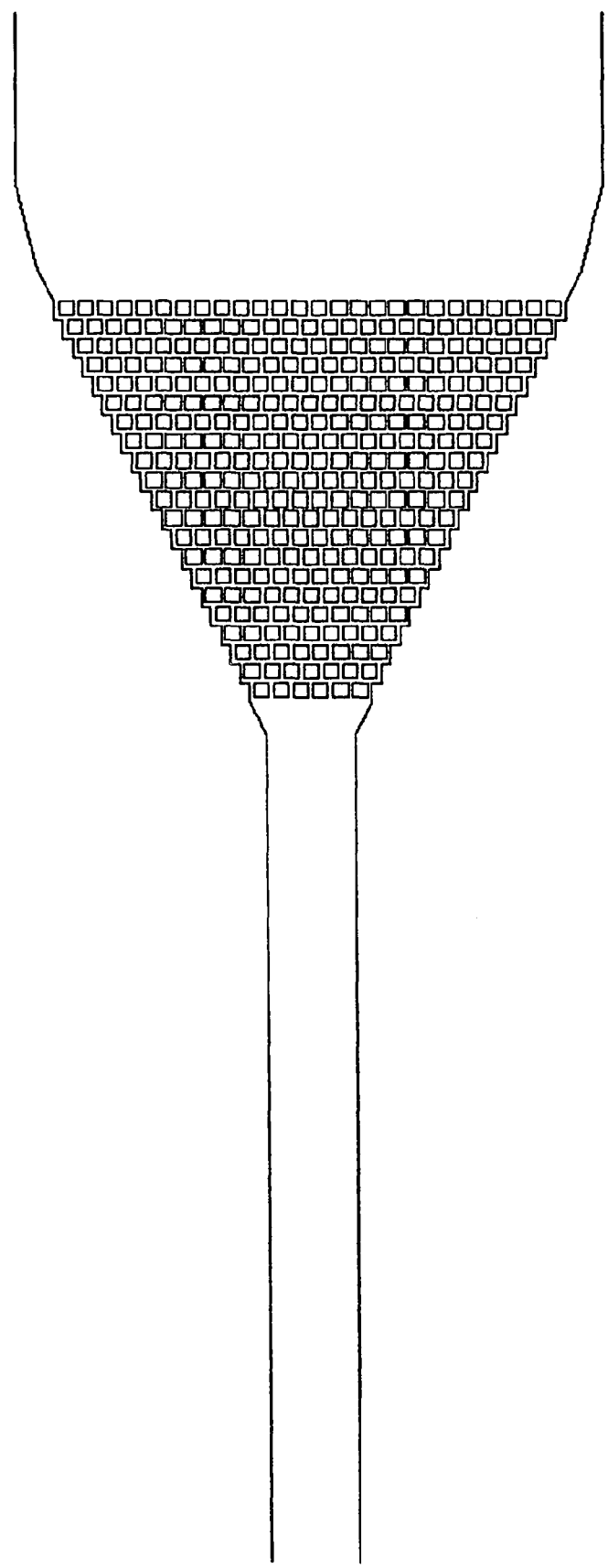
Figure 2:
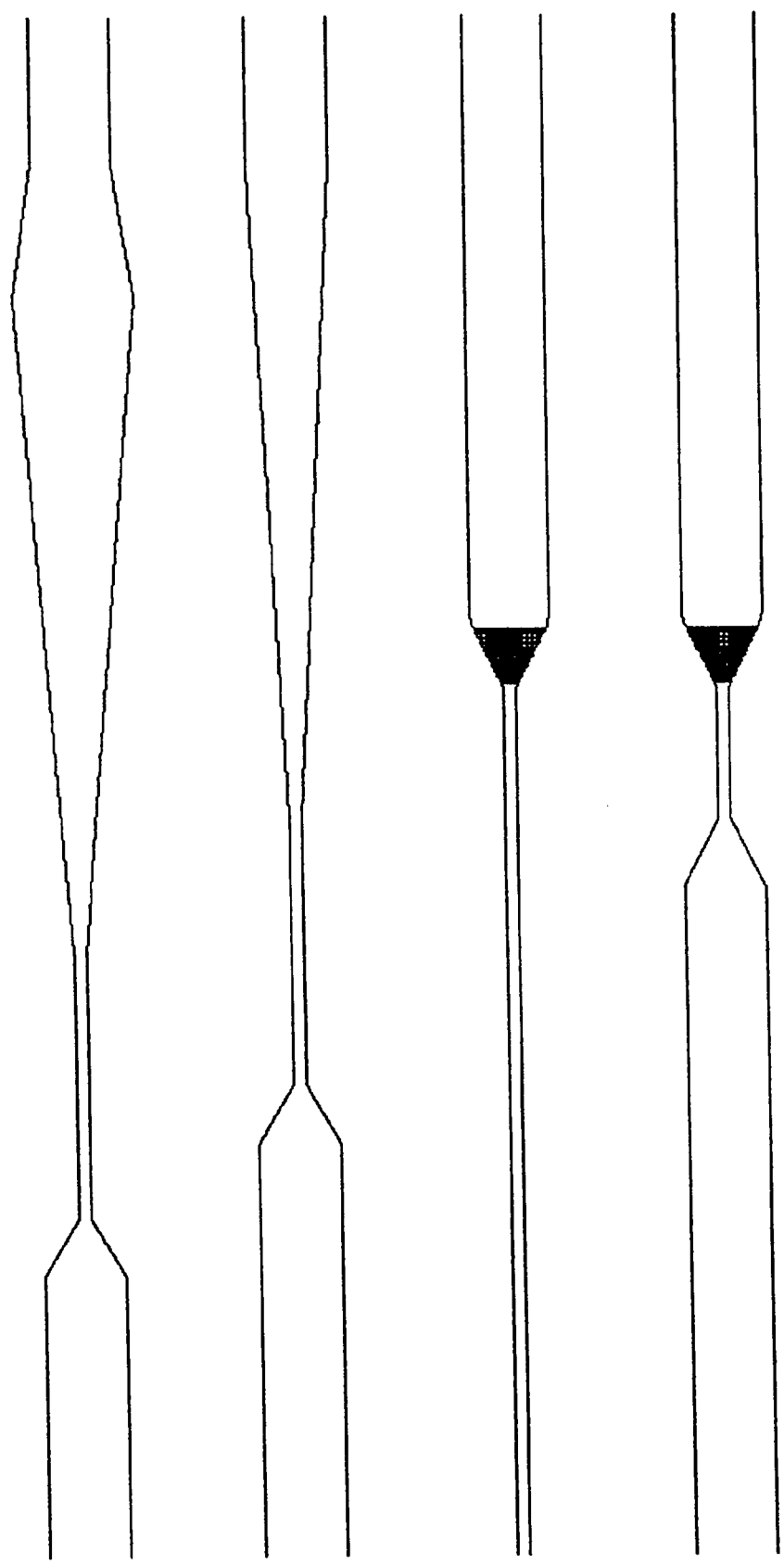
Figure 2:
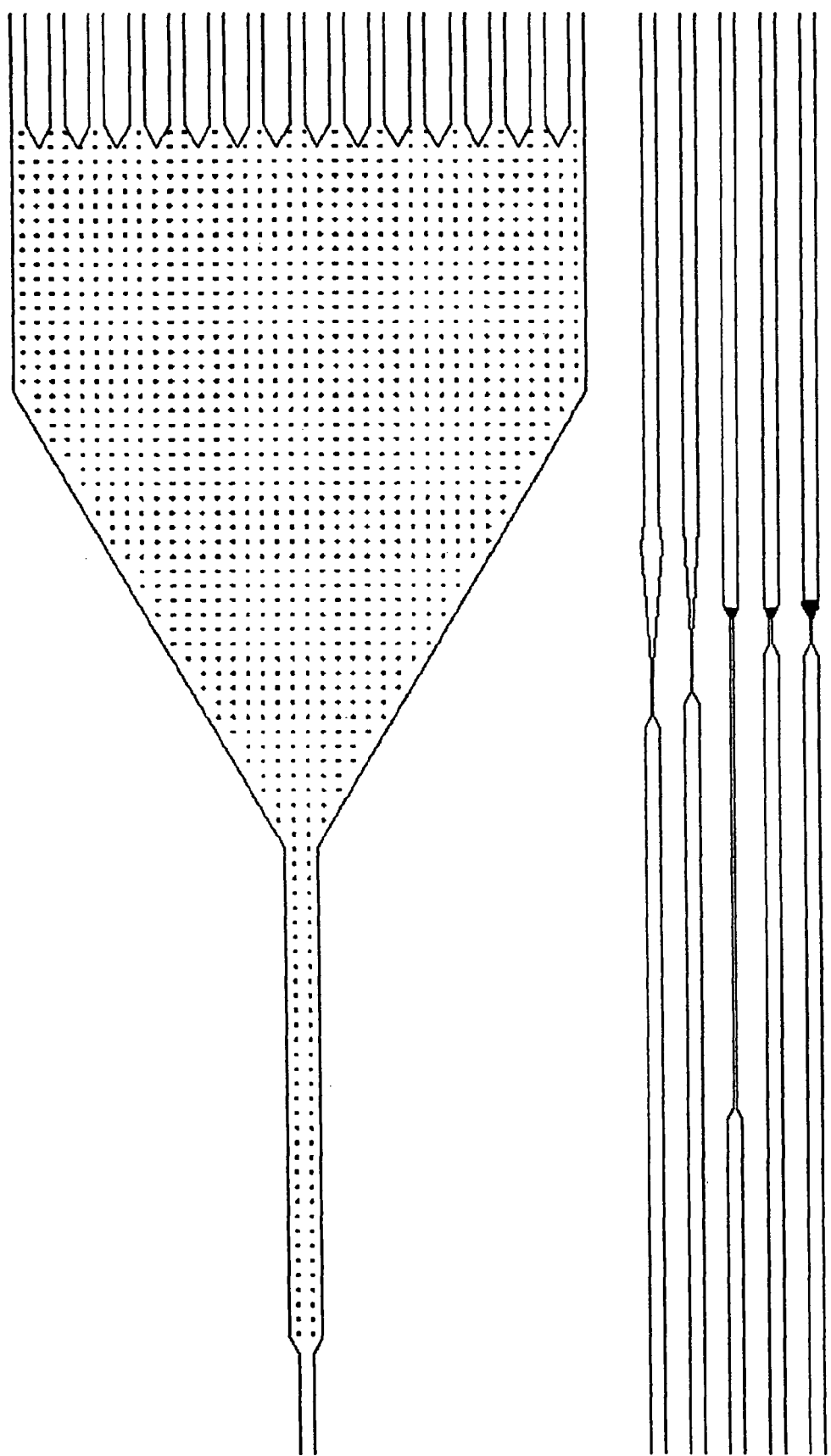

Further examples of structures that fall within the scope of the invention are shown in FIG. 2(a-l). These include, several embodiments of stretching structures involving funnels, obstacles, branches, and serial structures; two funnel structures with posts in serial; embodiments of several complex post arrangements and branched structures; an asymmetric branched structure; a structure with a combination of small obstacles that define small gaps; a structure with a combination of polygonal, bar, and post obstacles; an asymmetric bent structure; a branched structure having posts; a large funnel structure with support posts; a funnel structure with posts; funnel structures with a linear increase in flow rate both with and without posts. FIG. 2(m) is a summary of some of the possible funnel structures. Typically, the elongation structures of the invention can have lengths of from 1 μm to 2 cm, preferably from 1 μm to 1 mm, widths of from 2 μm to 1 mm, and depths of from 0.1 μm to 10 μm.

Each of the four main components of a functional polymer elongation and stretching structure are described below.

Funnel Structures.

Figure 3:
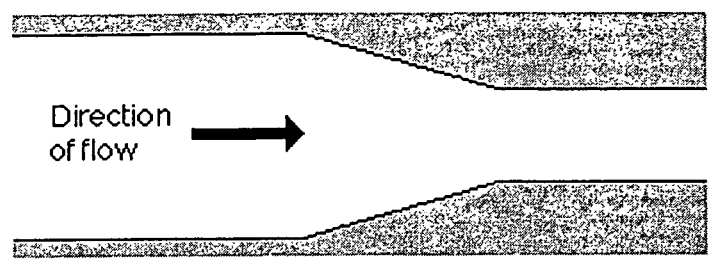
FIG. 3 shows an embodiment of the shear-stretching regime using a constantly-tapered channel.

Funnel structures are tapered channels that apply shear forces in a regular and continuous manner as the polymer flows down the channel. The particular shear forces are defined by the type of channel structure and shape. In one embodiment of the invention, the channel is a tapered channel (FIG. 3) that begins at a given width and continuously decreases to a second width, creating an increasing shear force in the funnel portion of the channel defined by:

$$du/dx=(-Q/H)(dW/dx)(1/W^2) \qquad (13)$$

In one embodiment of the invention, the width decreases linearly so that $dW/dx$ is constant; in this embodiment, the shear, $du/dx$, thus increases as W decreases. In this embodiment, the angle of the funnel as measured from the continuation of a straight wall is preferably between 1° and 75°, with a most preferred value of 26.6° for DNA in a low viscosity solution such as TE (10 mM TRIS, 1 mM EDTA) buffer, pH 8.0. Starting widths for the linear funnel embodiment preferably range from 1 micron to 1 cm, with ending widths preferably in the range of 1 nm to 1 mm depending on the polymer in question, with most-preferred values of 50 microns and 5 microns, respectively, for DNA.

Figure 4:
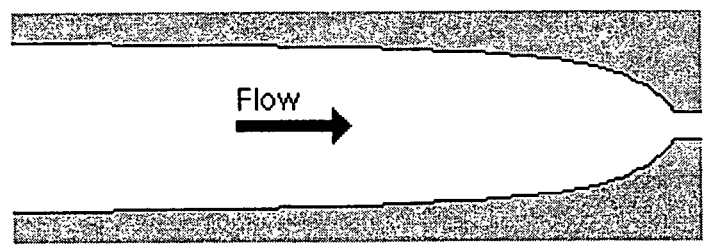
FIG. 4 shows an embodiment of the shear-stretching regime in which the shear rate drastically increases as flow proceeds down the length of the channel.

The channel could also be configured such that the width decreases at an increasing rate as fluid passes down the channel (FIG. 4), resulting in an increase in shear as the channel is traversed. Such tapers offer especially good protection against natural relaxation of the polymer, since as time passes and the molecules move down the channel, they face increasing counter-forces to their tendency to recoil. Furthermore, the increasing force taper allows some design flexibility; any polymer that will encounter shear forces large enough to cause the polymer to stretch in the taper and will not encounter shear forces large enough to cause the polymer to break in the taper can be successfully run through the taper and stretched. There is no need to find the ideal or threshold force for the polymer, only an effective range. In embodiments involving pressure-driven fluid flow (see Driving forces, below), increasing shear also offers the greatest increase in velocity for a given pressure drop, since the final velocity is a function of the cross-sectional area and the pressure drop is a function of the cross-sectional area and length of channel. The same small cross-sectional area (and hence large velocity) can be reached in a shorter distance (and hence smaller pressure drop). In a preferred embodiment, the width of the funnel, W, decreases as $1/(ax^n+b)$, where n is any real number greater than 1, a is a nonzero real number, b is a real number, and x is distance along the length of the funnel (and the direction of polymer flow). Potential equations for the taper of increasing shear force funnels include $W=1/x^2$, $W=1/x^3$, etc.

Figure 5:
FIG. 5 shows an embodiment of the shear-stretching regime using a tapered channel designed to impart a constant shear force.

In yet other embodiments, channels are designed such that the shear rate is constant, leading to a tapered channel such as that shown in FIG. 5. The value of the constant shear rate required to achieve an adequate force to completely stretch the polymer over the course of the channel will vary based on the length of that channel (refer to Eq. (12)). Therefore, 0.01/s might be a reasonable shear rate in order to completely stretch a polymer in a very long, e.g. >1 cm, channel, but might result in almost no polymer stretching in a very short, e.g. <10 µm, channel. Lengths of channels may vary significantly, with preferred values from 10 µm to 1 cm and the most preferred values in the range of 1-2 mm. In one embodiment, the channel is 1 mm long and the shear rate is 0.075/s.

The shear rate of the funnel can be determined by measuring the distance between two known points on a strand of DNA. For example, concatamers of λ DNA are used as standards for shear force measurements. A unique sequence on each concatamer is fluorescently tagged with a hybridization probe. The interprobe distance on the concatamer is thus the length of a single λ DNA molecule (48 kilobases). The physical distance between the probes is determined using video microscopy or time-of-flight measurements. The physical distance for λ DNA in native solution is 14.1 µm. This value is compared with the actual measured physical distance. For instance, if the measured distance is 15.0 µm, then the shear rate can be calculated from the amount of stretching that the DNA has experienced in the stretching structures. The predicted shear on the DNA, as measured by the velocity of the DNA and the dimensions of the channel (see Equation 10), is matched with the elongation of the DNA and its intrinsic non-linear stiffness.

Branched Channels.

Figure 6:
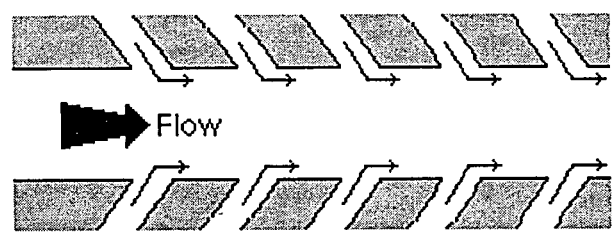
FIG. 6 shows an embodiment of the shear-stretching regime in which the shear comes from the addition of fluid from side channels.
Figure 7A:
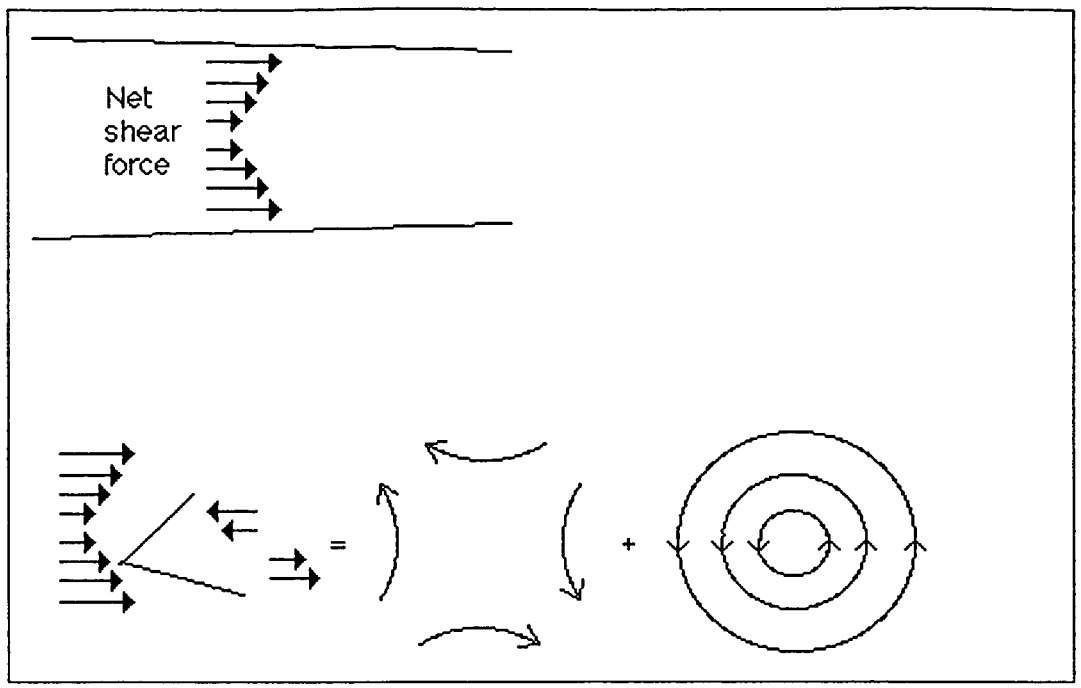
FIG. 7(a) shows how shear force is imparted in a narrowing channel, with local components of rotational and extensional force nearly equal; (b) shows how shear force is imparted when addition of fluid creates the force, with extensional force exceeding the rotational force.
Figure 7B:
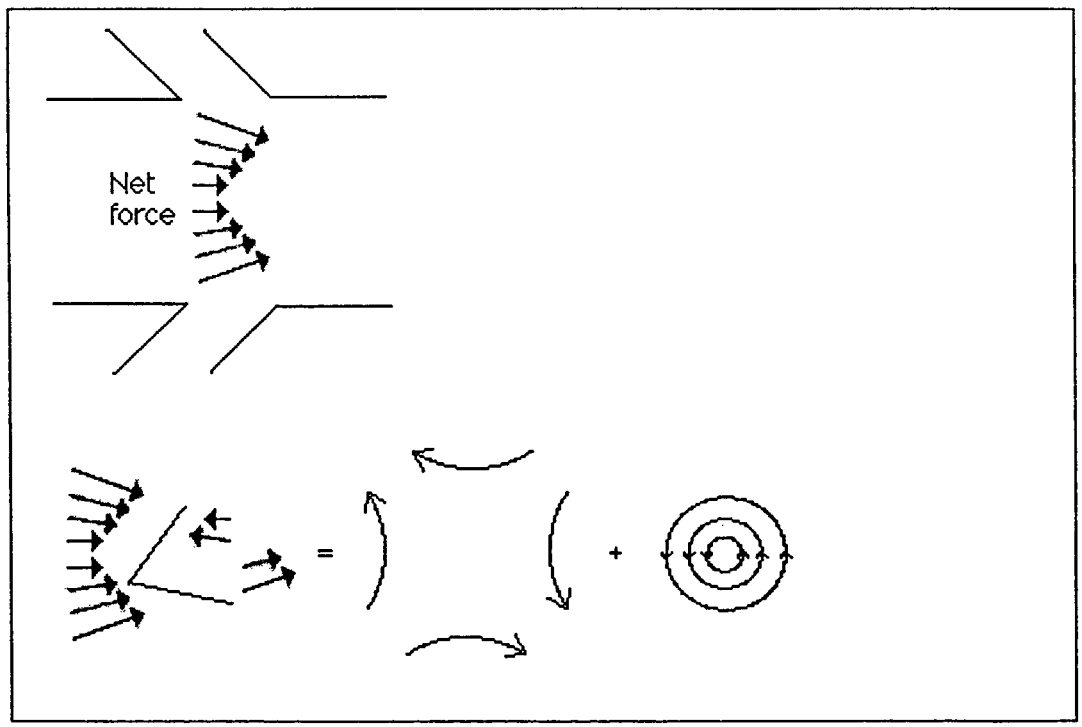

A second aspect of the invention used to stretch and elongate polymers is to create branched structures, which cause either changes in fluid flow rates or changes in polymer directionality (see below in Structures with bends or curves). Side channels feed more fluid into a main channel, resulting in a change in fluid velocity and hence causing polymer stretching. A typical arrangement of branched channels is shown in FIG. 6. Side channels preferably have a combined cross-sectional area ranging from about 1% to 500% of the cross-sectional area of the main channel. Most preferably, side channels have a combined cross-sectional area of about 50% of the cross-sectional area of the main channel. In one embodiment, the side channels are present in a pattern that is repeated, which results in a dilution of the shear force at each individual entrance to the main channel and, hence, a closer approximation of a constant-shear situation. This arrangement highlights the advantages and disadvantages of the side channels. One disadvantage of this component of polymer elongation is that all of the force on the main channel fluid is dissipated in a relatively small region near the junction of the main channel and the side channels. Therefore, this configuration does not lead to a constant-force situation. However, an advantage of this component of polymer elongation is that, because the additional fluid in the side channels is moving in the same direction as the fluid in the main channel, the force is not purely shear force, but has a substantial extensional flow component. Pure shear, which is the force exerted by a tapered funnel on a polymer, is a superposition of extensional forces and rotational forces as shown in FIG. 7(a). The extensional force on a polymer accelerates it in the direction of the fluid flow, such that the portion of the polymer located in the region of extensional flow moves faster than the portion still located in a more stagnant region, stretching out the polymer. The rotational force causes the polymer to spin or "tumble" in conformation, which can cause stretched portions of the polymer to fold up on themselves and recoil. In the embodiments that have stronger extensional forces, such as the side channel junction configuration shown in FIG. 7(b), the polymer tends to accelerate away from the junction, which results in lower rotational forces, thus allowing for better stretching.

As will be appreciated by those of skill in the art, the channel dimensions may be modified and the flow rate increased in the same region of the chip. In fact, a significant increase in the flow rate followed by a constant-shear section is one way not only to stretch out a polymer, but also to direct it away from the walls of the channel. One arrangement embracing this embodiment of the invention is shown in FIG. 8. In yet another embodiment, additional flow is brought in only from one side of the main channel, thereby positioning a polymer traveling down the main channel toward one side. This positioning design could be used to ensure that a polymer is aligned to pass under a narrow detector in a broader channel.

Structures with Bends or Curves.

The third aspect of the invention uses tortuosity to achieve stretching. As fluid flow encounters changes in its path, alignments ranging from a small bend to a right angle, the fluid on the outside of the curve or corner will take longer to go around the turn than the fluid on the inside of the curve or corner (FIG. 9(a)). This so-called "racetrack effect" can help stretch out polymers. Such a bend does not include a "T" junction. In a rectangular section of a channel, a polymer may flow such that it straddles more than one fluid flow line, and since the fluid in each line travels at the same velocity, it retains its configuration. In contrast, when the distance traveled by each fluid flow line diverges at a bend or corner, the polymer is stretched locally by the velocity differential. Furthermore, the polymer tends to move toward the higher-velocity flow line, so that even if the channel curves back to regain its original direction, the polymer does not fully recoil because locally it is within the same flow line. A possible sequence of this kind of stretching is shown in FIG. 9(b). While this effect is insufficient to stretch an entire long molecule in a single set of turns, it can gradually uncoil specific regions, and enough repetition of a tortuous channel can stretch an entire molecule.

One of the gentler incarnations of the tortuosity regime is an embodiment where the configuration of the channel follows a sine wave pattern (FIG. 10). In another embodiment, the channel takes the form of a zig-zag shape (FIG. 11), or, in yet a further embodiment, even a "snake"-shape with only right-angle corners (FIG. 12), though this severe of a corner tends to cause stagnant flows and other undesirable fluid dynamics. For those embodiments where the channel has a zig-zag shape, each bend preferably has an angle between 5° and 75°; for DNA a preferred value of every such angle is 26.6 (effectively a 53.4° angle where the zig-zag reverses). Such zig-zag shapes may be periodic, in which the angle of the bends is always the same, or may comprise a pattern of differential bends. The period of repetition for the zig-zags may vary from as little as 2 µm to 1 cm, with preferred values of 20-50 µm for DNA (1000 times the persistence length). For those embodiments where the channel has a sinusoidal shape, the amplitude to period ratios are preferably between 0.01 and 5. The number of periods for any of these patterns may vary from 1 period to 500, with a preferred value of 10.

In a further embodiment, tortuous channels are used to create multiple detection possibilities. When a detector, such as a position-dependent photomultiplier tube arranged in a 1×256 array, is situated along the direction of flow in the channel, the tortuous channel can be aligned so that it repeatedly crosses the detection zone at defined locations. The polymer being stretched is then observed at several locations, creating redundancy and error checking in the system. Such an arrangement is shown in FIG. 13, with fluid traveling down channel 111 passing through detection zone 110 at six locations, 112-117.

Obstacles Defining Small Gaps.

The fourth aspect of structures which tend to cause stretching is the field of obstacles. As described more generally above, obstacles induce stretching both by reducing the available cross-sectional area of the channel (causing local strain on the molecules) and by acting as physical barriers which cannot be passed by large coils of polymer. One example is a configuration of posts that work to actually stretch a polymer and is shown in FIG. 14.

The obstacles can vary in cross-sectional shape and in cross-sectional area. The terms "cross-sectional shape" and "cross-sectional area," as used herein with reference to obstacles, and unless otherwise indicated, refer to the shape of the X-Y projection and the area of the X-Y plane of the obstacle, respectively, as shown in FIG. 15. In particular embodiments, the obstacles comprise square posts, round posts, elliptical posts or posts with a rectangular cross-section of any aspect ratio (including extremely long "bars"); in other embodiments, the obstacles comprise posts with a cross-section shaped as a regular or irregular non-quadrilateral polygon. In one preferred embodiment, the cross-sectional shape is triangular. In other preferred embodiments, these shapes are modified to have a concave edge-on the edge that faces the direction from which the fluid is coming (such as a shallow U-shape). In still other embodiments, posts having a cross-sectional shape wherein one dimension is longer than the other preferably have an aspect ratio of 2 to 20, more preferably of 2 to 5.

Figure 16B:
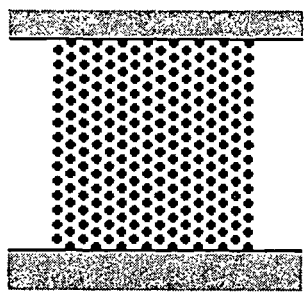

Each of these obstacles may be placed at any angle to the direction of flow. In preferred embodiments, the obstacles are aligned with either a flat surface perpendicular to the direction of the flow, or at a 45° angle to the flow, though if preferential positioning of the polymer molecules is desired, other angles which physically direct polymers toward a destination would be used. Preferably, obstacles wherein one dimension is longer than the other are placed with their longer dimension perpendicular to the flow direction. Another factor in the layout of the obstacles is the grid on which they are placed. If placed on a repeating square matrix (FIG. 16(a)), certain fluid flow lines are almost unaffected by the obstacles, and unstretched or poorly stretched polymers may be able to track along these flow lines and make it through the obstacle field without being stretched. To prevent this, each successive column is preferably offset to place the next obstacle where the gap in the previous column had been (FIG. 16(b)), forcing all flow lines to have curvature and inducing stretching on all passing molecules. The offset may also be less than the full 50% of the repetition unit so that every other column is not in the same alignment as shown in the figures; every fourth or sixth column may have an identical alignment, for example, or there may never be a repetition of alignment, as long as the flow lines at some point are forced to curve around an obstacle.

Besides alignment in the flow, there are two other parameters relevant for obstacles: the size of the passages between them, and the total Y-Z cross-sectional area of the posts relative to the Y-Z cross-sectional area of the channel (FIG. 15), both of which affect the preferred obstacle size. The width of the passages between obstacles should not be smaller than the diameter of the stretched polymer, and is preferably not less than approximately 50 times the diameter of the stretched polymer in order to increase the probability that the polymer will be able to pass through the channel without becoming stuck in the obstacle field. An example of inadequate passage width leading to polymers not getting through the obstacles is shown in FIG. 17. On the other hand, the passages are preferably not as wide as the diameter of the coiled polymer, in which case the coil could pass through the obstacle field without having to stretch at all. Hence, the preferred spacing of the obstacles is highly dependent on the polymer being analyzed. In the case of long DNA with a chain diameter of 2 nm and a coiled diameter varying upward from about 1 µm, the passage width is preferably between 100 nm and 800 nm, with a most preferred value equal to 500 nm. For polymers with a very small diameter, gels may be used in place of obstacle fields, giving pore sizes (equivalent to passage width in the fields) of 1 nm to 1000 nm.

The total Y-Z cross-sectional area occupied by the obstacles most directly impacts the velocity gradients that occur in between the obstacles, and which encourage stretching. Hence, it is preferable to have a larger ratio of obstacle Y-Z cross-sectional area to total channel Y-Z cross-sectional area (also known as the fill ratio, which when expressed as a percentage is given by 100 multiplied by the ratio of the total area of the posts to the total area of the channel) to maximize the velocity gradients. On the other hand, forcing too much material through a relatively small gap can lead to clogging if more than one polymer tries to enter a channel at the same time. Hence, to balance these competing considerations, the fill ratio is preferably between 33% and 95%. This is the ratio of occluded area to total area in a particular channel expressed as a percentage. For example, a post having a 1 µm² Y-Z cross-sectional area in a channel having a 3 µm² Y-Z cross-sectional area has a fill ratio of 33%, while a 20 µm² post in a 21 µm² channel has a fill ratio of 95%. The most preferred value for the fill ratio is between 50% and 80% for DNA. An example of obstacles too large, leading to clogging, is shown in FIG. 18.

In order to alleviate problems with polymers clogging small passages in the post field, differential passage widths are used in some embodiments of the invention. In some embodiments, this is accomplished by varying the size of the obstacles. In other embodiments, this is accomplished by varying the fill ratio. In still other embodiments, both obstacle size and fill ratio are varied. In such embodiments, polymers first encounter wide passages between obstacles and subsequently encounter passages of decreasing widths (FIG. 19), forcing them to gradually become more elongated in order to proceed down the smaller channels. In a preferred embodiment, passage widths are gradated from about 5 µm per passage to about 1 µm per passage in the flow direction. In another embodiment, post sizes are gradated from a cross-sectional area of about 10 µm² to about 1 µm² in the flow direction. In other embodiments, the obstacle cross-sectional area and passage width may be varied individually to achieve similar effects, i.e., the obstacle size may change and the passage size may remain constant, or the passage size may change and the obstacle size may remain constant. In a preferred embodiment, all obstacles have the same cross-sectional area, but the fill ratio increases in the flow direction. The cross-sectional area of the posts can vary from 0.1 µm² to 1 mm², preferably from 0.1 µm² to 10 µm², more preferably from 1 µm² to 100 µm², even more preferably from 1 µm² to 25 µm², depending on the size of the polymer being stretched and the size of the channel used. Such pre-alignment of polymers serves to decrease the possibility of entanglement and hence provides more predictable stretching.

Obstacles can also be fabricated into the depth or z-dimension of the structures, i.e., by introducing "steps" into-the-top and/or bottom of the channel to decrease the depth. Instead of having obstacles placed across a channel, as discussed above, the entire channel can change in depth, providing the same kind of barrier and shear forces around the barrier as obstacles placed along the width of the channel. Furthermore, changes in depth can be relatively inexpensive to implement, as controlling the depth of etching on the sub-micron scale is generally easier than trying to create feature sizes on the sub-micron scale using photolithography. Without being bound by any theory, a significant change in depth at a specific location in essence creates the same effect as a single row of posts, or as a funnel of infinitely short length, x. To approximate a funnel in a fashion that is easy to manufacture using standard microfabrication techniques, the height change can be designed to occur in several steps along the length of the channel, instead of in one step at a single location. In a preferred embodiment, a single-step configuration reduces the height of the channel by a factor of five. In other embodiments, a configuration having at least one step reduces the height of the channel from by about a factor of 2 to by about a factor of 100. In still other embodiments, the steps vary in height from about 0.1 µm to about 0.9 µm.

Combinations of Components.

In further embodiments of the invention, the three general aspects of structures, shear-inducing (i.e., tapered and branched channels), tortuous, and obstacle-filled, are used in combination. The constant-shear tapered channel, for example, is good not only at stretching in itself, but in maintaining stretching in polymers that have already been stretched by obstacle fields. A channel with a tortuous contour can also shrink in width following a constant-shear pattern to capitalize on both effects. In preferred embodiments, a gradated obstacle field or alignment structure is used to pre-stretch the polymer, followed by a section of fine obstacles, tortuous patterns, or high shear area to complete the stretching, and a constant-shear or increasing shear section to maintain the stretching until the detection point is reached.

Applicants have found that an especially effective structure is a combination of an obstacle field upstream of a tapered channel. The obstacle field serves to uncoil the DNA from its random coil configuration, presenting one end of the molecule preferentially to the downstream structure(s). It is advantageous for the obstacle field to be in a wide region of the channel where the flow velocity is relatively low such that the drag force applied to a molecule that becomes folded around or otherwise retained by one of the obstacles is not sufficient to break the molecule. As the molecule winds through the obstacle field, one end will tend to lead the rest of the molecule and enter the tapered channel first. The molecule will then be further stretched by the shear force of the flow through the tapered channel. Without being bound by any theory, applicants have found that the partial uncoiling and end presentation effected by the obstacle field combined with the stretching in the tapered channel is especially effective in accomplishing DNA stretching. Comparison of experimental data from a tapered channel with an upstream post field to data from a tapered channel alone, shows that better stretching is achieved by the combination of the post field and tapered channel under similar conditions of flow and temperature (see Example 2 and FIGS. 29(a) and (b)). The experimental data shows that, while a tapered channel does stretch DNA, a structure that combines a tapered channel with a post field provides significantly greater stretching on average and stretches a greater proportion of the DNA.

In preferred embodiments, an obstacle field, step or alignment structure is used to pre-stretch and align the polymer, followed by a section of constant or increasing shear or elongation to complete and maintain the stretching until the detection region is reached. Preferably, the obstacle field is matched with a tapered channel in a way that avoids contractile flow (i.e., decreasing velocity). Hence it is preferred that posts or steps are located in or terminate at a tapered portion of the channel.

In more preferred embodiments, the channel is a two-funnel structure, that is, it has two tandem regions with different degrees of tapering. An example of a two-funnel structure is shown in FIG. 20. In one embodiment, the two-funnel structure further comprises a post field in the first tapered region. In the two-funnel configuration, stretching of the polymer is completed in the second tapered region (right-most channel region in FIG. 20). Pressure driven flow is the preferred driving force because of its simplicity and ease of application.

In a most preferred embodiment, the structure has a first channel region with a constant width of about 10 µm and a height of about 1 µm in which is placed an obstacle field along the flow direction and leading into a second channel region that is a funnel whose width tapers as $1/x^2$, from a width of about 10 µm to about 1 µm, and whose height is reduced in a single step at the entrance to the funnel from about 1 µm to about 0.25 µm (FIG. 21). The ratio of the initial channel width to the final channel width is preferably greater than 10, and the length of the funnel portion is preferably less than one-half the initial width. The obstacle field preferably comprises at least between 12 and 15 rows of posts having a cross-sectional area substantially equal to 1 µm, wherein the rows have an increasing fill ratio in the flow direction. In one embodiment, six rows have an increasing fill ratio from 0% to 50% in the flow direction, and the subsequent 12-15 rows have a constant fill ratio of 50%, wherein the centers adjacent rows of the subsequent 12-15 rows are at a distance of about 2 µm (FIG. 21). In another embodiment, the rows have a continuously increasing fill ratio from 0% to 80% in the flow direction.

5.4 Structures for Polymer Selection by Length

As described in the previous section, post fields can be used to produce non-random alignment of polymers and to effectively separate one end of the polymer chain from the random coil that is the equilibrium structure of the polymer in solution. If a post field is placed at a distance L from the mouth of a tapered channel, which can be of any shape desired to maintain or produce stretching, e.g., straight, constant shear, or higher order polynomial, the resulting structure can also be used to select molecules by length. This process is illustrated in FIG. 22.

FIG. 22 shows a schematic view of a post field constructed according to the methods described below (see Methods of fabricating structures), positioned before a funnel region of shear or elongational flow. Because the posts fill a portion of the channel, fluid moving through the channel will experience a decrease in velocity as it moves from the post region into the straight section of the channel. This decrease in velocity produces a contracting flow, i.e., the polymer will re-coil in the region of decreased fluid velocity. DNA molecules that travel along the channel and become hooked around a post will be stretched by the flow. If the molecule has a length equal to or longer than the distance L from the posts to the start of the tapered region, it will be released from the post field into the region of elongational flow, in effect spanning the region of decreased fluid velocity without recoiling, and will remain stretched, as shown schematically by DNA molecule 1 in FIG. 22. If the molecule is shorter than L, e.g., DNA molecule 2 in FIG. 22, then it will leave the posts while still in the contracting flow region of the channel, where it will contract rapidly into an equilibrium coil. Therefore, a molecule having a length greater than or equal to L will be stretched and a molecule having a length less than L will not be stretched. If a detector is positioned at the exit from the funnel, as shown in FIG. 22, the signals from coiled molecules (length less than L) and stretched molecules (length greater than or equal to L) will be distinguishable. For example if the detector were monitoring intercalator-stained DNA, contracted molecules would produce a short, intense pulse, whereas fully-stretched molecules would produce a long, less intense signal. Thus it is possible to produce structures that separate mixed populations of polymers into two groups, i.e., those having lengths shorter than L and those having lengths equal to or longer than L, by simply setting L, the distance from the trailing end of the post field to the mouth of the tapered region, to a length that is substantially the same as the length of the molecules from which signal is to be detected.

In another embodiment, it may be desirable to stretch and uniformly detect signal from molecules of all lengths in a given population. This can be done by eliminating the region of contracting flow by, e.g., extending the post field of FIG. 22 into the channel, as shown in FIG. 23. Since the detector is located at the entrance to the channel (as in FIG. 22), where the post field ends, all molecules will be stretched as they pass the detector, and therefore, signals from all molecules, regardless of their lengths, will be detected. In these embodiments, the flow remains constant because the area between the posts is matched to the channel area to which the post field extends.

5.5 Design Considerations

Stretching Considerations and Types of Structures to be Used.

Different structures give rise to different types of DNA stretching and elongation. There is tethered stretching and uniform stretching. Tethered stretching entails creating an unequal force distribution on one end of the molecule to create full extension in a flow profile. Tethered stretching is straightforward to create using obstacles defining small gaps. Uniform stretching, on the other hand, is more complex and involves extensive modeling of polymer dynamics. Uniform stretching is defined as creating a uniform tension over each unit of the DNA molecule. Structures which are designed to create uniform stretching include those with constant shear forces in the x-direction of the design such as funnels with non-linear increases in flow rates.

Polymer Size Considerations.

The structural designs are such that they are scalable and some are universal. Structures can be increased in size, and the relative dimensions changed, in order to accommodate polymer molecules of different lengths. Sizes of interest range from several kilobases to at least megabases of DNA, although there is no upper limit on the length of polymer molecules that can be accommodated. One megabase of DNA has a length greater than 300 microns. Channel dimensions can be made up to several millimeters. In this manner, whole chromosomes (ranging in size from 50-250 megabases) can be handled and stretched.

Configurations of Channels on Overall Chip.

The delivery channels leading to the regions of DNA elongation can include delivery channels which are parallel, radial, branched, interconnected, and closed loops. Delivery channels in the preferred embodiment are wide channels, i.e., 1-1000 microns, which lead to regions of DNA stretching and elongation.

Methods of Fabricating Structures.

The preferred method to fabricate the designed structures is by lithography, such as e-beam lithography, deep-uv lithography, photolithography, LIGA (acronym of the German words "Lithographie," "Galvanoformung," and "Abformung," meaning lithography, electroplating, and molding), and elastomeric molding. Two and three dimensional structures are fabricated by these techniques. Further methods to create three dimensional defined channels include track-etching and molding techniques.

Other methods to create nano-sized obstacles include methods that involve chemical means such as photodeposition of colloids, self-assembly of localized polymers, and cross-linked networks of polymers. For example, a non-linear funnel with localized deposition of agarose gel in the funnel can create an environment of controlled stretching.

Delivery Mechanisms.

Structures intended to stretch out the polymer are not the only ones which may be useful to place in a channel. Structures designed to position the polymer favorably in one part of a channel over another are useful in ensuring that the polymer is fed to a particular stretching structure or to a particular detection zone. Besides the adding of fluid to a single channel as mentioned above (see Branched channels) the positioning can also be accomplished by forcing flow lines closer together. Polymers driven by fluid flow (induced by any of the later-cited methods such as pressure differential and gravity) will principally follow the fluid flow lines (in electrophoresis for charged biopolymers, the polymer follows the field lines, which can be similarly modified). Random motion can cause portions of the chain to move to an adjacent flow line. If the flow lines encounter a constriction or obstacle, the flow lines become closer together around the obstacle, leading to a greater chance that the same lateral random motion will cause a change in flow lines. As the flow lines return to their original spacing on the other side of the structure (if the channel returns to its original width), velocity gradients between the flow lines tend to draw the polymer toward the faster flow lines. In this way, the formerly random distribution of polymer can be made to shift to something more regular. In one embodiment, for example, a large triangle in the middle of a channel with a side perpendicular to the channel facing downstream tends to orient polymers toward the center; this is because polymers formerly near the walls tend to be pulled toward the center by the fluid moving laterally on the downstream side of the triangle. In other embodiments, other shapes are used to help in positioning, such as cross-shaped obstacles, wedges, and obstacle fields with offsets that tend to direct larger channels at a particular side of the channel. While it might seem intuitive that a channel with a simple bend in it should have a positioning effect, the velocity gradients involved are actually quite small and the effect by itself is quite modest.

Methods to Improve Stretching in Structures.

In further embodiments of the invention, the effectiveness of the shear-inducing regimes is enhanced by increasing the viscosity of the solution. The actual force imparted by the constriction of a channel is proportional to the viscosity of the solution. In some embodiments, the viscosity of the solution is increased by the addition of one or more viscosity-modifying components. Glycerol (with a viscosity of nearly 900 cP at room temperature) can be added to an aqueous solution in concentrations as high as 70% (w/v) if it does not react chemically with the polymer. Sugars, such as sucrose, xylose, and sorbitol may also be added. Water-soluble polymers, such as polyethylene glycol, may also be added. In the case of DNA, high molecular weight polyacrylamide, polyethylene oxide or long-chain length polysaccharides (even at concentrations as low as 0.01% by weight) can increase the viscosity of aqueous solutions without modifying the structure of the DNA being characterized.

The viscosity may also be modified by adding an amount of the polymer being characterized, but which will not be detected by the detection zones of the structures. For example, if FRET is being performed on an extrinsically labeled DNA molecule, then additional DNA molecules that are not extrinsically labeled may be added to the labeled polymer solution in order to increase the viscosity. In this way, only labeled molecules are detected and the unlabeled DNA serves only to modify the viscosity of the solution, but does not interfere with signal generation from the labeled molecules.

In another embodiment, viscosity is increased by decreasing the temperature; pure water, for example, nearly doubles in viscosity as it approaches the freezing point. In addition to increasing the viscosity, a decrease in temperature is used to minimize Brownian motion and extend relaxation times. There is a substantial improvement in stretching when an aqueous buffer solution, such as 1×TE solution (10 mM TRIS, 1 mM EDTA), is changed from ambient temperature to 4° C.

Driving Forces.

The driving force for moving the polymer through the structures can come from any means, including physical, electrical, thermal, or chemical forces. The simplest driving force is allowing flow to be driven by capillary action as the first contact is made between the sample solution and the device. While the surface energies involved can provide a high velocity in the channel, control of the flow in this regime is limited.

The use of chemical potential allows for indirect, and hence limited, control. One advantage of setting up a concentration gradient is to provide an extremely slow, steady flow rate. This is accomplished by creating a large excess of a species at one side of the structures and consuming the diffusing species after it induces fluid flow through the structures to the other side, with control based on the excess concentration. The polymer flows through the structures along with the fluid whose flow is induced by the migrating species.

A preferred embodiment directly controls the flow of the fluid. In such an embodiment, a pressure head is established on the entrance side of the structures, encouraging the fluid to flow to the far side, opened to atmospheric pressure or maintained at reduced pressure. The pressure head may come from any device imposing a physical force, such as a syringe pump. Currently, syringe pumps dispense up to the 100 pL/s range, and desired flow rates in a device may be under 1 pL/s, meaning that it may be necessary to create a "bypass channel" with a large cross-sectional area, thus increasing the desired flow rate of the device and allowing control with off-the-shelf equipment, with the loss only of some volume of sample. In another embodiment of the pressure control system, in devices with a pressure drop of less than atmospheric pressure, one end of the system is pulled with a vacuum, literally sucking material to be stretched through the structures. The pressure drop required to induce flow at a desired velocity is a function of the channel geometry (especially the minimum cross-sectional dimension) and that velocity, but is typically within an order of magnitude of 10 psi for 100 micron per second flow in a millimeter-long, micron-deep channel which is otherwise quite wide through most of the device. In another embodiment, a combination of a pressure head at a first end of the channel and a vacuum at a second end of the channel are used to propel a polymer from the first end to the second end.

In yet a further embodiment, the polymer is controlled through the fluid flow by setting up a temperature gradient on each side of the stretching zone. Natural convection then creates a fluid flow through the stretching zone. Since it is much harder to create and control temperature gradients on the micron scale on which these devices operate, this method, like the chemical potential method, is preferably used for very low fluid flow.

In still another embodiment, the flow of the polymer is controlled, for charged polymers such as DNA, by setting up an electric field which acts on the charges on the polymer and not necessarily on the surrounding fluid at all (if it is uncharged). The electric field is preferably established by the presence of two oppositely-charged electrodes in solution, but entire arrays of electrodes can be used to create more complicated or uniform field patterns. The polymers then follow electric field lines instead of flow lines (in some instances an inconsequential change, depending on the physical layout of the chip and the charge density of the solution). This can be damaging to stretching if the surrounding solution contains oppositely-charged objects which flow in the opposite direction (electro-kinetic flow), or surface charges on the wall of the channels causing flow of ions along the walls (electro-osmotic flow), either of which can induce fluid flow in that opposite direction and impart viscous forces on the polymer. However, in a low conductivity solution with walls appropriately coated to avoid surface charge, opposing viscous forces have negligible impact on the electrophoretic driving force, allowing the polymer to proceed through the structures and become stretched. In addition, with an appropriately-charged wall surface, the electro-osmotic flow can be reversed to provide viscous forces which assist the electrophoretic stretching. A field strength of 1000 to 2000 V/m results in usable polymer velocities in the 100 micron per second range.

In the cases of electrophoresis and pressure driving forces, the devices creating the driving force are generally physically separated from the stretching zone. The electrodes are located several millimeters to multiple centimeters away from the stretching zone, with the power supply located even further away. The syringe pump, while advantageous to be as close to the stretching zone as possible to minimize the needed pressure drop, will tend to be placed outside of the device because of its bulk. In fact, for the sake of structural flexibility, it is preferred to place only the stretching and detecting structures themselves on a small chip, preferably no larger than 2 cm on a side, and perhaps as small as 1 mm square, with a most preferred size (from the standpoint of human handling) of about 1.5 cm by 1 cm, with a thickness of 0.2 cm. On that substrate, a variety of fluid flow channels are located. In such a chip, anywhere between 1 and 160 channels may be comfortably placed on the substrate, with 30-40 striking a good balance between having redundancy in the case of channel blockage or substrate flaws and having only one channel in a detection field of view at one time (with a typical 60× objective).

Substrates.

The substrate used is selected for compatibility with both the solutions and the conditions to be used in analysis, including but not limited to extremes of salt concentrations, acid or base concentration, temperature, electric fields, and transparence to wavelengths used for optical excitation or emission. The substrate material may include those associated with the semiconductor industry, such as fused silica, quartz, silicon, or gallium arsenide, or inert polymers such as polymethylmethacrylate, polydimethylsiloxane, polytetrafluoroethylene, polycarbonate, or polyvinylchloride. Because of its transmissive properties across a wide range of wavelengths, quartz is a preferred embodiment.

The use of quartz as a substrate with an aqueous solution means that the surface in contact with the solution has a positive charge. When working with charged molecules, especially under electrophoresis, it is desirable to have a neutral surface. In one embodiment, a coating is applied to the surface to eliminate the interactions which lead to the charge. The coating may be obtained commercially (capillary coatings by Supelco, Bellafonte Pa.), or it can be applied by the use of a silane with a functional group on one end. The silane end will bond effectively irreversibly with the glass, and the functional group can react further to make the desired coating. For DNA, a silane with polyethyleneoxide effectively prevents interaction between the polymer and the walls without further reaction, and a silane with an acrylamide group can participate in a polymerization reaction to create a polyacrylamide coating which not only does not interact with DNA, but also inhibits electro-osmotic flow during electrophoresis.

The channels may be constructed on the substrate by any number of techniques, many derived from the semiconductor industry, depending on the substrate selected. These techniques include, but are not limited to, photolithography, reactive ion etching, wet chemical etching, electron beam writing, laser or air ablation, LIGA, and injection molding. A variety of these techniques applied to polymer-handling chips have been discussed in the literature, including Harrison et al. (Analytical Chemistry 1992 (64) 1926-1932), Seiler et al. (Analytical Chemistry 1993 (65) 1481-1488), Woolley et al. (Proceedings of the National Academy of Sciences November 1994 (91) 11348-11352), and Jacobsen et al. (Analytical Chemistry 1995 (67) 2059-2063).

Additional Considerations.

In preferred embodiments of the invention, the velocity in a given planar height of the channel is substantially uniform in a rectangular channel. This is true when the height is significantly less than the width of the channel, such that the no-slip condition at the wall results in a viscosity-induced parabolic velocity profile that is significant in the height axis, leaving only a small boundary region of slower flow in the width axis. An aspect (width/height) ratio of approximately 10 or greater is required for such embodiments, according to the lubrication theory approximation (Deen, Analysis of Transport Phenomena, New York: Oxford University Press, 1998. 275-278). Furthermore, a small height assists in detection when using a microscope objective in an optical system. Typical objectives may have a depth of focus of 500 nm to several microns, so while the depth of channel could be anywhere from 50 nm to 100 µm as long as the aspect ratio is kept above 10 to accommodate the polymer being analyzed, the preferred embodiments have channel depths of 200 nm to 1 µm such that all material passing by in a channel will be in focus and accurately observed.

The invention also encompasses embodiments where the channels are not planar, and are fabricated with three dimensional channel fabrication techniques. In such embodiments, constant shear is induced not only from side walls, but from a gradient in channel height. Similarly, in further embodiments, combinations of structures have one force acting on one axis and the other force acting in the other. In some such embodiments, an obstacle field spans the width of the channel as its height decreases in a tapered shape. In other embodiments, a tortuous, inward-spiral design in a single plane which also decreases in channel width is used to impart shear forces which feed at its center into a vertical exit from the device through a hole in the bottom of the material, with detection near the entrance to the hole. When structures exist in the vertical dimension, gravity is used in some embodiments to help create velocity differentials in the fluid. (Notably, gravity alone is not adequate to stretch a polymer or move it significantly with a flow since the force on a 100 kD polymer is barely more than $10^{-18}$N; any effect of gravity will be felt by the molecule through viscous forces.)

6. EXAMPLES

6.1 Example 1

Fabrication of a Chip for Stretching DNA and its Use in an Apparatus for Detecting Fluorescence Emission from Labeled DNA Experimental Apparatus.

A sensitive optical apparatus for detection is shown in FIG. 24. The apparatus utilizes confocal fluorescence illumination and detection. Confocal illumination allows a small optical volume (of the order of femtoliters) to be illuminated. Both Rayleigh and Raman scattering are minimized using a small probe volume. The beam from a 1 mW argon ion laser is passed through a laser line filter (514 nm), directed to a dichroic mirror, through a 100×1.2 NA oil immersion objective, and to the sample. The fluorescent tag on the DNA can be one of several dyes including Cy-3, tetramethylrhodamine, rhodamine 6G, and Alexa 546. In addition, intercalator dyes can be used such as TOTO-3 (Molecular Probes). The fluorescence emission from the sample is passed through a dichroic, a narrow bandpass (e.g. Omega Optical), focused onto a 100 µm pinhole, passed through an aspheric lens, and ultimately focused onto an avalanche photodiode in photon counting mode (EG&G Canada). The output signal is collected by a multichannel scalar (EG&G) and analyzed using a Pentium III type computer. The confocal apparatus is appropriate for quantitative applications involving time-of-flight. Such applications include measuring distances on the DNA, detecting tagged sequences, and determining degrees of stretching in the DNA. Single fluorescent molecules can be detected using the apparatus. For applications requiring imaging, an apparatus using an intensified CCD—(ICCD, Princeton Instruments) mounted on a microscope is appropriate.

Fabrication of the Chip.

A set of constant-shear channels with a design shear rate of 0.085/s preceded by two rows of 1.5 micron obstacles on a 2 micron pitch were created in a 0.090 inch thick quartz substrate by photolithography and e-beam methods. The substrate was first cleaned by placement in an RCA solution (5 parts deionized water to 1 part 30% ammonium hydroxide/30% hydrogen peroxide, the latter two from Sigma Chemical Co., St. Louis, Mo.) heated to 80° C. for twenty minutes, and dried under a nitrogen stream. Shipley S1813 photoresist diluted in a 2:1 ratio with type R thinner (Shipley, Newton, Mass.) was then spun onto the quartz surface at 3250 rpm for 45 seconds in a spin coater and cured at 90° C. in an oven for 0.5 hours. The coarse constant-shear pattern was then contact printed onto the surface by a 12 s exposure to a mercury lamp, e.g., in a contact aligner from Carl Zeiss, Germany, followed by a 30 s rinse under 351 developer (Shipley) diluted in a 5:1 ratio with deionized water, further rinses in deionized water, and drying under a nitrogen stream. After a 10 s UV-ozone cleaning, the substrate was exposed to a 40 minute etch by $CHF_3$ in a Reactive Ion Etch (RIE) machine. After another wash in RCA solution, a solution of polymethylmethacrylate (650 MW) diluted to 3% in chlorobenzene was spun onto the surface at 2000 rpm for 45 seconds in a spin coater. The coating was cured for one hour in an oven at 180° C., and a 60 Å layer of chrome was added in an evaporator. An e-beam write was performed to make the fine structures, e.g., the rows of obstacles, followed by a chrome etch in the REI machine and a deionized water rinse. The substrate was then immersed for 90 seconds in a 2:1 v/v solution of isopropyl alcohol: methyl-isobutyl ketone heated to 21° C. for developing, followed by another UV-ozone cleaning. Another $CHF_3$ etch in the REI machine followed by a wash with RCA solution were then performed.

Cover slips (Fisher Scientific, Pittsburgh, Pa.) of dimensions 45 mm×50 mm×0.15 mm were rinsed with deionized water and dried under a nitrogen stream. A 10:1 w/w solution of RTV615A:RTV615B silicone (General Electric, Schenectady, N.Y.) was spun onto the cover slips for 60 seconds at 4000 rpm in a spin coater and was then cured at 80° C. for two hours. A slab of silicone with a hole where the chip is mounted was placed on a cover slip, which was then exposed to a 30 W plasma cleaner for 50 seconds in order to make the surface hydrophilic. The silicone slab was then removed and the cover slip was rinsed in deionized water and dried under nitrogen. The fully-prepared chip was then carefully mounted onto the cover slip.

Apparatus for Monitoring Object-Dependent Impulses from Stretched DNA.

As shown in FIG. 25, the delivery system consists of a polymer supply 151, which is driven by a syringe pump 150 through a chip 152 (see above) where the polymer is stretched out and excited by a laser beam from laser 154 which is detected by optical detector 153 and analyzed by computer 155 that also controls the pump 150 and detector 153.

Monitoring Fluorescence Emission in Stretched DNA.

Coliphage T4 DNA (Sigma, St. Louis, Mo.) was labeled by the addition of 4040-1 at a 5:1 (base-pair:dye) ratio, incubation for one hour, and dilution by a factor of 50,000 in 0.5× TBE electrophoresis buffer (45 mM TRIS, 32.3 mM boric acid, and 1.25 mM EDTA at pH 8.3, all from Sigma, St. Louis, Mo.).

One microliter of sample was then pipetted onto the cover slip immediately next to the chip, where it was loaded into the channels by capillary action. The chip and cover slip were placed on the stage of a fluorescence microscope (Microphot series from Nikon) equipped with a 60× plano apo lens (from, e.g., Nikon or Carl Zeiss). Excitation was from a mercury arc lamp, with a Nikon B2A filter set ensuring adequate excitation near the 490 nm peak excitation of YOYO-1. Emission above 520 nm was passed through the B2A filter set and captured by a silicon-intensified camera (Hammamatsu's C2400-08) or by a CCD camera. The image from the camera was output to a computer through an image capture card (such as the PCI-1408 from National Instruments, Austin, Tex.) and analyzed with image processing software, which was a custom-written routine that identified the DNA on the screen based on its brightness against background and counted pixels to determine polymer length.

Various DNA molecules were observed in this apparatus (FIG. 26). A DNA molecule of approximately 190 kb (63 microns) is shown stretching out in the constant shear section of the chip in FIG. 27 (*a-g*). A DNA fully stretched out in the chip is shown in FIG. 28. This molecule was measured at 139 microns, or 535 kb.

Data.

A small (half-microliter) sample of T4 DNA (Sigma) stained with YOYO-1 (Molecular Probes) was loaded into a chip with a rectangular funnel section incorporating posts and run under capillary action. The sample was excited with a 100 W Hg lamp and observed with a SIT camera (Hammatsu C2400-08). The video signal from the camera was fed to a video capture card in a Pentium-class computer running custom LabView software that determined the length of a piece of DNA in pixels based on its velocity and time spent in the region of interest. Lengths of less than 30 microns were considered to be fragments and were discarded automatically, which led to the obtaining of only ten data points in the approximately two minute run of sample. Using a known conversion for the level of magnification, the DNA were found to be 50.6 µm long, with a range between 42 and 62 µm. A histogram is shown in FIG. 29. The length is somewhat shorter than the expected value of 71.1 µm for a stained 164 kbp T4 DNA, implying the stretching in this design was not fully complete.

6.2 Example 2

Stretching of Phage Lambda DNA Using Apparatuses of the Invention

Two different apparatuses were used to obtain the data shown in FIGS. 30(*a*) and 30 (*b*). The apparatus shown in FIG. 20 was used to obtain the data shown in FIG. 30 (*b*). The apparatus used to obtain the data in FIG. 30 (*a*) had the same channel boundaries as the apparatus used to obtain the data shown in FIG. 30 (*b*) (i.e., the ratio of the sizes of the two tapered regions of the two-funnel apparatus were identical), except that there were no posts present in the structure.

A fused silica wafer (Hoya Corp., San Jose, Calif.) was etched with the pattern in FIG. 20 by a contractor using photolithographic methods described above. The wafer was diced into 1 cm by 2 cm chips using a dicing saw (e.g. from Disco Corp., Santa Clara, Calif.), and a fused silica cover slip (e.g. from Esco, Oak Ridge, N.J.) was attached by thermal bonding.

Double stranded lambda DNA (Promega, Madison, Wis.) having a uniform length of 48.5 kilobases (i.e., an anticipated stretched length of 16-17 microns), was labeled by addition of a like amount of 3 µM TOTO-3 iodide (Molecular Probes, Eugene Oreg.) intercalating dye and then diluted by a factor of approximately 50,000 in 1×TE buffer (10 mM TRIS, and 1 mM EDTA at pH 8.0, all from Sigma, St. Louis, Mo.). The anticipated stretch length of lambda DNA stained with an intercalating dye is 21 µm (approximately 30% longer than unstained DNA) for the double stranded 48.5 kilobase DNA sample used here.

The chip and cover slip were placed on the microscope stage of a fluorescence microscope (e.g., Microphot series from Nikon) equipped with a 100× plano apo lens (e.g., from Nikon, Carl Zeiss) and a filter set optimized for use with TOTO-3 (e.g., XF-47 from Omega Optical, Brattleboro, Vt.). Excitation was from a 633 nm HeNe laser (e.g., from Melles Griot) focused on two spots aligned on the same flow line within the microchannel. The sample was loaded at the entrance of the channels by capillary action and the flow sustained using a vacuum at the other end of the chip (created by a vacuum pump from, e.g., Welch Vaccum, Skokie, Ill.). As DNA molecules passed through the laser spots, emission:

above 650 nm was passed through the filter set and captured by a pair of confocal detectors aligned above the spot. Time of flight between the detectors was used to determine velocity, which was used along with residence time in a laser spot to calculate the lengths of the molecules.

The results of these experiments indicate that the two-funnel apparatus comprising posts stretches 48.5 kilobases of double-stranded, dye-stained lambda DNA to a length of approximately 19.5 μm (FIG. 30 (b)), whereas the two-funnel apparatus without posts only stretches the DNA to a length of about 10 μm (FIG. 30 (a)). Thus, although there is stretching of the DNA in the tapered channel without posts, on average, the DNA is stretched only to somewhat more than half of its full length and very few individual molecules are fully stretched, as is evidenced by the wide distribution of the histogram in FIG. 30 (a). By contrast, in the structure having a post field combined with a downstream tapered channel, the molecules are, on average, stretched to close to full length and the majority of molecules are within 20% of their anticipated fully-stretched length. Therefore, the two-funnel apparatus with posts stretches DNA better than the same apparatus without posts. Furthermore, this apparatus stretches the polymers more uniformly and efficiently than the two-funnel structure without posts.

7. References Cited

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. An apparatus for stretching at least one polymer in a fluid sample, comprising:
   an elongation structure comprising a tapered channel with a longitudinal axis, said tapered channel having a width that is proportional to $1/x^2$ from a first end to a second end, where x is distance along the length of the tapered channel; and
   a plurality of side channels oriented at an oblique angle relative to the longitudinal axis,
   wherein the elongation structure is adapted to stretch the at least one polymer as the at least one polymer moves along said tapered channel from said first end to said second end.

2. The apparatus according to claim 1 wherein said at least one polymer comprises DNA.

3. The apparatus according to claim 1 wherein said first end has a width between 1 μm and 1 cm, and said second end has a width between 1 nm and 1 mm.

4. The apparatus according to claim 1 further comprising a delivery region for delivering said at least one polymer in said fluid sample to said elongation structure.

5. The apparatus according to claim 4 wherein said delivery region comprises a delivery channel, said delivery channel leading into and out of said elongation structure.

6. The apparatus according to claim 1 wherein said plurality of side channels is oriented such that fluid injected from said plurality of side channels moves substantially in the flow direction along said tapered channel.

7. The apparatus according to claim 1 wherein said tapered channel has a tapered-channel cross-sectional area and said plurality of side channels has a total combined side-channel cross-sectional area between 1% and 500% of said tapered-channel cross-sectional area.

8. The apparatus according to claim 7 wherein said total combined side-channel cross-sectional area is about 50% of said tapered-channel cross-sectional area.

9. The apparatus according to claim 1 wherein said plurality of side channels are arranged in a pattern that is repeated.

10. The apparatus according to claim 1, wherein the plurality of side channels are located between the first and second end of the tapered channel.

11. The apparatus according to claim 1, wherein the tapered channel comprises a central channel for containing fluid, and wherein the plurality of side channels branch out from the central channel.

12. The apparatus of claim 1, wherein the elongation structure is formed on a chip.

13. The apparatus of claim 1, wherein at least two side channels are located on different sides of the longitudinal axis.

14. The apparatus of claim 1, wherein the longitudinal axis bisects an angle between at least two side channels.

15. A method for stretching at least one polymer comprising the step of:
   moving said at least one polymer along the channel of the apparatus of claim 1;
   whereby said at least one polymer is stretched in said channel as said at least one polymer moves along said channel from said first end to said second end.

16. An apparatus for stretching at least one polymer in a fluid sample, comprising:
   an elongation structure comprising a tapered channel with a longitudinal axis, said tapered channel decreasing in width at a greater than linear rate from a first end to a second end; and
   a plurality of side channels oriented at an oblique angle relative to the longitudinal axis,
   wherein the elongation structure is adapted to stretch the at least one polymer as the at least one polymer moves along said tapered channel from said first end to said second end.

17. The apparatus of claim 16, wherein the longitudinal axis bisects an angle between at least two side channels.

18. The apparatus of claim 16, wherein at least two side channels are located on different sides of the longitudinal axis.

19. The apparatus of claim 16, wherein said tapered channel decreases in width as $1/(ax^n+b)$, where n is any real number greater than 1, a is a nonzero real number, b is a real number, and x is distance along the length of the tapered channel.

20. The apparatus according to claim 16 wherein said at least one polymer comprises DNA.

21. The apparatus according to claim 16 wherein said first end has a width between 1 μm and 1 cm, and said second end has a width between 1 nm and 1 mm.

22. The apparatus according to claim 16 further comprising a delivery region for delivering said at least one polymer in said fluid sample to said elongation structure.

23. The apparatus according to claim 22 wherein said delivery region comprises a delivery channel, said delivery channel leading into and out of said elongation structure.

24. The apparatus according to claim 16 wherein said plurality of side channels is oriented such that fluid injected from said plurality of side channels moves substantially in the flow direction along said tapered channel.

25. The apparatus of claim 16, wherein the elongation structure is formed on a chip.

26. An apparatus for stretching at least one polymer in a fluid sample, comprising:

an elongation structure comprising a tapered channel with a longitudinal axis, said tapered channel decreasing in width as $1/(ax^n+b)$ from a first end to a second end, where n is any real number greater than 1, a is a nonzero real number, b is a real number, and x is distance along the length of the tapered channel; and a plurality of side channels oriented at an oblique angle relative to the longitudinal axis, wherein the elongation structure is adapted to stretch the at least one polymer as the at least one polymer moves along said tapered channel from said first end to said second end.

27. The apparatus according to claim 26 wherein said at least one polymer comprises DNA.

28. The apparatus according to claim 26 wherein said first end has a width between 1 μm and 1 cm, and said second end has a width between 1 nm and 1 mm.

29. The apparatus according to claim 26 further comprising a delivery region for delivering said at least one polymer in said fluid sample to said elongation structure.

30. The apparatus according to claim 29 wherein said delivery region comprises a delivery channel, said delivery channel leading into and out of said elongation structure.

31. The apparatus according to claim 26 wherein said plurality of side channels is oriented such that fluid injected from said plurality of side channels moves substantially in the flow direction along said tapered channel.

32. The apparatus of claim 26, wherein the elongation structure is formed on a chip.

33. The apparatus of claim 26, wherein at least two side channels are located on different sides of the longitudinal axis.

* * * * *